United States Patent [19]
Carini et al.

[11] Patent Number: 5,315,013

[45] Date of Patent: May 24, 1994

[54] SUBSTITUTED PYRAZOLE ANGIOTENSIN II ANTAGONISTS

[75] Inventors: David J. Carini; John Jonas V. Duncia; Gregory J. Wells, all of Wilmington, Del.

[73] Assignee: E. I. Du Pont de Nemours and Company, Wilimington, Del.

[21] Appl. No.: 925,534

[22] Filed: Aug. 5, 1992

Related U.S. Application Data

[60] Continuation-in-part of Ser. No. 666,594, Mar. 8, 1991, abandoned, which is a division of Ser. No. 279,193, Dec. 6, 1988, Pat. No. 5,015,651, which is a continuation-in-part of Ser. No. 141,669, Jan. 7, 1988, abandoned.

[51] Int. Cl.$^5$ .................................... C07D 231/12
[52] U.S. Cl. .................................... 548/376.1
[58] Field of Search .................................... 548/376.1

[56] References Cited

U.S. PATENT DOCUMENTS

| | | | |
|---|---|---|---|
| 2,470,084 | 5/1949 | Harvill et al. | 260/308 |
| 3,065,241 | 11/9162 | Ugi et al. | 260/308 |
| 3,551,571 | 12/1970 | Pachter et al. | 424/274 |
| 4,147,700 | 4/1979 | Hirai et al. | 260/308 R |
| 4,207,324 | 6/1980 | Matsumura et al. | 424/273 R |
| 4,209,515 | 6/1980 | Heckendorn et al. | 424/248.53 |
| 4,338,453 | 7/1982 | Gall | 548/263 |
| 4,340,598 | 7/1982 | Furukawa et al. | 424/273 R |
| 4,355,040 | 10/1982 | Furukawa et al. | 424/273 R |
| 4,568,685 | 2/1986 | Wright et al. | 514/383 |
| 4,577,020 | 3/1986 | Gall | 544/366 |
| 4,590,201 | 5/1986 | Bochia et al. | 514/359 |

FOREIGN PATENT DOCUMENTS

| | | |
|---|---|---|
| 0103647 | 3/1984 | European Pat. Off. |
| 323841 | 7/1984 | European Pat. Off. |
| 0165777 | 12/1985 | European Pat. Off. |
| 0253310 | 1/1986 | European Pat. Off. |
| 49042668 | 8/1972 | Japan |
| 49101372 | 2/1973 | Japan |

OTHER PUBLICATIONS

Pals et al., *Cir. Res.*, 29, 673 (1971).
Streeten & Anderson, *Handbook of Hypertension*, vol. 5, Clinical Pharmacology of Antihypertensive Drugs, A. E. Doyle (Editor), Elsevier Science Publishers B.V., p. 246 (1984).

*Primary Examiner*—Robert W. Ramsuer

[57] ABSTRACT

Substituted pyrazoles such as

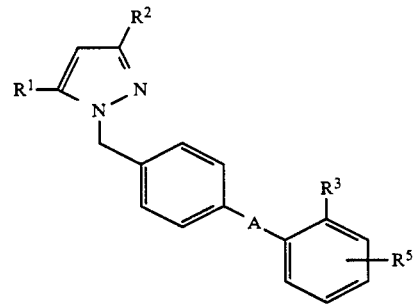

and their pharmaceutically suitable salts are useful as antihypertensive agents and for treatment of congestive heart failure.

3 Claims, No Drawings

SUBSTITUTED PYRAZOLE ANGIOTENSIN II ANTAGONISTS

CROSS-REFERENCE TO RELATED APPLICATIONS

This application is a continuation-in-part of U.S. patent application Ser. No. 07/666,594, filed Mar. 8, 1991, now abandoned, which is a division of U.S. application Ser. No. 07/279,193, filed Dec. 6, 1988, now U.S. Pat. No. 5,015,651, which is a continuation-in-part of U.S. application Ser. No. 07/141,669, filed Jan. 7, 1988, now abandoned.

BACKGROUND OF THE INVENTION

1. Field of the Invention

This invention relates to novel, substituted pyrrole, pyrazole and triazole compounds, processes for their preparation, pharmaceutical compositions containing them, their use as antihypertensive agents, and as a treatment for congestive heart failure in mammals.

2. Background including Prior Art

The compounds of this invention inhibit the action of the hormone angiotensin II (AII) and are useful therefore in alleviating angiotensin induced hypertension. The enzyme renin acts on a blood plasma α-globulin angiotensinogen, to produce angiotensin I, which is then converted by angiotensin converting-enzyme to AII. The latter substance is a powerful vasopressor agent which has been implicated as a causitive agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure.

M. Gall in U.S. Pat. No. 4,577,020, issued Mar. 18, 1986, discloses anti-psychotic triazoles of the formula:

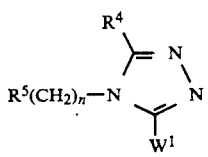

or an enantismer or stereoisomer thereof, wherein $R^4$ is
(a) hydrogen
(b) ($C_1$–$C_3$) alkyl,
(c) —$CH_2OH$,
(d) —$CH_2OCOCH_3$,
(e) —$S(O)_qCH_3$,
(f) —$SCH_2CH_3$, or
(g) —$R^{15}$;
wherein $R^5$, $R^{15}$, and $R^{25}$ are the same or different and are
(a) phenyl substituted by zero to 2 chloro, fluoro, bromo, alkyl of from one to 3 carbon atoms, nitro, or alkoxy of from one to 3 carbon atoms, or
(b) phenyl substituted by one trifluoromethyl and zero to one of the previous phenyl substituents;
wherein $W^1$ is
(a) cis-$C(R^3)$=CH—$CH_2NR^1R^2$,
(b) trans-$C(R^3)$=CH—$CH_2NR^1R^2$,
(c) —$C(CH_3)(OR^{14})$—$CH_2$—$CH_2NR^1R^2$,
(d) a substituent of the Formula III,

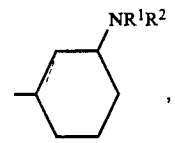

(e) a substituent of the Formula IV

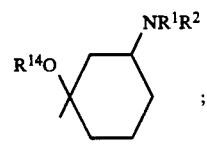

wherein —$NR^1R^2$ is
(a) —$N(CH_3)$—$CH_2(CH_2)_m$—$R^{25}$,
(b) —NH—$CH_2(CH_2)_mR^{25}$,
(c) a substituent of the Formula V

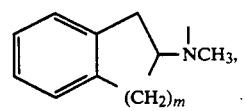

(d) a substituent of the Formula VI

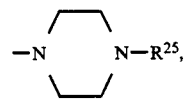

(e) a substituent of the Formula VII

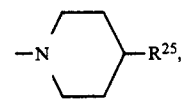

(f) —$N(CH_3)$—$(CH_2)_3$—$CH(R^{51})_2$;
wherein $R^{14}$ is
(a) hydrogen
(b) —$COCH_3$, or
(c) —$COCH_2CH_3$;
wherein $R^{51}$ is
(a) phenyl,
(b) p-fluorophenyl, or
(c) p-chlorophenyl;
wherein $R^3$ is
(a) hydrogen or
(b) methyl;
wherein the dotted line represents a single or double bond;
wherein m is an integer of from one to 2, inclusive;
wherein n is an integer of from zero to 3, inclusive; and
wherein q is an integer of from zero to 2, inclusive;
or a pharmacologically acceptable acid addition salt; or solvate or hydrate thereof.

Hirsch, et al., in European Patent Application 165,777, filed Jun. 14, 1985, disclose N-substituted imidazole and triazole compounds in preparation of medicaments for inhibiting aromatase or preventing or treating estrogen dependent diseases. These compounds are described by the following formula:

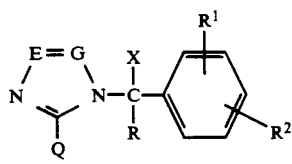

wherein
R is

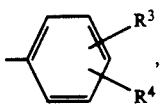

hydrogen, $C_3$-$C_8$ cycloalkyl, $C_1$-$C_4$ alkyl, or acetenyl;
X is

hydrogen, pryidyl, or 5-primidyl, or R and X, when taken together, are $=CH_2$, or when taken together with the carbon atom to which they are attached form a cycloalkyl ring of 5-8 carbon atoms; and
Q is hydrogen or methyl;
where $R^1$ is hydrogen, fluoro, chloro, bromo, methoxy, ethoxy, phenyl, methylthio, methyl, ethyl, nitro, trifluoromethyl, or

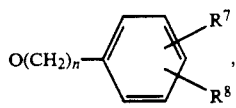

$R^2$, $R^4$, $R^5$, $R^6$, $R^7$ and $R^8$ are independently hydrogen, chloro, or fluoro; or
$R^1$ and $R^2$, when taken together with the benzene ring to which they are attached, form a naphthalene ring;
$R^3$ is hydrogen, fluoro, chloro, trifluoromethyl, methoxy, or nitro;
n is 1 or 2, and
E and G are independently N or CH, provided that E and G may not be N at the same time.
Japanese Patent Application J4 9101-372 discloses anti-inflammatory pyrazoles of the formula

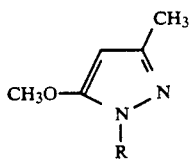

where R is tolyl, p-nitrophenyl, benzyl and phenethyl.
Japanese Patent Application J4 9042-668 discloses the preparation of 1-p-chlorobenzyl-3-methyl-2-pyrazolin-5-one.

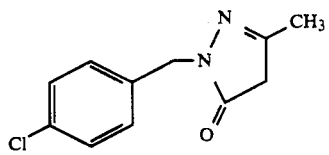

Pals et al., *Circulation Research*, 29, 673 (1971) describe that the introduction of a sarcosine residue in position 1 and analine in position 8 of the endogeneous vasoconstrictor hormone AII to yield an (octa)peptide that blocks the effects of AII on the blood pressure of pithed rats. This analog, [$Sar^1$, $Ala^8$] AII, initially called "P-113" and subsequently "Saralasin", was found to be one of the most potent competitive antagonists of the actions of AII, although, like most of the so-called peptide-AII-antagonists, it also possessed agonistic actions of its own. Saralasin has been demonstrated to lower arterial pressure in mammals and man when the (elevated) pressure is dependent on circulating AII (Pals et al., *Circulation Research*, 29, 673 (1971); Streeten and Anderson, Handbook of Hypertension, Vol. 5, Clinical Pharmacology of Antihypertensive Drugs, A. E. Doyle (Editor), Elsevier Science Publishers B.V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

To date there are no known pep-tide antagonists of AII which are useful orally or which bind in vitro in the $IC_{50}$ ranges we observe, other than those disclosed in the co-pending U.S. applications identified above.

SUMMARY OF THE INVENTION

This invention includes novel, substituted pyrroles, pyrazoles and triazoles, processes for their preparation, pharmaceutical compositions containing them, and their use as antihypertensive agents, and as a treatment for congestive heart failure in mammals. The heterocyclic compounds of the invention have the structural formula (I)

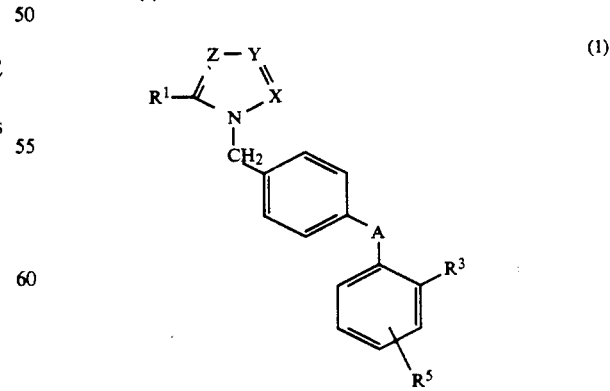

or pharmaceutically suitable salts thereof, wherein X, Y and Z are independently N or $CR^2$ with the proviso that 1) when $R^2 \neq H$, then only one of X, Y and Z can be $CR^2$;
2) when Z=N then Y and X$\neq CR^2$; or
3) when Y=N then Z and X$\neq CR^2$; and
4) when X=Y=N, then Z$\neq$N;
5) when X=N, Y=Z=$CR^2$, then with respect to Y, $R^2 \neq C_{3-4}$ alkyl or $C_4$ alkenyl and with respect to Z, $R^2 \neq$H or Cl and $R^1 \neq (CH_2)_n OR^4$ where N=1 and $R^4 = C_1$ alkyl, A$\neq$carbon carbon single bond, $R^3 \neq CO_2H$ and $R^5 \neq H$.

A is a carbon carbon single bond, CO, O, NHCO, $OCH_2$;

$R^1$ is alkyl of 2 to 6 carbon atoms, alkenyl or alkynyl of 3 to 6 carbon atoms or $(CH_2)_n OR^4$ provided that when $R^1$ is $(CH_2)_n OR^4$ then $R^2$ is H, alkyl of 2 to 6 carbon atoms, alkenyl or alkynyl of 3 to 6 carbon atoms;

$R^2$ is H, alkyl of 2 to 6 carbon atoms, alkenyl or alkynyl of 3 to 6 carbon atoms; $-(CH_2)_n OR^4$;

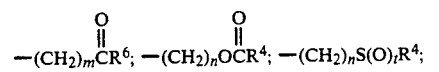

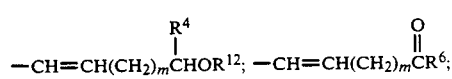

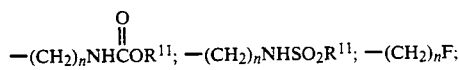

or

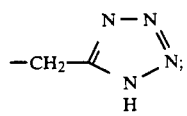

$R^3$ is $-CO_2H$, $-NHSO_2CF_3$; or

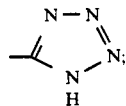

$(CH_2)_n SH$;

$R^4$ is H or alkyl of 1–4 carbon atoms;
$R^5$ is H, halogen, $NO_2$, methoxy, or alkyl of 1 to 4 carbon atoms;
$R^6$ is H, alkyl of 1 to 6 carbon atoms; cycloalkyl of 3 to 6 carbon atoms, $(CH_2)_m C_6H_5$, $OR^7$ or $NR^8R^9$;
$R^7$ is H, alkyl of 1 to 5 carbon atoms, cycloalkyl of 3 to 6 carbon atoms, phenyl or benzyl;
$R^8$ and $R^9$ independently are H, alkyl of 1 to 4 carbon atoms, phenyl, benzyl or $NR^8R^9$ taken together form a ring of the formula

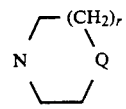

Q is $NR^{10}$, O or $CH_2$;
$R^{10}$ is H, alkyl of 1 to 4 carbon atoms or phenyl;
$R^{11}$ is alkyl of 1 to 6 carbon atoms or perfluoroalkyl of 1 to 6 carbon atoms, $(CH_2)_p C_6H_5$;
$R^{12}$ is H, alkyl of 1 to 4 carbon atoms; or acyl of 1 to 4 carbon atoms;

m is 0 to 6;
n is 1 to 6;
p is 0 to 3;
r is 0 to 1;
t is 0 to 2.

Preferred are compounds of Formula (I) wherein:
A is a carbon-carbon single bond, or NHCO;
$R^1$ is alkyl, alkenyl or alkynyl each of 3 to 5 carbon atoms;
$R^2$ is H, alkyl, alkenyl or alkynyl each of 3 to 5 carbon atoms;

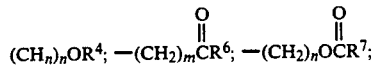

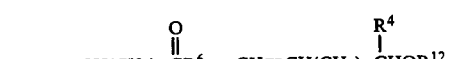

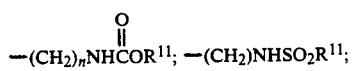

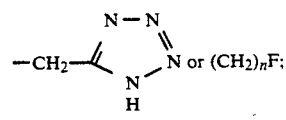

$R^3$ is $-CO_2H$, $-NHSO_2CF_3$ and

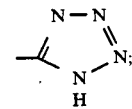

$R^4$ is H or $CH_3$
$R^5$ is H;
$R^6$ is H, alkyl of 1 to 6 carbon atoms, $OR^7$, or $NR^8R^9$;
$R^7$ is alkyl of 1 to 6 carbon atoms;
$R^8$ and $R^9$ independently are H, alkyl of 1 to 4 carbon atoms, or taken together with the nitrogen form the ring

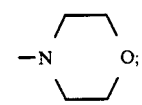

$R^{11}$ is $CF_3$, alkyl of 1 to 4 carbon atoms or phenyl;
m is 0 to 3;
n is 1 to 3;
and pharmaceutically suitable salts thereof.

More preferred are compounds of Formula (I) wherein
A is a carbon-carbon single bond;
$R^1$ is alkyl or alkenyl of 3 to 5 carbon atoms or $CH_2OR^4$;
provided that when $R^1$ is $CH_2OR^4$ then $R^2$ is alkyl or alkenyl of 3 to 5 carbon atoms;
$R^2$ is alkyl or alkenyl of 3 to 5 carbon atoms,

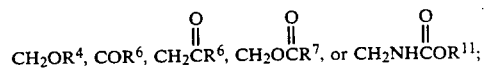

$R^6$ is H, OH, alkyl of 1 to 4 carbon atoms;
$R^7$ is alkyl of 1 to 4 carbon atoms;
and pharmaceutically acceptable salts.

Another embodiment of the present invention is pyrazole compounds of the following formula:

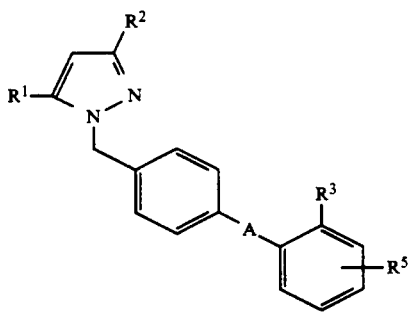

wherein:
R$^1$ is alkyl of 3 to 5 carbon atoms, alkenyl of 3 to 6 carbon atoms, alkynyl of 4 to 6 carbon atoms or (CH$_2$)$_n$OR$^4$;
R$^2$ is alkyl of 2 to 6 carbon atoms, alkenyl of 5 carbon atoms, alkynyl of 3 to 5 carbon atoms, —(CH$_2$)$_n$OR$^4$, —(CH$_2$)$_m$COR$^6$, —(CH$_2$)$_n$OCOR$^4$, —(CH)=CH(CH$_2$)$_m$CHR$^4$OR$^{12}$, —(CH$_2$)$_n$NHCOOR$^{11}$, —(CH$_2$)$_p$C$_6$H$_5$, —(CH$_2$)$_n$NHSO$_2$R$^{11}$, —CH$_2$— tetrazolyl;
R$^3$ is CO$_2$H, NHSO$_2$CF$_3$ or tetrazolyl;
R$^4$ is H or alkyl of 1-4 carbon atoms;
R$^5$ is H, halogen, NO$_2$, methoxy, or alkyl of 1-4 carbon atoms;
R$^6$ is H, alkyl of 1 to 6 carbon atoms, cycloalkyl of 3 to 6 carbon atoms, —(CH$_2$)$_m$C$_6$H$_5$, OR$^7$ or NR$^8$R$^9$;
R$^7$ is H, alkyl of 1 to 5 carbon atoms, cycloalkyl of 3 to 6 carbon atoms, phenyl or benzyl;
R$^8$ and R$^9$ are independently H, alkyl of 1 to 4 carbon atoms, phenyl or benzyl or when taken together R$^8$ and R$^9$ form a ring of the structure:

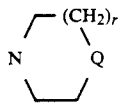

where
Q is NR$^{10}$ or CH$_2$ and r is 0 to 1;
R$^{10}$ is HF alkyl of 1 to 4 carbon atoms, or phenyl;
R$^{11}$ is alkyl of 1 to 6 carbon atoms, perfluoroalkyl of 1 to 6 carbon atoms, or benzyl;
R$^{12}$ is H or alky of 1 to 4 carbon atoms;
A is a carbon-carbon single bond, CO, O, NHCO or OCH$_2$;
m is 0 to 6
n is 1 to 5;
p is 0 to 3;
t is 0 to 2; or
a pharmaceutically suitable salt thereof.
Preferred pyrazoles of this embodiment are wherein:
R$^1$ is alkyl or alkenyl of 3 to 5 carbon atoms;
R$^2$ is alkyl or alkenyl of 3 to 5 carbon atoms or CH$_2$OR$^4$;
R$^4$ is H or alkyl of I to 2 carbon atoms;
R$^5$ is H, halogen, NO$_2$ methoxy or methyl;
R$^6$ is H, methyl or OH;
R$^{11}$ is methyl, benzyl, methyl or CF$_3$;
m is 1;
n is 1; or
a pharmaceutically suitable salt thereof.

Specifically preferred compounds because of their antihypertensive activity are:
3-Methoxymethyl-5-n-propyl-4-[(2'-(1H-tetrazol-5-yl)biphenyl-4-yl)methyl]-1,2,4-triazole;
3-Methoxymethyl-5-n-butyl-1-[(2'-carboxybiphenyl-4-yl)methyl]pyrazole;
5-n-Butyl-1-[(2'-carboxybiphenyl-4-yl)methyl]-1,2,3-triazole;
5-Methoxymethyl-3-n-propyl-1-[(2'-carboxybiphenyl-4-yl)methyl]pyrazole;
3-carboxy-5-n-propyl-1-[(2'-carboxybiphenyl-4-yl)methyl]pyrazole;
5-n-propyl-1-[(2'-carboxybiphenyl-4-yl)methyl]pyrrole-2-carboxylic acid
and pharmaceutically suitable salts thereof.

Pharmaceutically suitable salts include both the metallic (inorganic) salts and organic salts; a list of which is given in *Remington's Pharmaceutical Sciences,* 17th Edition., page 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium and ammonium salts.

DETAILED DESCRIPTION OF THE INVENTION

The novel compounds of Formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformations proposed. This will frequently necessitate judgment as to the order of synthetic steps, protecting groups required, deprotection conditions, and activation of a benzylic position to enable attachment to nitrogen on the heterocyclic nucleus. Throughout the following section, not all compounds of Formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

The approaches described for each class of heterocycle generally encompass two major strategies. The first involves N-alkylation of a preformed mono- or disubstituted heterocycle with an appropriately functionalized benzyl halide. The second involves cycloaddition or cyclocondensation of two or three strategically prepared components to generate directly the heterocycle possessing the functionality needed to produce the final products, following relatively minor transformations (e.g., amide or ether bond formation, deprotection). The approach used for a given example will depend on the availability of starting materials and compatibility of pendant functionality to the required reaction conditions.

In cases where more than one regioisomer was produced during synthesis (e.g., 1,2,3-triazoles, pyrazoles), unequivocal identification of each regioisomer was gained through Nuclear Overhauser Effect (NOE) NMR spectra.

Most of the major reaction pathways leading to 1,2,3-triazoles involve azides and several reviews have been published in this area, G. L'abbe', *Chem. Rev.* 69, 345 (1969); T. Srodsky, in *"The Chemistry of the Azido Group"*, Wiley, New York (1971), p. 331. The most common and versatile approach is the thermal cycloaddition of azides to alkynes; H. Wamhoff in *"Comprehensive Heterocyclic Chemistry"*, S. R. Katritzky (Ed.), Pergamon Press, New York (1984), Vol. 5, p. 705; K. T. Finley, *Chem. Heterocycl. Compd.* 39, 1 (1980). A wide range of functionality on both alkyne and azide components are tolerated in the thermal cycloaddition reaction and the approach to a specific target is generally determined by the availability of requisite precursors. Thus, disubstituted 1,2,3-triazoles, such as 4 in Scheme 1, may be prepared by heating a terminal alkyne 1 with an azide such as 3. Although the 1,4-isomer is often produced regiospecifically, a mixture of 1,4- and 1,5-regioisomers may result. Alternatively, a 4(5)-substituted-1,2,3-triazole may be N-alkylated with an appropriately functionalized benzyl halide such as 5. In this approach, any or all of the three ring nitrogens may compete in the alkylation depending upon the nature of the substituents on either component and the specific reaction condition, H. Gold, *Liebigs Ann. Chem.*, 688, 205 (1965); T. L. Gilchrist, et al., *J. Chem. Soc.*, Perkin Trans. 1, 1 (1975). Thus, compounds such as 6 may also be produced.

As shown in Scheme 2, compounds of the formula (15) where A=NHCO may be prepared from aniline precursor (11) which is available by reduction of the corresponding nitrobenzyl derivative (9). This key intermediate (9) can be made by cycloaddition or alkylation chemistry as described previously for Scheme 1. Compounds of the formula (15) where $R^3$=CO$_2$H may be prepared by reacting anilines (11) with a phthalic anhydride derivative in an appropriate solvent such as benzene, chloroform, ethyl acetate, etc. Often the phthalamic acids (14) precipitate from solution with the reactants remaining behind as described by M. L. Sherrill, et al., *J. Amer. Chem. Soc.*, 50, 474 (1928). Also, compounds of the formula (15) where $R^3$=NHSO$_2$CF$_3$ or tetrazoyl can be prepared by reacting the requisite acid chlorides (13) with anilines (11) by either a Schotten-Baumann procedure or simply stirring the reactants. In a solvent such as methylene chloride in the presence of a base such as sodium bicarbonate, pyridine, or triethylamine. Likewise, anilines (11) may be coupled with an appropriate carboxylic acid via a variety of amide bond-forming reactions such as dicyclohexyl carbodiimide coupling, azide coupling, mixed anhydride synthesis, or other coupling procedures familiar to one skilled in the art.

Scheme 3 illustrates the approach, when A=OCH$_2$, to compounds of the formula (22). Hydrolysis of the methyl ether (18) or benzyl ether (19) affords hydroxy compounds (20) which can be alkylated with the appropriate benzyl halides (21) to give (22). In the case of the methyl ethers (18), the hydrolysis can be effected by heating the ether at temperatures of 50-150° C. for 1-10 hours in 20-60% hydrobromic acid, or heating at 50-90° C. in acetonitrile with 1-5 equivalents of trimethylsilyl iodide for 10-50 hours followed by treatment with water. Hydrolysis can also be carried out by treatment with 1-2 equivalents of boron tribromide in methylene chloride at 10-30° C. for 1-10 hours followed by treatment with water, or by treatment with a Lewis acid such as aluminum chloride and 3-10 equivalents of thiophenol, ethanedithiol or dimethyl disulfide in methylene chloride at 0-30° C. for 1-20 hours followed by treatment with water, or by treatment with aluminum chloride and 3-10 equivalents of thiophenol, ethanedithiol or dimethyl disulfide in methylene chloride at 0-30° C. for 1-20 hours followed by treatment with water. Hydrolysis of benzyl ethers (19) can be accomplished by refluxing in trifluoroacetic acid for 0.2-1 hours or by catalytic hydrogenolysis in the presence of a suitable catalyst such as 10% palladium on carbon and 1 atm of hydrogen. Deprotonation of (20) with a base, such as sodium methoxide or sodium hydride in a solvent such as dimethylformamide (DMF) or dimethylsulfoxide (DMSO) at room temperature followed by alkylation with an appropriate benzyl halide at 25° C. for 2-20 hours affords compounds of the formula (22).

As shown by Scheme 4, the functionalized benzyl azides (25) may be prepared from the corresponding benzyl halides (24) via displacement with an azide salt such as sodium azide in a polar solvent such as dimethylformamide, dimethylsulfoxide or under phase transfer conditions at room temperature for 18-48 hours. The benzyl bromides (24) may be made by a variety of benzylic halogenation methods familiar to one skilled in the art; for example, benzylic bromination of toluene derivatives (23) occurs in an inert solvent such as carbon tetrachloride in the presence of a radical initiator such as benzoyl peroxide at temperatures up to reflux conditions.

Scheme 5 illustrates the preferred approaches for incorporation of A as a single bond (31), ether (34), and carbonyl (37) linker. The biphenyls (31) are prepared by Ullman coupling of 29 and 30 as described in "Organic Reactions", 2, 6 (1944). Ethers (34) can be prepared analogously by an Ullman ether condensation between phenols (32) and halides (33) as described in *Russian Chemical Reviews*, 43, 679 (1974). The benzophenone intermediates (37) are generally available through classical Friedel-Crafts acylation between toluene (35) and the appropriate benzoyl halides (36), G. Olah, "Friedel-Crafts and Related Reactions", Interscience, New York (1963-1964).

Alternatively, the substituted biphenyl precursor (40) and corresponding esters (41) can be prepared by reaction of methoxy oxazoline (39) with tolyl Grignard reagents, S. I. Meyers and E. D. Mikelich, *J. Am. Chem. Soc.*, 97, 7383 (1975) as shown in Scheme 6.

The substituted biphenyl tetrazoles (31; where $R^3$=CN$_4$H) can be prepared from the nitrile precursors ($R^3$=CN) by a variety of methods using hydrazoic acid (Scheme 7, equation b). For example, the nitrile (31) can be heated with sodium azide and ammonium chloride in dimethylformamide at temperatures between 30° C. and reflux for 1-10 days, J. P. Hurwitz and A. J. Thomson, *J. Org. Chem.*, 26, 3392 (1961). Preferably, the tetrazole is prepared by the 1,3-dipolar cycloadditions of trialkyltin or triaryltin azides to the appropriately substituted nitrile (31) as shown in Scheme 7, equation a); described by S. Kozuma, et al., *J. Organo. Chem.*, 337 (1971). The required trialkyl or triaryltin azides are made from the corresponding trialkyl or triaryltin chlorides and sodium azide. The pendant tin group of 42 is removed by acidic or basic hydrolysis and the resultant free tetrazole may be protected with the trityl group by reaction with trityl chloride and trimethylamine to provide 43. Bromination as previously described affords 24. other protecting groups such as P-nitrobenzyl and 1-ethoxyethyl may be used instead of the trityl group to protect the tetrazole moiety as needed. Such protecting groups, among others, can be introduced and removed by procedures found in T. W. Greene, *Protective Groups in Organic Chemistry*, Wiley-Interscience (1980).

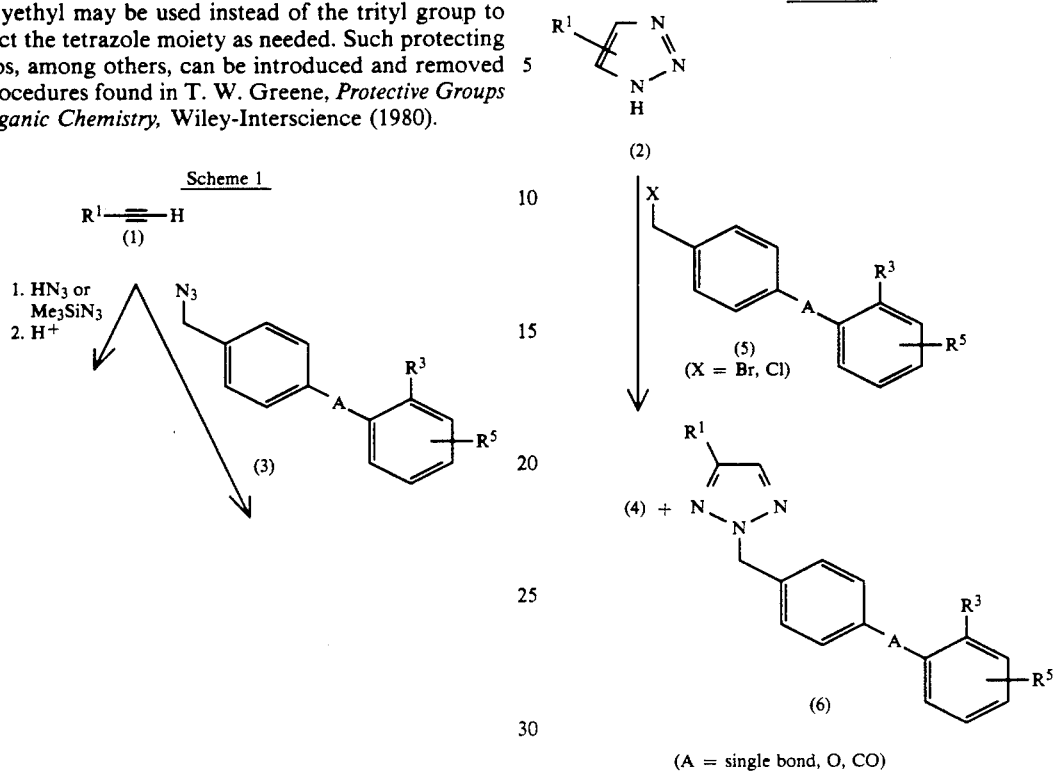

(A = single bond, O, CO)

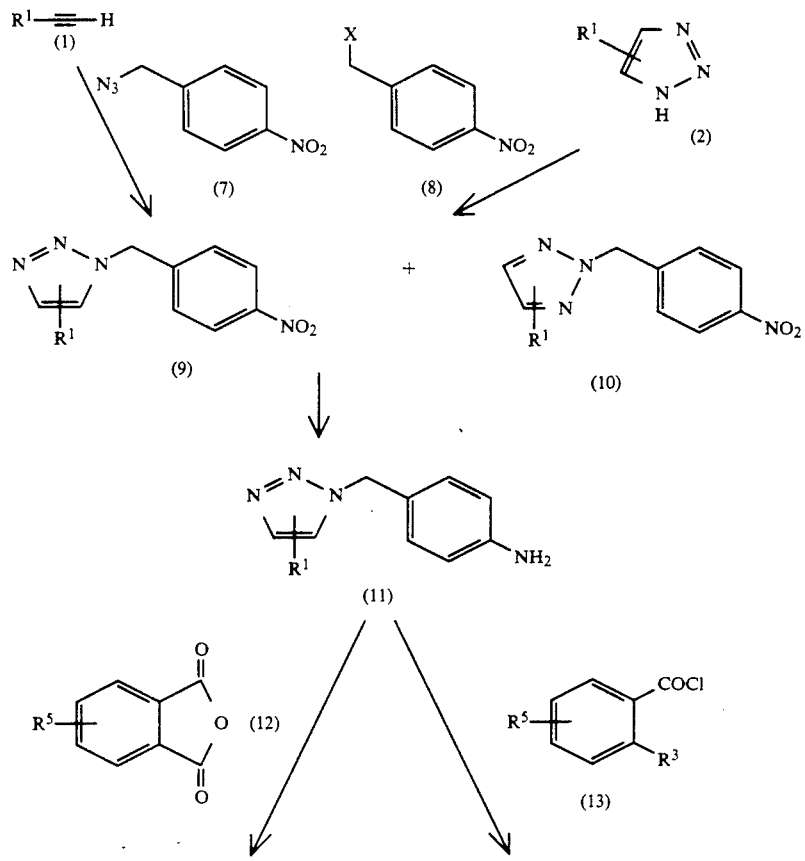

Scheme 2
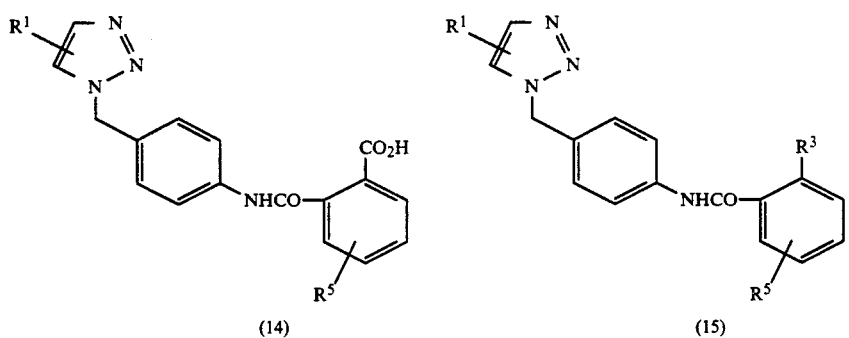
Scheme 3
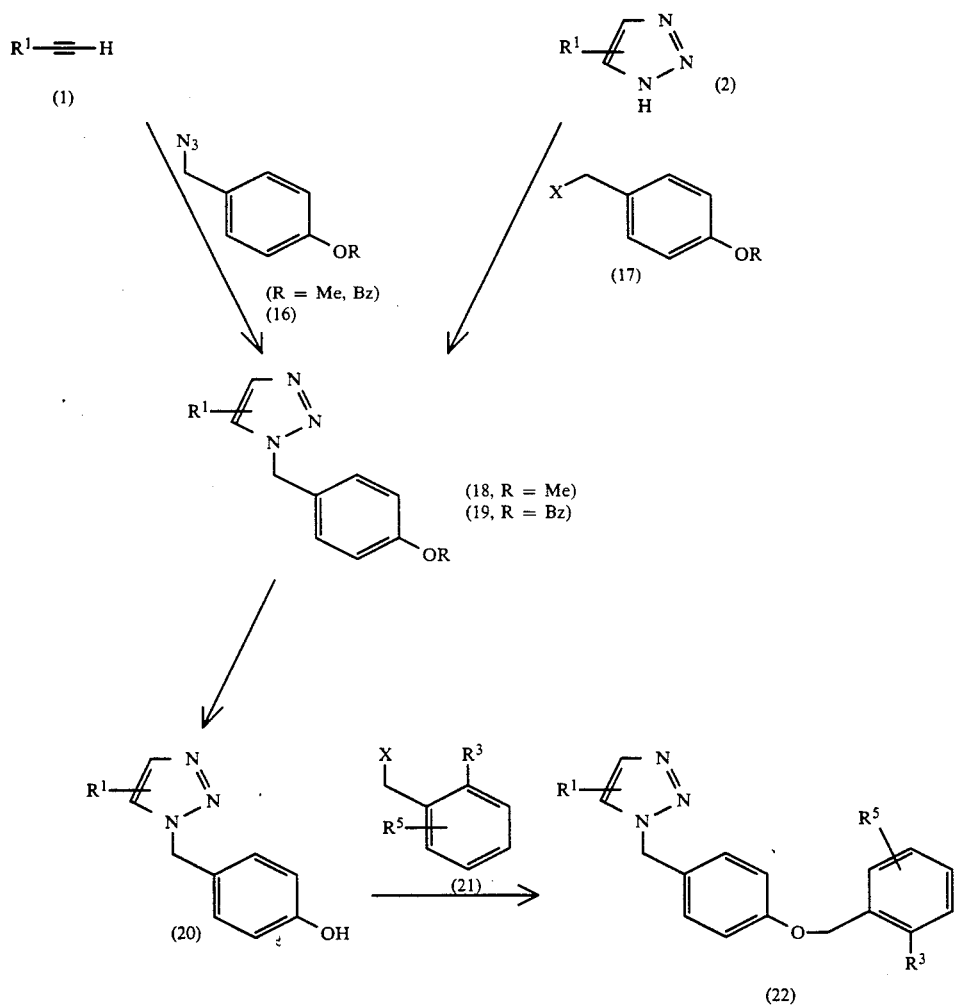

Scheme 4
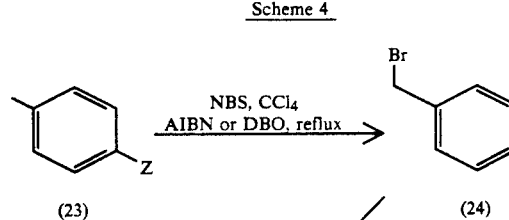
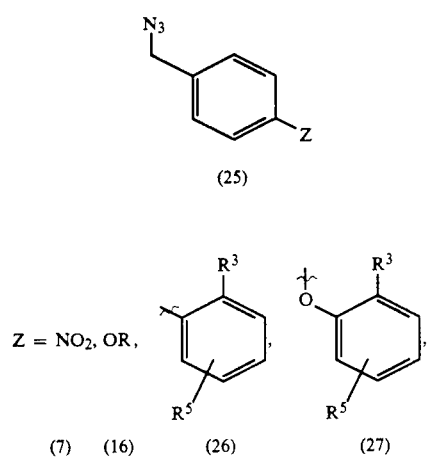
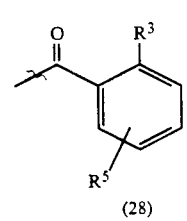
Scheme 5
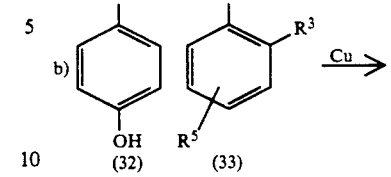
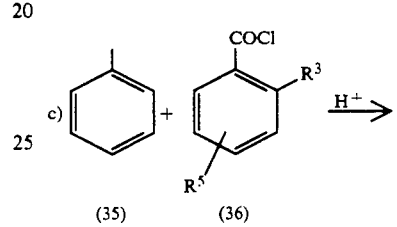
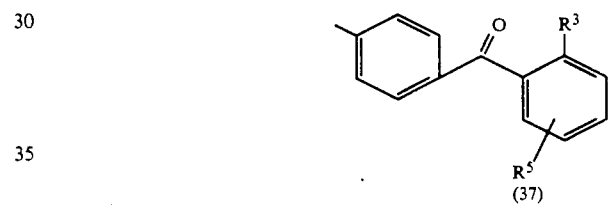
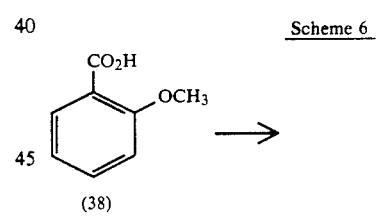
Scheme 5
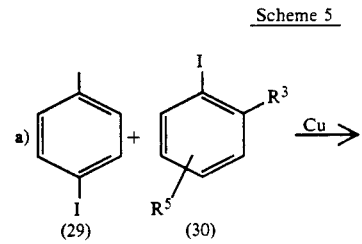
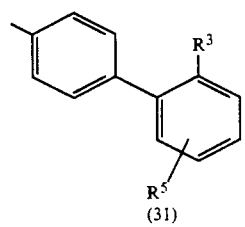
Scheme 6
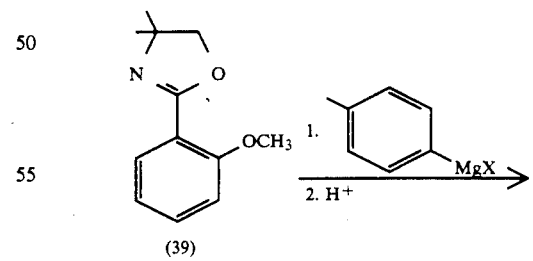
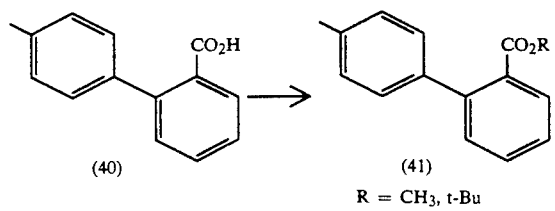

Scheme 7

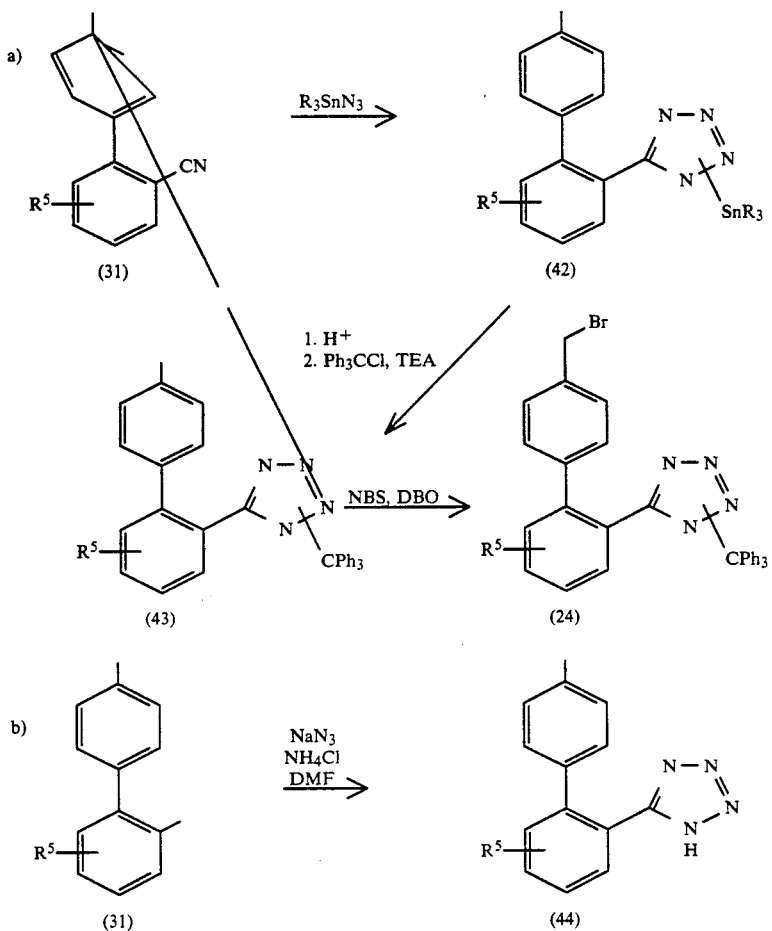

The more common and unambiguous syntheses of 1,2,4-triazoles from acyclic precursors generally involve hydrazine derivatives, due to the ease of forming C-N and C=N bonds over the relative difficulty of forming N-N bonds, J. B. Palya in *Comprehensive Heterocyclic Chemistry*, A. R. Katritzky (Ed.), Pergamon Press, New York (1984), Vol. 5, p. 762. Synthesis of compounds with substituents on N-4 may be approached by methods illustrated in Scheme 8. Reaction of an intimate mixture of orthoesters (45), acylhydrazines (46), and amines (47) in an appropriate solvent like xylenes or any of the lower alcohols at or near the reflux temperature for 1–24 hours produces 1,2,4-triazoles (48) P. J. Nelson and K. T. Potts, *J. Org. Chem.* 27, 3243 (1962); Y. Kurasawa et al., *J. Heterocyclic Chem.*, 23, 633 (1986). Alternative access to such structures may also be gained by condensing N,N'-diacylhydrazines (49) with amines (47) or cyclocondensation of appropriately substituted amidrazones such as (50), *Comp. Het. Chem., Vol.* 5, p. 763.

The versatility of this approach is expanded upon in Scheme 9. Groups $R^1$ and $R^2$ may be carried by either the orthoester (45, 52) or acylhydrazine (46, 51) moieties depending upon their availability. Experimentally, the orthoester and acylhydrazine are first reacted to produce, presumably, 1,2,4-oxadiazoles (53) which may be isolated (if stable) but are commonly reacted in situ with amines (47) (or 58 or 64; Schemes 10 and 11) to ultimately afford (48). Alternatively, oxadiazoles (53) may be transformed to simpler triazoles (54) by treatment with ammonia. Alkylation of this species gives rise to a mixture of N-1 and N-2 substituted products (55), K. T. Potts, *Chem. Rev.*, 61, 87 (1961); K. Schofield, M. R. Grimmett and B. R. T. Keene; *Heteroaromatic Nitrogen Compounds: The Azoles*, Cambridge University Press, Cambridge, (1976), p. 81. N-4 alkylation of simple 1,2,4-triazoles has been observed only rarely, M. R. Atkinson and J. B. Palya, *J. Chem. Soc.* 141 (1954). An alternative approach to such N-1 and N-2 substituted triazoles may be illustrated by reactions between (56) and benzylhydrazines (57). In (56), the dotted lines leave the presence or absence of a bond open, thus allowing possible reactants like ($R^1$COX, $R^2$COX and $NH_3$) or ($R^1CONH_2$ and $R^2COX$) or ($R^1COX$ and $R^2CONH_2$) or ($R^1CONHCOR^2$); X stands for a suitable leaving group like Cl, OH, or $H_2O$.

For compounds in which A=NHCO, the approach utilizes the commercially available 4-nitrobenzylamine (58) in place of the more highly functionalized benzylamines (47). This affords N-4-substituted nitrobenzyltriazoles (59) which may be further elaborated to amide-linked systems (62) and (63) in a manner analogous to that described previously (Scheme 2). Alternative access to (59) may be attained through N,N'-diacylhydrazines (49) or amidrazones in a manner described earlier in Scheme 8. The related N-1(2) substituted systems may be approached by alkylation of (54) with 4-nitrobenzyl bromide (24) as generalized in Scheme 9.

Likewise, for compounds in which A=OCH₂, Scheme 11 shows how use of commercially available 4-methoxy- or 4-benzyloxybenzylamines (64) may produce (65) which can be deprotected and further functionalized as described previously (Scheme 3).

Orthoesters such as (45) and (52) (Scheme 12) are most generally available through alcoholysis of imidate ester hydrochlorides (70) which are usually prepared from the corresponding nitriles (69) by addition of alcohols (usually methanol or ethanol) in the presence of anhydrous hydrogen chloride, R. H. De Wolfe, *Carboxylic Ortho Acid Derivatives: Preparation and Synthetic Applications*, Academic Press, New York, pp. 1–54. The synthesis is usually conducted as a two-step process, the first being preparation and isolation of the imidic ester hydrochloride (70). The lower aliphatic members of this class are often prepared by addition of a slight excess of anhydrous hydrogen chloride to a chilled solution of the nitrile in a slight excess of an alcohol. A suitably inert solvent like ether, benzene, chloroform, nitrobenzene or 1,4-dioxane is then added, the resulting mixture is allowed to stand in the cold (60° C.) for several hours to a week and the product is collected by suction filtration and washed free of residual solvent and hydrogen chloride, S. M. McElvain and J. W. Nelson, *J. Amer. Chem. Soc.*, 64, 1825 (1942); S. W. McElvain and J. P. Schroeder, *J. Amer. Chem. Soc.*, 71, 40 (1949). These imidate esters hydrochlorides are converted to orthoesters by stirring with an excess of an alcohol (generally the same one used above) for up to 6 weeks or, more efficiently, by refluxing the imidate ester hydrochloride with a five to tenfold excess of the alcohol in ether for up to 2 days. Even higher yields can be obtained by stirring the imidate ester at room temperature in a mixture of the alcohol and petroleum ether, S. M. McElvain and C. L. Aldridge, *J. Am. Chem. Soc.*, 75, 3987 (1953) ; Ibid, 80, 3915 (1958). Orthoesters prepared by the above described method may incorporate a rather large array of functionality, including aliphatic, alkenyl, alkynyl, aromatic, halogen, ether, ester, amino, nitro, thio (in various oxidation states), amide, or urethane groups. Another approach, less commonly used, involves electrolysis of trihalomethyl compounds (71) or α-halo ethers, though this approach is limited to halides having no α-hydrogens and is generally applicable to the synthesis of trialkyl orthobenzoates, H. Kevart and M. B. Price, *J. Amer, Chem, Soc.*, 82, 5123 (1960); R. A. McDonald and R. S. Krueger, *J. Org, Chem.*, 31, 488 (1966).

Acyl hydrazines (46, 51) may be prepared in a straightforward manner by reaction of the corresponding esters (72; X=OR) with hydrazine (or hydrazine monohydrate) in an appropriate solvent like alcohol, acetonitrile, DMF or pyrroline at temperatures of 0° C. to reflux for 1 to 18 hours (Scheme 13). The related acid (X=OH), anhydride (X=OCOR), amide (X=NH₂) or acid halide (X=Cl,Br) may also be used, but the more reactive acid derivatives (e.g., acid halides) are generally used for preparation of N,N'-diacylhydrazines (49), except in those instances where the larger size $R^{1(2)}$ groups lead to relatively less reactive species.

Symmetrical N,N'-diacylhydrazines (49) are best prepared by reactions of 2 equivalents of an acylhalide (72; X=Cl,Br) with hydrazine or, alternatively, by oxidation of the corresponding monoacylhydrazine. "Mixed" N,N'-diacylhydrazines (49) are obtained through a two-step process by first preparing the monoacylhydrazine (46, 51) followed by its reaction with the appropriate acyl halide (72; X-Cl,Br).

Benzylhydrazines (57; 77) may be prepared by a variation of the Raschig process for hydrazine by substituting benzyl amines (76) for ammonia and aminating these with chloramine or hydroxylamine-O-sulfonic acid, W. W. Schienl, *Aldrichimica Acta*, 13, 33 (1980) as illustrated in Scheme 14, equation b). Alkylhydrazines have also been prepared from alkyl halides or sulfates. Although the tendency here is towards polyalkylation, monoalkylation is favored by bulky groups (i.e., benzyl, 24) or by use of a large excess of hydrazine, S. N. Kast, et al., *Zh. Obshch, Khim,* 33, 867 (1963); *C.A.*, 59, 8724e (1963).

Benzylamines (76) may be prepared by a variety of methods, some of the more common ones being illustrated in Scheme 14, equation a). The most direct approach, aminolysis of halides, is often accompanied by the formation of secondary, tertiary and even quaternary amines, *J. Amer, Chem, Soc,* 54, 1499, 3441 (1932).

A more efficient approach involves reduction of the corresponding benzylazides (25) by catalytic reduction, hydride reagents, triphenylphosphine or stannous chloride, among others, S. N. Maiti, et al., *Tetrahedron Letters,* 1423 (1986). Reaction of benzylhalides (24) with potassium (or sodium) phthalimide followed by hydrolysis or hydrazinolysis of the intermediate N-benzylphthalimides (73) constitutes the Gabriel Synthesis of primary amines and is highly attractive from the standpoint of the wide range of functional groups tolerated and mildness of conditions for both steps, M. S. Gibson and R. W. Bradshaw, *Angew Chem. Int. Ed. Enel.* 7, 919 (1968). Reductive amination of benzaldehydes (75) with ammonia and hydrogen using a nickel catalyst is another common approach, *Organic Reactions* 4, 174 (1948). Reduction of benzonitriles (74) by metal hydrides or catalytic hydrogenation is also commonly employed, *J. Chem, Soc,* 426 (1942); *J. Amer. Chem. Soc.,* 82, 681, 2386 (1960); *Organic Reactions,* 6, 469 (1951). Other reagents have been employed for conversion of intermediates (24), (74) and (75) to (76), J. T. Harrison and S. Harrison, *Compendium of Organic Synthetic Methods,* John Wiley and Sons, New York, Vol. 1–5 (1971–1984).

Scheme 8

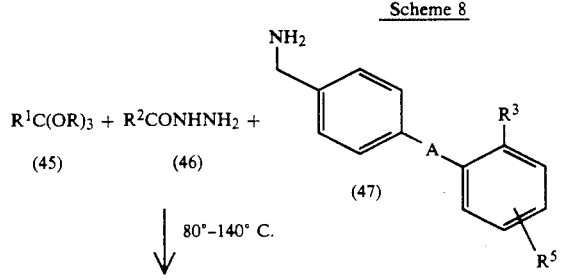

$R^1C(OR)_3$ + $R^2CONHNH_2$ +

(45)      (46)

↓ 80°–140° C.

-continued
Scheme 8
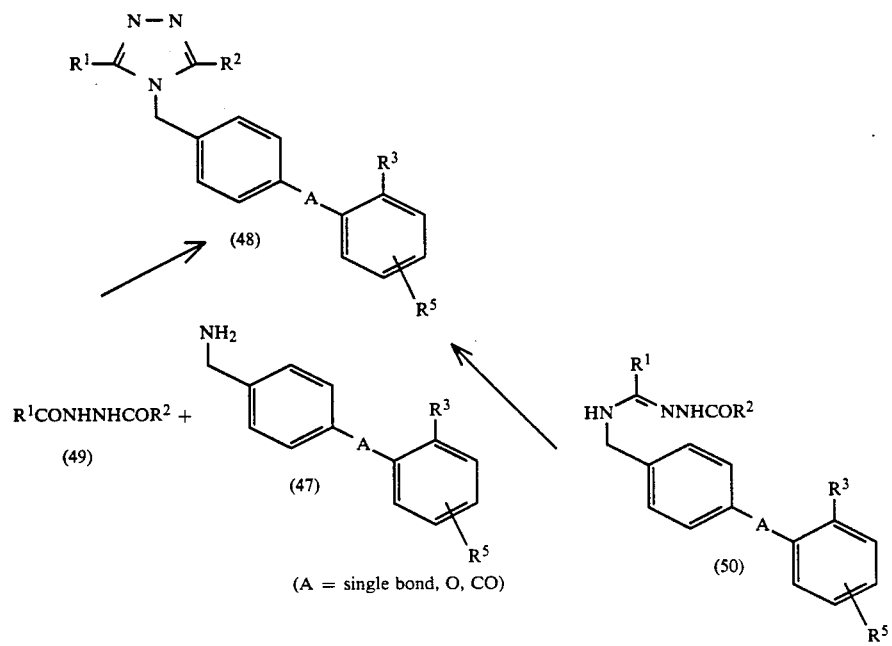
(A = single bond, O, CO)
Scheme 9
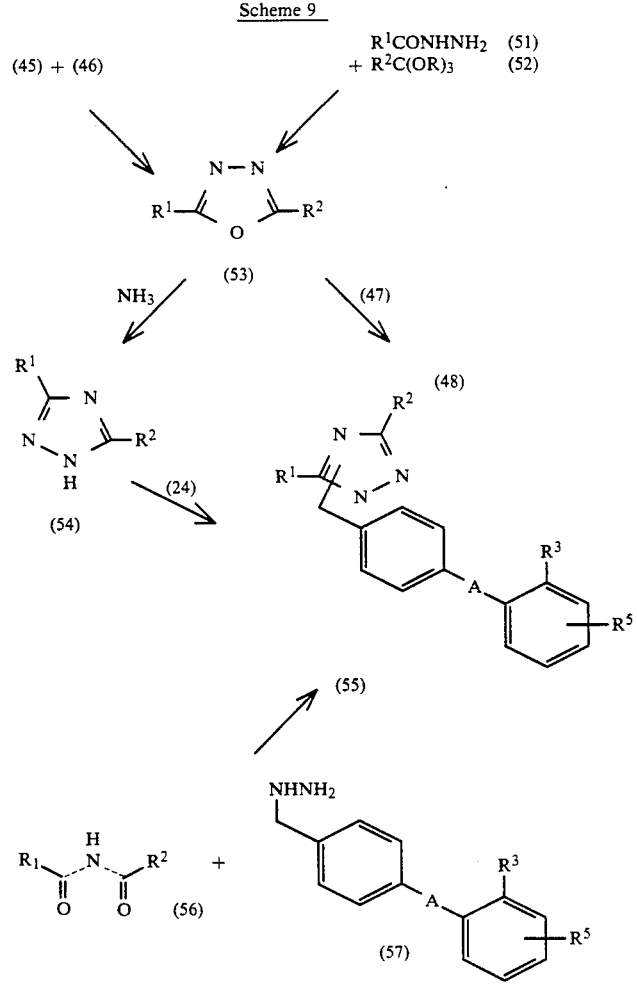

Scheme 10
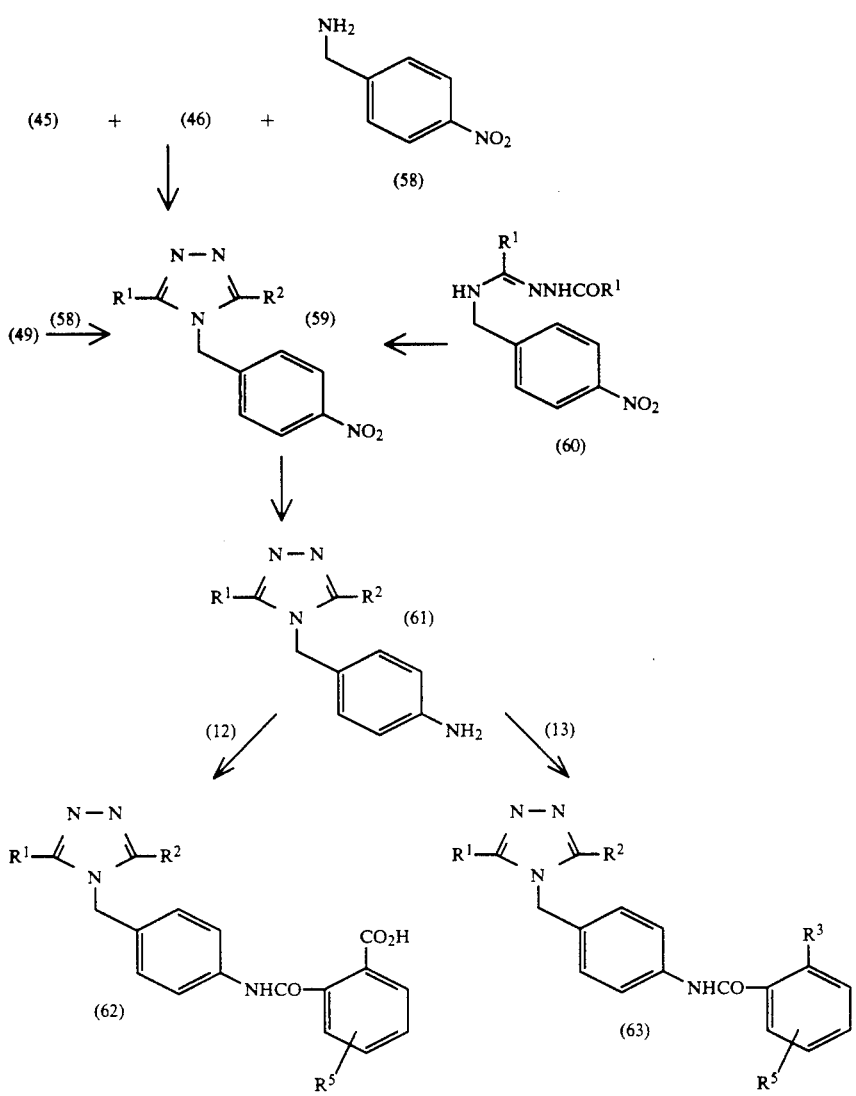
Scheme 11
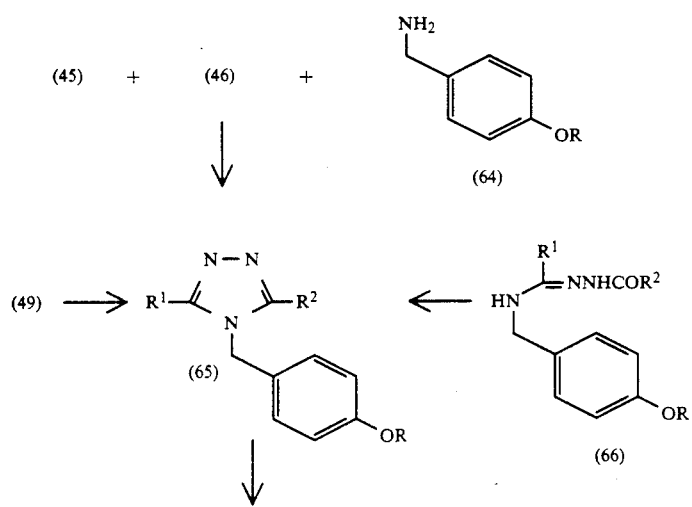

Scheme 11
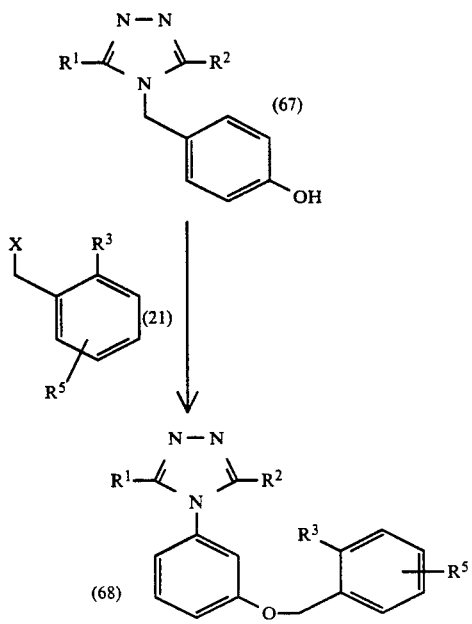
Scheme 12
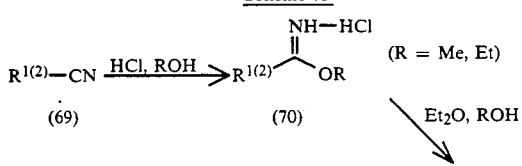
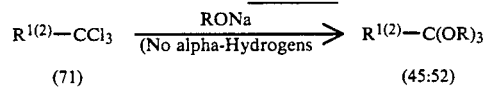
Scheme 13
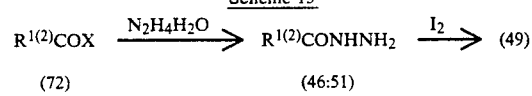
Scheme 14
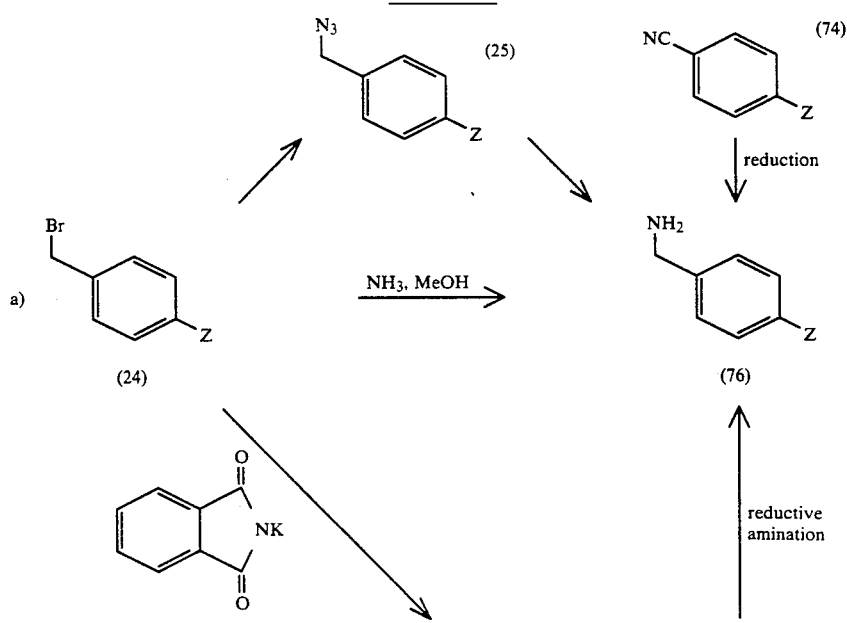

Scheme 14

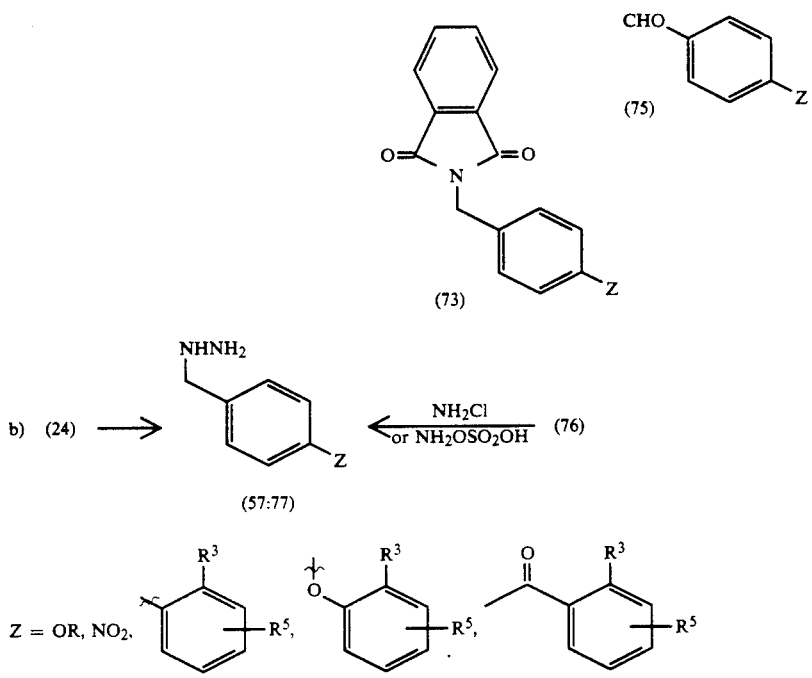

A general and versatile approach to pyrazoles involves condensation of a 1,3-difunctional compound (usually dicarbonyl) with hydrazine or its derivatives, as shown in Scheme 15 for pyrazoles of the formula 80, and reviewed by G. Corspeau and J. Elguerv, *Bull, Soc. Chim. Fr.* 2717 (1970). Rarely have pyrazoles been prepared in which the N-N bond is the last step of the ring closure, J. Elguerv in *Comprehensive Heterocyclic Chemistry*, S. R. Katritzky (Ed.) Pergamon Press, New York, Vol. 5 (1984), p. 274; J. Barluenga, *J. Chem. Soc., Perkin Trans.* 1, 2275 (1983).

For examples, where A=NHCO or OCH$_2$, the compounds of formula 84 and 87 may be constructed via the nitrobenzyl (81) and alkoxybenzyl (85) intermediates, as illustrated in Schemes 16 and 17, respectively, as described for the triazole series (Schemes 2 and 3).

The condensation of 1,3-dicarbonyl compounds with hydrazine hydrate or benzyl hydrazine derivatives is generally carried out by admixture of the two components in a suitable solvent like a lower alcohol, ether, or THF at 0° C. to the reflux temperature for 1-18 hours.

Alkylation of pyrazoles (79) can be carried out either by reactions of a preformed sodium (or potassium) pyrazole salt with an appropriately substituted benzyl halide (5) in a polar solvent like DMF or DMSO at 0° C. to room temperature or by reaction between free pyrazoles (79) and (5) in a like solvent and an acid scavenger such as sodium bicarbonate or potassium carbonate, as described for the triazole series.

In either approach, mixtures of N-1 and N-2 substituted pyrazoles (80, 81, or 85) of varying ratios are generally obtained which can be separated by conventional chromatographic methods.

The synthesis of 1,3-dicarbonyl compounds has received considerable attention in the literature and most of the major approaches towards 1,3-diketones (78) of interest in this invention are illustrated by Scheme 18.

Esters (72; X=OR) can be reacted with methyl ketones (88) using bases like sodium ethoxide, sodium hydride or sodium amide in a suitable solvent like alcohol, DMF, DMSO or benzene at 0° C. to reflux for 4-18 hours with 30-70% efficiency, J. M. Sprague, L. J. Beckham and H. Adkins, *J. Amer, Chem, Soc.*, 56, 2665 (1934). Metallation of hydrazines (89) with n-Buli followed by reaction with carboxylic acid chlorides (72; X=Cl) and subsequent hydrolysis affords 78, D. Enders and P. Wenster, *Tetrahedron Lett.*, 2853 (1978). Metallation of 88 with the non-nucleophilic mesityl lithium followed by acylation also affords 78, A. K. Beck, M. S. Hoelstein and D. Seebach, *Tetrahedron Lett.*, 1187 (1977); D. Seebach, *Tetrahedron Lett*, 4839 (1976).

As shown in Scheme 18, equation b), the addition of Grignard reagents to β-keto carboxylic acid chlorides may be limited to monoaddition at low temperatures to provide 78, C. D. Hurd and G. D. Kelso, *J. Amer, Chem, Soc*, 62, 1548 (1940); F. Sato, M. Trone, K. Oyuro, and M. Sato, *Tetrahedron Lett.*, 4303 (1979). Lithium dialkyl copper reagents (R$^2$CuLi) have also been used, Luong-Thi and Riviera *J. Organomet, Chem*, 77, C52 (1974). Analogously, addition of alkyllithium reagents (R$^2$Li) to the monoanions of β-keto esters (91) also give rise to 1,3-diketones, S. N. Huckin and L. Weiler, *Can. J. Chem*, 52, 1379 (1974).

Eschenmoser has demonstrated a synthesis of β-diketones through a sulfur extrusion reaction of keto thioesters (92) with tributylphosphine, triethylamine and lithium perchlorate, S. Eshenmoser, *Helv. Chim, Acta.*, 710 (1971).

The rearrangement of α,β-epoxy ketones (93) to β-diketones (78) catalyzed by Pd° has been reported, R. Noyori, *J. Amer. Chem. Soc.* 102, 2095 (1980).

Mixed anhydrides such as 25, available from carboxylic acids (94) and trifluoroacetic anhydride, have been shown to acylate alkynes (1) to produce the enol trifluoroacetate of a β-diketone (97). Transesterification by relfuxing with methanol liberates the β-diketone (78), A. L. Henne and J. M. Tedder, *J. Chem. Soc.* 3628 (1953).

Scheme 15
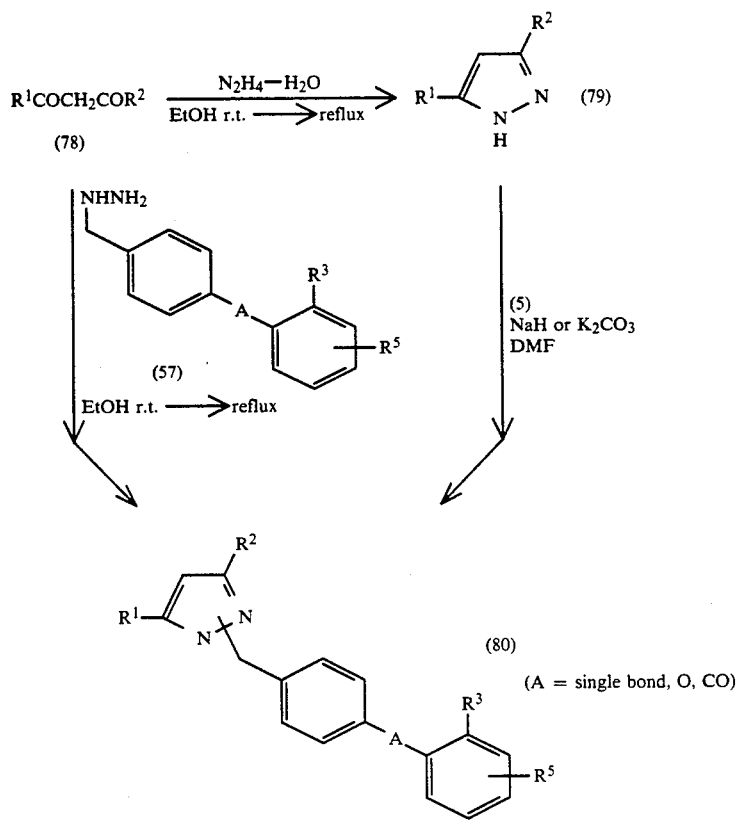
(A = single bond, O, CO)
Scheme 16
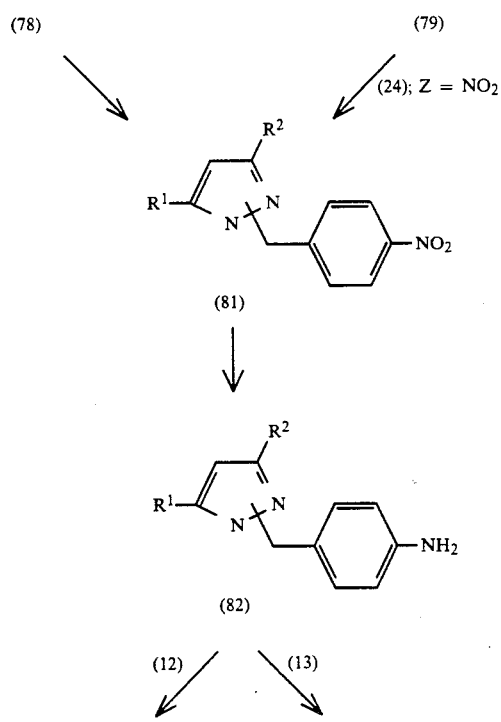

-continued
Scheme 16
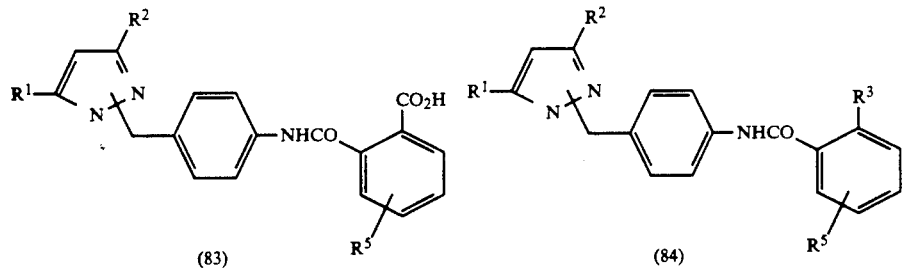
Scheme 17
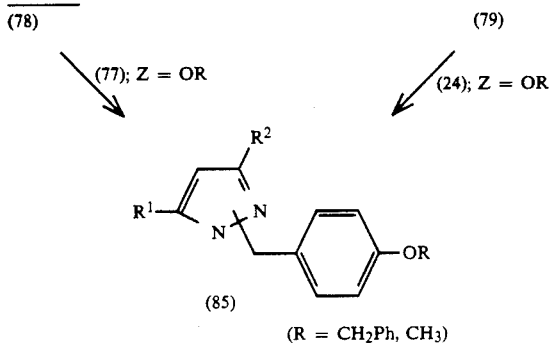
(R = CH₂Ph, CH₃)
-continued
Scheme 17
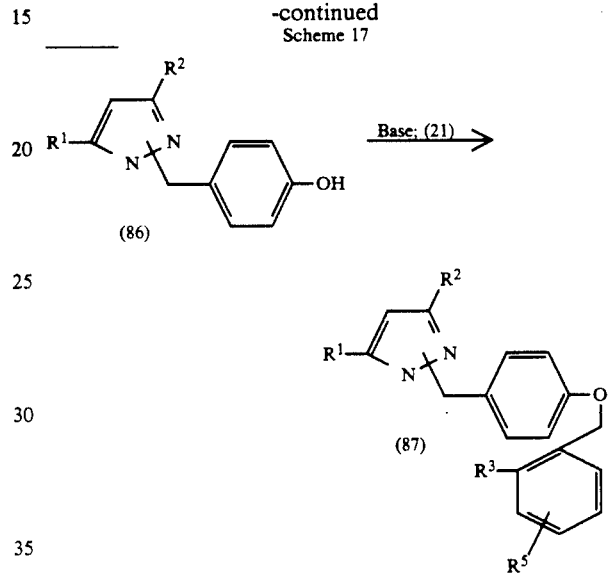
Scheme 18
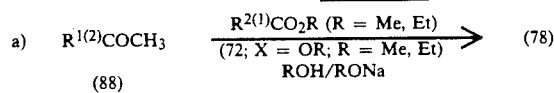
a) 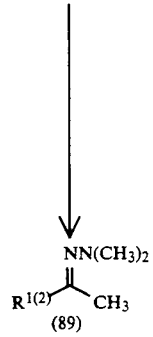
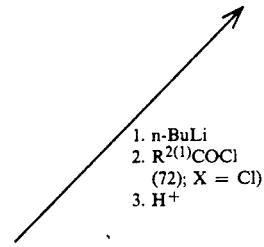
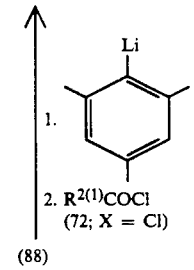
b) 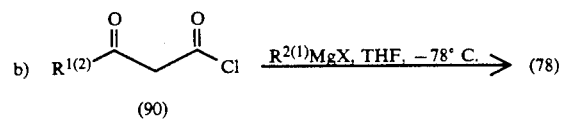
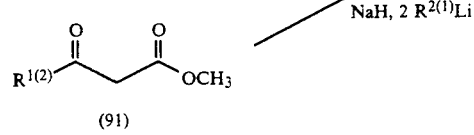

Scheme 18

-continued

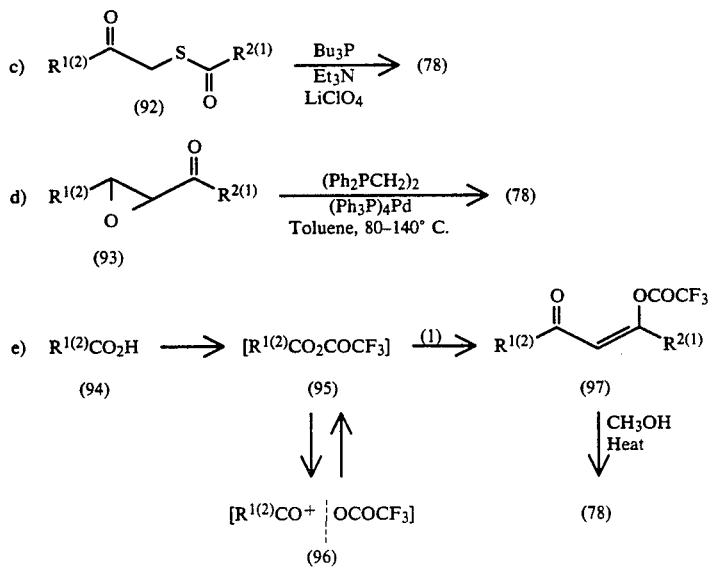

Synthetic approaches towards pyrroles have received wider attention in the literature than most any other heterocycle and numerous methods for their construction have been published. R. J. Sundberg in "Comprehensive Heterocyclic Chemistry", A. R. Katritzky (Ed.), Pergamon Press, New York (1984), Vol, 4, p. 705; *Synthesis*, 1946, 281. The following discussion is restricted to the most common and reliable methods towards the synthesis of pyrroles within the general scope of the invention.

The cyclizative condensation of 1,4-dicarbonyl compounds with annonial primary amines or related compounds, the Paal-Knorr reaction, is one of the most general and widely applicable pyrrole syntheses, R. A. Jones and G. P. Bean, "The Chemistry of Pyrroles", Academic Press, London, 1977; p.77-81. The generality of this approach is primarily determined by the availability of the dicarbonyl precursors, 98, as illustrated by Scheme 19. By heating such diketones with ammonia or amines in a solvent like benzene, toluene or methylene chloride with a catalyst such as sulfuric acid, acetic acid, p-toluenesulfonic acid, alumina or even titanium tetrachloride, pyrroles like 99 may be prepared. By choosing the appropriate arylmethylamine (76, Scheme 14) one may ultimately incorporate the various A-linkers into the fully elaborated pyrroles (100) using methods described earlier (Schemes 1-3). Alternatively, one may alkylate the disubstituted pyrroles (99a) with benzyl halides (24) under conditions previously described (Schemes 1, 9 or 15) to give the same 100.

The cyclization of diynes (101) with amines in the presence of cuprous chloride has been reported (Scheme 20, equation a), but this approach is generally restricted to the preparation of symmetrically substituted pyrroles since the diynes are usually made by oxidative coupling of alkynes, K. E. Schulte, J. Reish, and H. Walker, *Chem. Ber.* 98 (1965); A. J. Chalk, *Tetrahedron Lett.*, 3487 (1972).

Furans (103) have been converted directly to pyrroles by treatment with amines but the harsh conditions required (400° C./Al$_2$O$_3$) precludes its generality. 2,5-Dialkoxytetrahydrofurans (105) have been more commonly employed as furan (or 1,4-dicarbonyl) equivalents and react readily with aliphatic or aromatic amines (and even weakly nucleophilic sulfonamides) to give pyrroles as shown in Scheme 20, equation b), J. W. F. Wasley and K. Chan, *Synth, Commun*, 3, 303 (1973). Although commercially available 2,5-dialkoxytetrahydrofurans (105) (R$^1$=R$^2$=H) generally restrict one to preparing 1-substituted pyrroles, more highly substituted systems may be obtained by a three-step alcoholysis of the appropriate furans (103) to the more highly substituted 2,5-dialkoxytetrahydrofurans (105) as shown by Scheme 20, equation b), N. L. Weinberg and H. R. Weinberg, *Chem, Rev.*, 68, 449 (1968); N. Elming, *Adv. Org. Chem.*, 2, 67 (1960).

The Hantzsch synthesis utilizes the condensation of β-haloketones (106) and β-ketoesters (107) in the presence of ammonia or a primary amine to give pyrroles such as (108), as shown in Scheme 21, equation a); A. Hantzsch, *Chem. Ber.*, 23, 1474 (1980); D. C. von Beelen, J. Walters, and S. von der Gen, *Rec. Trav. Chim.* 98, 437 (1979). Among the numerous modifications reported over the years, the substitution of (106) with the readily available α-hydroxyaldehydes or nitroalkenes has expanded the versatility and generality of this important method, D. M. McKinnon, *Can. J. Chem*, 43, 2628 (1965); H. George and H. J. Roth, *Arch. Pharm.* 307, 699 (1974); C. A. Grok and K. Camenisch, *Helv. Chem. Acta*, 36, 49 (1953).

The closely related Knorr condensation involves the reaction between amino carbonyl compounds (or their precursors) and carbonyl (or dicarbonyl) compounds, J. M. Patterson, *Synthesis*, 282 (1976). Representative methods for preparing 2,3- or 2,5-disubstituted pyrroles (111 and 114) are shown by Scheme 21, equations b) and c), S. Umio et al., Jap. Pat. 7018653, Fujisawa Pharmaceutical Co., Ltd., 1970 (*C.A.* 73, 77039, 1970); K. Tanaka, K. Kariyone, S. Umio, *Chem. Pharm. Bull.* (Tokyo), 17, 611 (1969).

The elaboration of an appropriately functionalized pyrrole is another method for preparing pyrroles of general formula I. Methyl (or ethyl) 5-formyl-1H-pyrrole-2-carboxylate (119) is a particularly useful intermediate as regards pyrroles claimed in this invention and has been prepared by a number of methods as shown by Scheme 22, eq. a, W. A. Davies, A. R. Pinder and I. G. Morris, *Tetrahedron* 18, 405 (1962); *Org. Syn.*, Vol. 36, p. 74; *Org. Syn., Vol.* 51.

More recently, Ullrich has extended the Vilsmeyer-Haack formylation of pyrroles to include vinylogous systems such as (122) by using 3-(N,N-dimethylamino)acrolein (121) as a vinylogous N,N-dimethylformamide derivative, as shown by Scheme 22, eq. b, F. W. Ullrich and E. Breitmaier, *Synthesis*, 641 (1983); W. Heinz, et al., *Tetrahedron*, 42, 3753 (1986).

An especially attractive approach to pyrroles claimed in this invention has recently been reported, whereby lithiation of the 6-dimethylamino-1-azafulvene dimer (125) followed by treatment with an appropriate electrophile and subsequent hydrolysis leads to 5-substituted pyrrole-2-carboxaldehydes (99a; $R^2$=CHO), as illustrated in Scheme 23, J. M. Muchowski and P. Hess, Tetrahedron Lett., 29, 777 (1988).

Scheme 23a illustrates generally how N-alkylation of (99a) with the appropriate benzyl halides (as discussed earlier, Schemes 1, 9 or 15), followed by standard manipulation of the pendant groups using methods familiar to one skilled in the art can produce pyrroles of general formula I (100).

Scheme 19

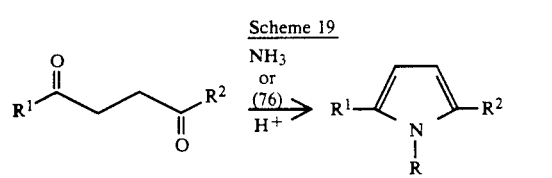

(99a), R = H
(99b), R = CH$_2$Ar

(24) (on 99a)
K$_2$CO$_3$, DMF, 65° C.

(100)

Scheme 20

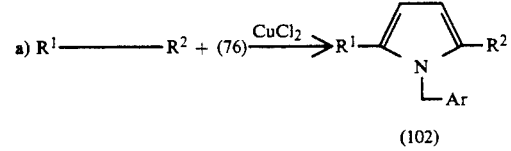

(102)

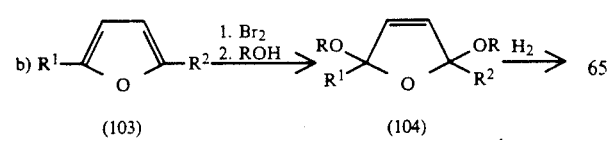

(103)        (104)

-continued
Scheme 20

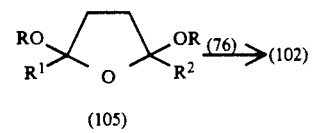

(105)

Scheme 21

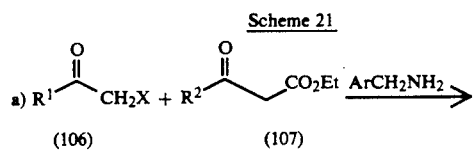

a) $R^1\overset{O}{\underset{}{\|}}CH_2X + R^2\overset{O}{\underset{}{\|}}CO_2Et \xrightarrow{ArCH_2NH_2}$ (106)        (107)

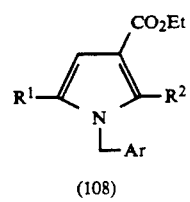

(108)

b) RCH$_2$COCO$_2$H + H$_2$NCH$_2$CH(OEt)$_2$ $\xrightarrow{\text{AcOH, NaOAc}}$ (109)        (110)

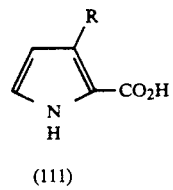

(111)

c) RCOCH=CHOH + H$_2$NCH(CO$_2$Et)$_2$ $\xrightarrow{\text{NaOAc}}$ (112)        (113)

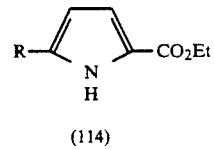

(114)

Scheme 22

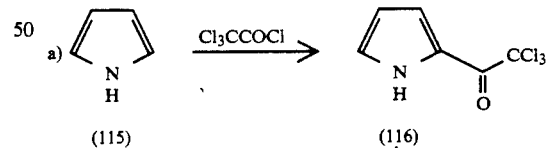

(115)        (116)

NaOEt, EtOH

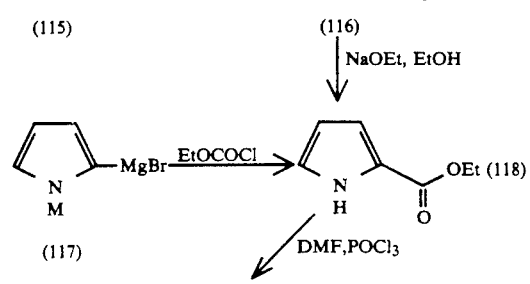

(117)

DMF, POCl$_3$

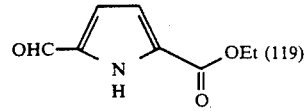

-continued
Scheme 22

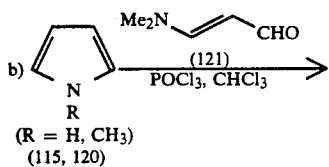

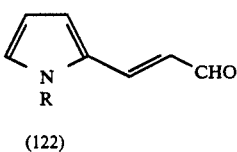

Scheme 23

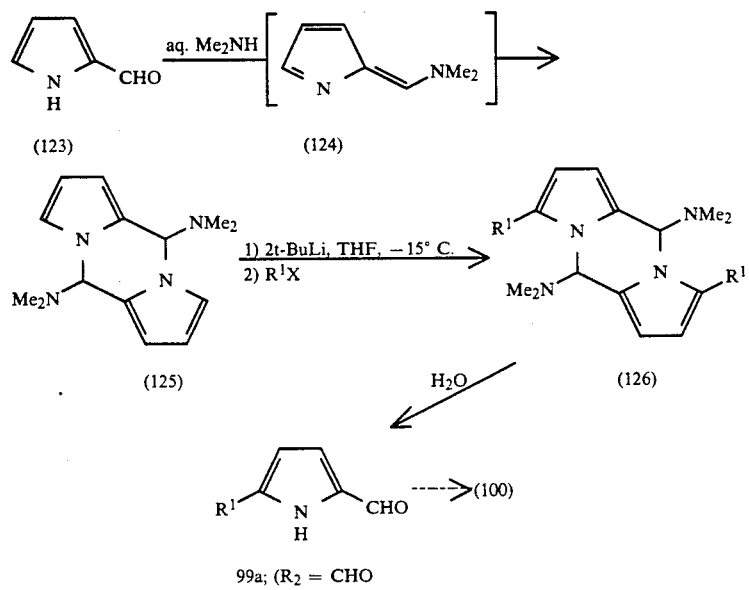

Scheme 23a

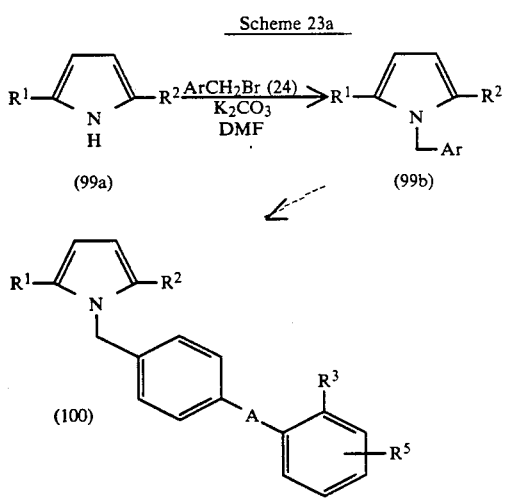

Described herein are general methods for the preparation of specific functional groups on $R^1$ and $R^2$ claimed in this invention. As before, it is understood by those skilled in the art of organic synthesis that all functionality present must be consistent with the chemical transformations proposed.

As shown in Scheme 24, equation a), benzylic heterocycles (125) where $R^1$ or $R^2$=$CH_2OH$ may be converted to the corresponding halide, mesylate or tosylate by a variety of methods familiar to one skilled in the art. Preferably, the alcohol (125) is converted to the chloride (126) using thionyl chloride in an inert solvent at temperatures of 20° C. to the reflux temperature of the solvent.

Chloride (126) may be displaced by a variety of nucleophiles. For example, excess sodium cyanide in DMSO at temperatures of 20° to 100°0 C. may be used to form cyanomethyl derivatives (127). These nitriles (127) may be hydrolyzed to carboxylic acids (128) by treatment with strong acid or alkali. Preferably, treatment with a 1:1 (v/v) mixture of concentrated aqueous hydrochloric acid/glacial acetic acid at reflux temperatures for 2-96 hours or by treatment with 1N sodium hydroxide in an alcohol solvent such as ethanol or ethylene glycol for 2-96 hours at temperatures from 20° C. to reflux can be used. Alternatively, the nitrile group can be hydrolyzed in two steps by first stirring in sulfuric acid to form the amide followed by acidic or basic hydrolysis to furnish the carboxylic acids (128).

These carboxylic acids (128) may be esterified to esters (129) using standard methods, for example, stirring the carboxylic acids (128) with an alcohol in a suitably inert solvent containing hydrogen chloride or similar catalysts, or by first converting the carboxylic acids (128) to the corresponding acid chloride with thionyl chloride or oxalyl chloride followed by treatment with the appropriate alcohol. Carboxylic acids (128) may also be reduced to the corresponding hydroxymethyl compounds (130) using reductants like $LiAlH_4$ or $B_2H_6$, thus constituting an overall homologation for the process (125)+(130).

Alcohol derivatives (125 or 130) may be acylated to give esters (131) by a variety of procedures. As shown in Scheme 24, equation b), acylation can be achieved with 1-3 equivalents of an acyl halide or anhydride in a suitable solvent like diethyl ether or tetrahydrofuran in the presence of a base such as pyridine or triethylamine. Alternatively, such alcohols (125, 130) may be acylated by reaction with a carboxylic acid and dicyclohexylcarbodiimide (DCC) in the presence of a catalytic amount of 4-(N,N-dimethylamino)pyridine (DMAP) via the procedure described by A. Hasmer, *Tetrahedron Lett.* 46, 4475 (1978). Treatment of 125 or 130 with a solution of carboxylic acid anhydride in pyridine optionally with a catalytic amount of DMAP at temperatures of 200–100° C. for 2–48 hours is the preferred method.

Ethers (132) can be prepared from the alcohols (125), as shown in Scheme 24, equation c), by treatment of (125) in a solvent such as DMF or DMSO with potassium t-butoxide or sodium hydride followed by treatment with $R^4L$ at 25° C. for 1–20 hours, where L is a halogen, mesylate or tosylate group. Alternatively, treatment of chlorides (126) with 1–3 equivalents of $R^4OM$ where M is sodium or potassium, for 2–10 hours at 25° C., either in $R^4OH$ as solvent or in a polar solvent such as DMF will also give ethers (132). Such ethers (132) may also be prepared, for example, by heating (125) for 3–15 hours at 60–160° C. in $R^4OH$ containing an inorganic acid such as hydrochloric or sulfuric acids.

As shown by Scheme 24, equation d), amides (133) may be prepared from carboxylic acids (128) through a variety of methods familiar to one skilled in the art and as described previously (Scheme 2).

Scheme 25, equation a), shows how amines (134) may be obtained from chlorides (126) by displacement with ammonia, or through a Gabriel synthesis, or by displacement with sodium azide followed by reduction as described earlier (Scheme 14). Access to homologous amines (134) may be gained by reduction of nitriles (127) with, for example, metal hydride reagents like $LiAlH_4$ or via catalytic hydrogenation. Such amines (134) may be converted to sulfonamides (IU) and carbamates (136), using standard procedures familiar to one skilled in the art.

Scheme 25, equation b), illustrates the preparation of thioethers (137) from chlorides (126) by displacement with the sodium or potassium salt of alkyl mercaptans. Sulfides (137) may be oxidized to the corresponding sulfoxide and sulfone derivatives (138) with a variety of oxidants, for example, hydrogen peroxide, sodium periodate, t-butyl hypochlorite, sodium perborate, or peroxycarboxylic acids, S. Palai, *The Chemistry of Functional Groups, Supplement E*, pt. 1, pp. 539–608, Wiley, New York (1980).

Alternative introduction of sulfur may be achieved by conversion of the hydroxyl group of 139 to thiolacetic acid derivatives (141), J. Y. Gauthier, *Tetrahedron Lett.* 15 (1986), and, subsequently, to mercaptans (142) by hydrolysis as illustrated in Scheme 25, equation c).

Also as shown in Scheme 25, equation c), the hydroxyl group can be converted to its corresponding fluoro compound (140) by various fluorinating agents such as DAST.

The nitriles (127) can be converted into the corresponding tetrazole derivatives (143) by a variety of methods using hydrazoic acid as shown by Scheme 25, equation d). For example, the nitrile can be heated with sodium azide and ammonium chloride in DMF at temperatures between 30° C. and reflux for 1–10 days, J. P. Hurwitz and A. J. Tomson, *J. Org. Chem.*, 26, 3392 (1961). Preferably, the tetrazole is prepared by the 2,3-dipolar cycloaddition of trialkyltin or triaryltin azides to the appropriately substituted nitrile as described previously in Scheme 7.

As shown by Scheme 26, equation a), the hydroxymethyl group of (125) can be oxidized to the corresponding aldehydes (144) using a mild oxidant, such as manganese dioxide or cerric ammonium nitrate. Such aldehydes may undergo typical chain-extensions via the Wittig and Wittig-Horner-Emmons reactions to give alkenyl compounds such as 146 directly or react with Grignard and lithium reagents to give alcohols (145). These alcohols may undergo dehydration to the corresponding alkenyl compounds (146) using standard methods, for example, by first converting such alcohols (145) to the corresponding mesylate, tosylate or halide derivatives followed by elimination using an appropriate base such as DBU, triethylamine, or potassium t-butoxide.

Alternative access to alkenyl-substituted heterocycles may be gained via the corresponding alkyl-heterocycles (147) as illustrated for Scheme 26, equation b). Free-radical bromination of (147) by UV-irradiation for 1–4 hours in the presence of N-bromosuccinimide in an inert solvent such as carbon tetrachloride at 25° C. gives bromides (148). Treatment of these intermediates (148) with an appropriate base such as DBU, triethylamine, or potassium t-butoxide, affords (predominantly or exclusively) the trans-alkenylheterocycles (149). The corresponding cis-alkenyl derivatives (151) may be prepared as described above (for 146) or from the trans-alkenyl compounds (149) by oxidative cleavage with osmium tetroxide and sodium periodate to give aldehydes (150) followed by Wittig chemistry.

Scheme 24

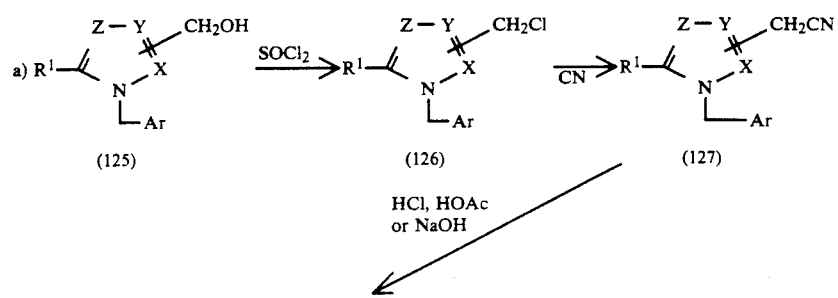

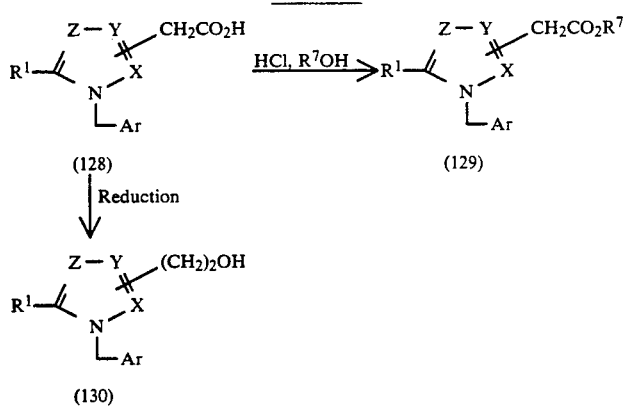
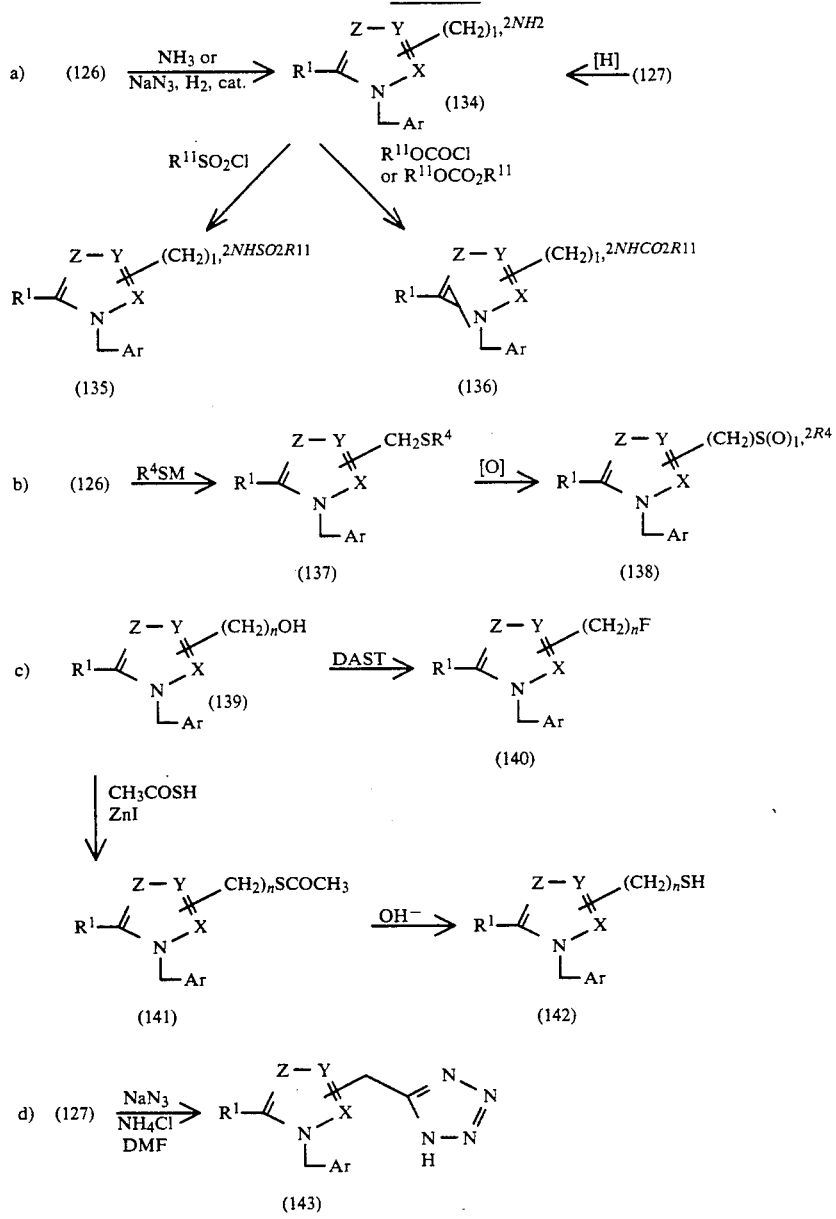

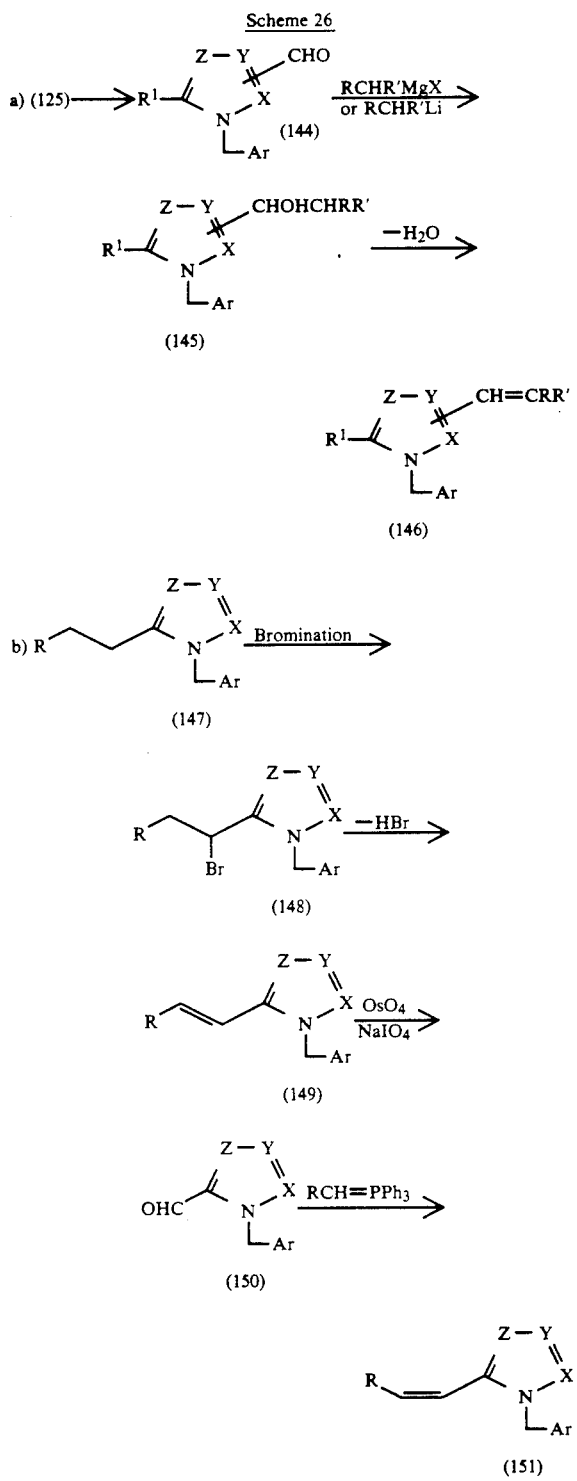

Scheme 26

(145)

(146)

(147)

(148)

(149)

(150)

(151)

Described herein are general methods for the preparation of specific functional groups on $R^1$ and $R^2$ claimed in this invention. As before, it is understood by those skilled in the art of organic synthesis that all functionality present must be consistent with the chemical transformation proposed.

The compounds of this invention and their preparation can be understood further by the following examples, but should not constitute a limitation thereof.

EXAMPLE 1

Part A: Methyl 4'-azidomethylbiphenyl-2-carboxylate

To a solution of methyl 4'-bromomethylbiphenyl-2-carboxylate (5.0 g, 16.4 mmol) in DMF (40 ml) was added sodium azide (2.7 g, 41 mmol). The mixture was stirred overnight at room temperature, filtered, and the filtrate was partitioned between water and ethyl acetate (100 ml). The aqueous phase was extracted once more with ethyl acetate (100 ml) and the combined organic phase was washed with water (3 × 100 ml) and saturated aqueous sodium chloride (100 ml) before being dried (MgSO$_4$), filtered and concentrated to an oily residue (3.9 g) which was used in the subsequent reaction without further purification: NMR (200 MHz; CDCl$_3$,TMS) δ: 7.9–7.2 (m,8H), 4.37 (s,2H), and 3.60 (s,3H).

Part B: 4- and 5-Butyl-1-[(2'-carbo-methoxybiphenyl-4-yl)methyl]-1,2,3-triazoles A solution of methyl 4'-azidomethylbiphenyl-2-carboxylate (2.0 g, 9.7 mmol) and 1-hexyne (10 ml) was refluxed (70–71° C.) for 2 days. Concentration in vacuo gave 3.2 g of a yellow oily residue from which both isomers could be isolated via flash chromatography with neutral alumina (150 g, Activity I; 20% EtOAc/hexanes).

Isolated was 0.58 g of the 4-isomer (high R$_f$) and 0.47 g of the 5-isomer (low R$_f$); NMR (4-isomer; 200 MHz; CDCl$_3$,TMS) δ: 7.86–7.20 (m,9H), 5.55(s,2H), 3.63(s,3H), 2.72 (t,J=7 Hz,2H), 1.69–1.61 (m,2H), 1.43–1.26 (m,2H), 0.92 (t, J=7.5 Hz, 3H)

NMR (5-isomer; 200 MHz; CDCl$_3$, TMS) identical with the 4-isomer except the triplet at 2.72 ppm was shifted to 2.54 ppm.

Part C: 4-Butyl-1-[(2'-carboxybiphenyl-4-yl)methyl]-1,2,3-triazole

To a solution of 480 mg (1.37 mmol) of 4-butyl-1-[(2'-carbomethoxybiphenyl-4-yl)methyl]-1,2,3-triazole in methanol (20 ml) was added 4N NAOH (20 ml). The resulting slurry was stirred while being refluxed for 2–6 hours (or until a homogeneous solution resulted). The methanol was removed by rotary evaporation and the residue was diluted to a volume of 35 ml with water. Titration to pH 4 with dilute HCl gave a sticky precipitate which was extracted into ethyl acetate; the organic layer was dried over MgSO$_4$, filtered and concentrated to leave 438 mg of a white solid; m.p. 90–95° C.

NMR (200 MHz; CDCl$_3$, CD$_3$OD, TMS) δ: 7.93–7.24 (m, 9H), 5.52 (s,2H), 2.69 (t,J=7.5 Hz,2H), 1.67–1.59 (m,2H), 1.42–1.37 (m,2H), 0.92 (t,J=7 Hz,3H).

EXAMPLE 2

5-Butyl-1-[2'-carboxybiphenyl-4-yl)-methyl]-1,2,3-triazole

From 5-butyl-1-[2'-carboxymethylbiphenyl-4-yl)methyl]-1,2,3-triazole (458 mg, 1.3 mmol) was obtained 363 mg of the title compound using the procedure of Example 1, Part C; m.p 50–56° C.

NMR (200 MHz; CDCl$_3$, TMS) δ: 7.96–7.13 (m,9H), 5.53 (s,2H), 2.52 (t,J=7 Hz,2H), 1.60–1.45 (m,2H), 1.40–1.25 (m, 2H), 0.85 (t, J=7 Hz, 3H).

EXAMPLE 3

Part A:

4'-Azidomethyl-2-(1-triphenylmethyltetrazol-5-yl)biphenyl

This compound was prepared according to the procedure of Example 1, Part A. From 4'-bromomethyl-2-(1-triphenylmethyl-2-tetrazol-5-yl)biphenyl (5.0 g, 9 mmol) was obtained 4.5 g of the title compound as a white solid.

NMR (200 MHz; $CDCl_3$,TMS) $\delta$: 7.93−6.88 (m,23H), 4.24 (s,2H).

Part B: 4- and 5-Butyl-1-[2'-(1-tri-phenylmethyl-tetrazol-5-yl)biphenyl-4-yl-methyl]-1,2,3-triazoles These compounds were prepared according to the procedure of Example 1, Part B. From 4'-azidomethyl-2-(1-triphenylmethyltetrazol-5-yl)biphenyl (4.5 g, 8.7 mmol) was obtained 5.4 g of the crude isomers which were purified by chromatography on silica gel (300 g, 50% $Et_2O$/hexanes).

There was obtained 1.81 g of the 4-butyl isomer: NMR (200 MHz, $CDCl_3$, TMS) $\delta$: 8.0−6.87 (m,24H), 5.35 (s,2H), 2.60 (t,J=7.5 Hz,2H), 1.59−1.51 (m,2H), 1.38−1.27 (m, 2H) , 0.89 (t, J=7 Hz, 3H).

There was also obtained 1.49 g of the 5-butyl isomer which displayed a nearly identical NMR with the exception of minor changes in the splitting pattern in the aromatic region and a shift in the triplet at 2.60 ppm to 2.40 ppm.

Part C:
4-Butyl-1-[2'-(1H-tetrazol-yl)-biphenyl-4-yl)methyl-1,2,3-triazoles

To a slurry of 4-butyl-1-[2'-(1-triphenylmethyltetrazol-5-yl)biphenyl-4-yl)methyl-1,2,3-triazole (1.45 g, 2.4 mmol) in water (15 ml) was added dropwise a solution of trifluoroacetic acid in water (1/1, 30 ml) over several minutes. The slurry was further stirred for 30 minutes before being made alkaline with 4N NAOH (50 ml). The mixture was extracted twice with ether (100 ml) and the aqueous phase was acidified to pH 4 with 4N HCl to give a white precipitate which was suction filtered, washed with water and hexanes and dried under vacuum to give 754 mg (87%) of a white solid: NMR (200 MHz; $CDCl_3$k TMS) $\delta$: 7.91-7.00 (m,9H), 5.40 (s,2H), 2.53 (t,J=7 Hz,2H), 1.56−1.48 (m,2H), 1.33−1.22 (m.2H), 0.86 (t,J=7 Hz,3H).

EXAMPLE 4

5-Butyl-1-[2'-(1H-tetrazol-5-yl)biphenyl-4-yl)methyl]-1,2,3-triazole

This compound was obtained using the same procedure of Example 3, Part C.

In this case, acidification of the aqueous phase resulted in a gummy precipitate which could be extracted into ethyl acetate. The organic layer was dried ($MgSO_4$), filtered and concentrated to give the title compound as a white solid. From 5-butyl-1-[2'-(1-triphenylmethyltetrazol-5-yl)biphenyl-4-yl-methyl]-1,2,3-triazole (1.4 g, 2.3 mmol) was obtained 600 mg (71%) of the title compound. NMR (200 MHz; $CDCl_3$, $CD_3OD$,TMS) $\delta$: 7.78−7.06 (m,9H), 5.47 (s,2H), 2.60−2.52 (t,J=8 Hz,2H), 1.65−1.50 (m,2H), 1.41−1.30 (m,2H), 0.91 (t, J=7 Hz, 3H).

The 1,2,3-triazoles listed in Table 1 are examples of compounds of this invention which were prepared or could be prepared by the procedures of Examples 1–4 or by procedures previously described herein.

TABLE 1

1,2,3-TRIAZOLES

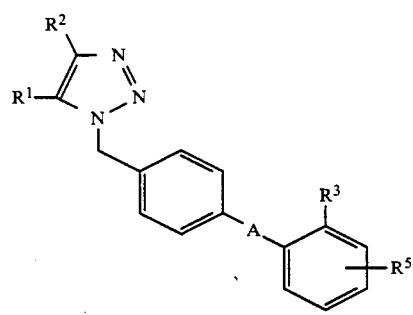

| Ex. No. | $R^1$ | $R^2$ | $R^3$ | $R^5$ | A | m.p.(°C.) |
|---|---|---|---|---|---|---|
| 1 | H | n-butyl | $CO_2H$ | H | Single bond | 90–95 |
| 2 | n-butyl | H | $CO_2H$ | H | Single bond | 50–56 |
| 3 | H | n-butyl | $CN_4H$ | H | Single bond | 133–136 |
| 4 | n-butyl | H | $CN_4H$ | H | Single bond | (Amorphous) |
| 5 | H | $C_2H_5$ | $CO_2H$ | H | Single bond | |
| 6 | $C_2H_5$ | H | $CO_2H$ | H | Single bond | |
| 7 | H | n-propyl | $CO_2H$ | H | Single bond | |
| 8 | n-propyl | H | $CO_2H$ | H | Single | |

TABLE 1-continued 1,2,3-TRIAZOLES

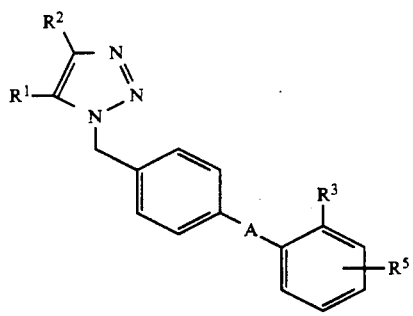

| Ex. No. | $R^1$ | $R^2$ | $R^3$ | $R^5$ | A | m.p.(°C.) |
|---|---|---|---|---|---|---|
| 9 | H | n-$C_5H_{11}$ | $CO_2H$ | H | CO |  |
| 10 | n-$C_5H_{11}$ | H | $CO_2H$ | H | CO |  |
| 11 | H | n-$C_6H_{13}$ | $CO_2H$ | H | CO |  |
| 12 | n-$C_6H_{13}$ | H | $CO_2H$ | H | CO |  |
| 13 | H | CH=$CHCH_3$ | $NHSO_2CF_3$ | H | $OCH_2$ |  |
| 14 | CH=$CHCH_3$ | H | $NHSO_2CF_3$ | H | $OCH_2$ |  |
| 15 | H | CH=$CHCH_2CH_3$ | $NHSO_2CF_3$ | H | $OCH_2$ |  |
| 16 | CH=$CHCH_2CH_3$ | H | $NHSO_2CF_3$ | H | $OCH_2$ |  |
| 17 | H | CH=$CH(CH_2)_2CH_3$ | $NHSO_2CF_3$ | H | Single bond |  |
| 18 | CH=$CH(CH_2)_2CH_3$ | H | $NHSO_2CF_3$ | H | Single bond |  |
| 19 | H | CH=$CH(CH_2)_2CH_3$ | $NHSO_2CF_3$ | H | Single bond |  |
| 20 | CH=$CH(CH_2)_3CH_3$ | H | $NHSO_2CF_3$ | H | Single bond |  |
| 21 | H | C≡$CCH_3$ | $CO_2H$ | H | O |  |
| 22 | C≡$CCH_3$ | H | $CO_2H$ | H | O |  |
| 23 | H | C≡$CCH_2CH_3$ | $CO_2H$ | H | O |  |
| 24 | C≡$CCH_2CH_3$ | H | $CO_2H$ | H | O |  |
| 25 | H | C≡$C(CH_2)_2CH_3$ | $CO_2H$ | H | O |  |
| 26 | C≡$C(CH_2)_2CH_3$ | H | $CO_2H$ | H | O |  |
| 27 | H | C≡$C(CH_2)_3CH_3$ | $CO_2H$ | H | O |  |
| 28 | C≡$C(CH_2)_3CH_3$ | H | $CO_2H$ | H | O |  |
| 29 | H | $CH_2OH$ | $CO_2H$ | H | Single bond |  |
| 30 | $CH_2OH$ | H | $CO_2H$ | H | Single bond |  |
| 31 | H | $(CH_2)_2OCH_3$ | $CO_2H$ | H | Single bond |  |
| 32 | $(CH_2)_2OCH_3$ | H | $CO_2H$ | H | Single bond |  |
| 33 | H | $(CH_2)_3OCH_3$ | $CO_2H$ | H | Single bond |  |
| 34 | $(CH_2)_3OCH_3$ | H | $CO_2H$ | H | Single bond |  |
| 35 | H | $(CH_2)_4OCH_3$ | $CO_2H$ | H | Single bond |  |
| 36 | $(CH_2)_4OCH_3$ | H | $CO_2H$ | H | Single bond |  |
| 37 | H | $(CH_2)_5OCH_3$ | $CO_2H$ | H | Single bond |  |
| 38 | $(CH_2)_5OCH_3$ | H | $CO_2H$ | H | Single bond |  |
| 39 | H | $(CH_2)_6OCH_3$ | $CO_2H$ | H | Single bond |  |
| 40 | $(CH_2)_6OCH_3$ | H | $CO_2H$ | H | Single bond |  |
| 41 | H | $CH_2OCH_2CH_3$ | $CO_2H$ | H | Single bond |  |
| 42 | $CH_2OCH_2CH_3$ | H | $CO_2H$ | H | Single bond |  |
| 43 | H | $CH_2O(CH_2)_2CH_3$ | $CO_2H$ | H | Single bond |  |
| 44 | $CH_2O(CH_2)_2CH_3$ | H | $CO_2H$ | H | Single bond |  |
| 45 | H | $CH_2O(CH_2)_3CH_3$ | $CO_2H$ | H | Single bond |  |
| 46 | $CH_2O(CH_2)_3CH_3$ | H | $CO_2H$ | H | Single bond |  |
| 47 | H | n-propyl | $CO_2H$ | $CH_3$ | NHCO |  |

TABLE 1-continued

1,2,3-TRIAZOLES

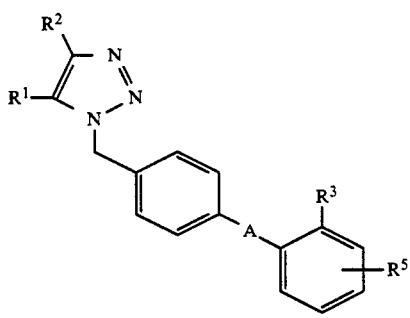

| Ex. No. | R¹ | R² | R³ | R⁵ | A | m.p.(°C.) |
|---|---|---|---|---|---|---|
| 48 | n-propyl | H | CO₂H | CH₃ | NHCO | |
| 49 | H | n-propyl | CO₂H | Et | NHCO | |
| 50 | n-propyl | H | CO₂H | Et | NHCO | |
| 51 | H | n-propyl | CO₂H | i-propyl | NHCO | |
| 52 | n-propyl | H | CO₂H | i-propyl | NHCO | |
| 53 | H | n-propyl | CO₂H | s-butyl | NHCO | |
| 54 | n-propyl | H | CO₂H | s-butyl | NHCO | |
| 55 | H | n-propyl | CO₂H | OCH₃ | NHCO | |
| 56 | n-propyl | H | CO₂H | OCH₃ | NHCO | |
| 57 | H | n-propyl | CO₂H | F | NHCO | |
| 58 | n-propyl | H | CO₂H | F | NHCO | |
| 59 | H | n-propyl | NHSO₂CF₃ | Cl | NHCO | |
| 60 | n-propyl | H | NHSO₂CF₃ | Cl | NHCO | |
| 61 | H | n-propyl | NHSO₂CF₃ | Br | NHCO | |
| 62 | n-propyl | H | NHSO₂CF₃ | Br | NHCO | |
| 63 | H | n-propyl | NHSO₂CF₃ | I | NHCO | |
| 64 | n-propyl | H | NHSO₂CF₃ | I | NHCO | |
| 65 | H | n-propyl | CO₂H | NO₂ | NHCO | |
| 66 | n-propyl | H | CO₂H | NO₂ | NHCO | |

EXAMPLE 67

Part A: Methyl 4'-aminomethylbiphenyl-2-carboxylatehydrochloride

A mixture of methyl 4'-azidomethylbiphenyl-2-carboxylate (111 g, 0.42 mol; see Part A, Ex. 1) and 5% Pd on carbon (20 g) in methanol (1 L) was placed in a Parr apparatus under 50 psi H₂ atmosphere overnight at room temperature. The mixture was filtered through Celite and the filtrate was concentrated to a yellow viscous residue (88 g). This crude amine was dissolved in ethyl acetate (500 ml), cooled to 0° C. and titrated with a 0° C. solution of ethyl acetate saturated with hydrogen chloride to completion of precipitation (ca. 110 ml).

The precipitate was collected by vacuum filtration and was washed with ethyl acetate, hexanes and dried under vacuum to give 48.5 g (42%); m.p. 200–203° C.

NMR (200 MHz; CDCl₃, CD₃OD, TMS) δ: 7.90−7.25 (m,8H), 4.15 (s,2H), 4.10−3.80 (br,3H; exchanges D₂O), 3.55 (s,3H).

The corresponding nitrile was prepared similarly. From 4'-azidomethylbiphenyl-2-nitrile (22.8 g, 97.3 mmol); see Ex. 1, Part A) was obtained the corresponding amine hydrochloride (15.4 g; 68%); m.p. 230° C. (dec.).

NMR (200 MHz; CDCl₃, CD₃OD, TMS) 7.81−7.47 (m,8H), 4.19 (s,2H), 4.0 (br,3H; exchanges D₂O).

Part B: 3-Butyl-5-methoxymethyl-4-[(2'-carbomethoxy-biphenyl-4-yl)methyl]-1.2.4-triazole A solution of triethyl orthovalerate (3.3 g, 16.2 mmol), methoxyacetyl hydrazide (1.7 g, 16.2 mmol) and DBU (1.8 g, 11.9 mmol) in xylenes (50 ml) was refluxed for 2 hrs and cooled to room temperature, whereupon methyl 4'-aminomethylbiphenyl-2-carboxylate hydrochloride (3.0 g, 10.0 mmol) was added. The reaction was brought back to reflux for a further 24 h. After being cooled to room temperature, the mixture was diluted with ethyl acetate (150 ml) and washed with water (100 ml), saturated aqueous sodium chloride and dried (MgSO₄). Filtration and evaporation of solvents gave 4.8 g of a yellow oil which was purified by flash chromatography on silica gel (150 g, 5–10% EtOAc/hexane) to afford 3.4 g (78%) of the title compound as a yellow viscous oil.

NMR (200 MHz, CDCl₃, TMS) δ: 7.87–7.05 (m,8H), 5.25 (s,2H), 4.56 (s,2H), 3.67 (s,3H), 3.37 (s,3H), 2.68 (t,J=8 Hz,2H), 1.73 (m,2H), 1.38 (m,2H), 0.90 (t, J=9 Hz, 3H).

Part C: 3-Butyl-5-methoxymethyl-4-[(2'-carboxybiphenyl-4-yl)methyl]-1,2,4-triazole Hydrolysis of the 1,2,4-triazole esters was carried out in the same fashion as for the 1,2,3-triazoles as described in Example 1, Part C.

From 3-butyl-5-methoxymethyl-4-[(2'-carbomethoxybiphenyl-4-yl)methyl]-1,2,4-triazole (273 mg, 0.69 mmol) was obtained 218 mg (83%) of the title compound as a white solid; m.p. 229-232° C. (dec.).

NMR (200 MHz,CDCl₃,CD₃OD,TMS) δ: 7.90−7.04 (m,8H), 5.24 (s,2H), 4.50 (s,2H), 3.34 (s,3H), 2.69 (t,J=8 Hz,2H), 1.67 (m,2H), 1.37 (m,2H), 0.90 (t, J=7 Hz, 3H).

EXAMPLE 68

Part A: 3-Butyl-4-[(2'-carbomethoxybiphenyl-4-yl)-methyl]-1,2,4-triazole triazole This compound was prepared according to the method described in Example 67, Part B.

From triethyl orthoformate (2.7 ml, 16.2 mmol), valeryl hydrazide (1.9 g 16.2 mmol), DBU (1.8 ml, 11.9 mmol) and methyl 4'-aminomethylbiphenyl-2-carboxylate hydrochloride (3.0 g, 10.8 mmol) in refluxing xylenes (50 ml) was obtained 2.14 g (56%) of the title compound as a pale yellow oil following flash chromatography.

NMR (200 MHz, CDCl₃, TMS) δ: 8.10 (s,1H), 7.89−7.11 (m,8H), 5.14 (s,2H), 3.66 (s,3H), 2.71 (t,J=7 Hz,2H), 1.78−1.66 (m,2H), 1.46−1.34 (m,2H), 0.92 (t,J=7 Hz,3H).

Part B:
3-Butyl-4-[(2'-carboxybiphenyl-4-yl)methyl]-1,2,4-triazole

This compound was prepared according to the method described for Example 1, Part C.

From 3-butyl-4-[(2'-carbomethoxybiphenyl-4-yl)-methyl]-1,2,4-triazole (308 mg, 0.88 mmol) was obtained 219 mg (74%) of the title compound as a white solid; m.p. 199-201° C. (dec.).

NMR (200 MHz;CDCl₃, CD₃OD,TMS) δ: 8.10 (s,1H), 7.95−7.12 (m,8H), 5.11 (s,2H), 2.72 (t,J=8HZ,2H), 1.72−1.68 (m,2H), 0.92 (t,J=7 Hz,3H).

EXAMPLE 69

Part A:
3-Methoxymethyl-5-propyl-4-[(2'-carbomethoxy-biphenyl-4-yl)methyl]-1.2.4-triazole This compound was prepared according to the method described for Example 67, Part B.

From triethyl orthobutyrate (3.1 g, 16.2 mmol) methoxyacetyl hydrazide (1.7 g, 16.2 mmol) DBU (1.8 ml, 11.9 mmol) and methyl 4'-aminomethylbiphenyl-2-carboxylate hydrochloride (3.0 g, 10.8 mmol) in refluxing xylenes (50 ml) was obtained 2.3 g (56%) of the title compound as a colorless oil following flash chromatography.

NMR (200 MHz;CDCl₃, TMS) δ: 7.88−7.04 (m,8H), 5.25 (s,2H), 4.56 (s,2H), 3.65 (s,3H), 3.34 (s,3H), 2.66 (t,J=7 Hz,2H), 1.78 (m,2H), 0.98 (t,J=7 Hz,3H).

Part B:
3-Methoxymethyl-5-propyl-4-[(2'-carboxybiphenyl-4-yl)methyl]-1.2.4-triazole This compound was prepared according to Example 1, Part C.

From 3-methoxymethyl-5-propyl-4-[(2'-carboxybiphenyl-4-yl)methyl]-1,2,4-triazole (2.1 g, 5.5 mmol) was obtained 1.84 g (91%) of the title compound as a white solid, m.p. 225-227.5° C. (dec.)

NMR (200 MHz; CDCl₃, CD₃OD,TMS) δ: 7.93−7.03 (m,8H), 5.24 (s,2H), 4.51 (s,2H), 3.33 (s,3H), 2.65 (t,J=7 Hz,2H), 1.73 (m,2H), 0.96 (t,J=7 Hz,3H).

EXAMPLE 70

Part A:
3-Ethyl-5-methoxymethyl-4-[(2'-carbomethoxy-biphenyl-4-yl)methyl]-1.2,,4-triazole This compound was prepared according to Example 67, Part B.

From triethyl orthopropionate (2.86 g, 16.2 mmol), methoxyacetylhydrazide (1.7 g, 16.2 mmol), DBU (1.8 ml, 11.9 mmol) and methyl 4'-aminomethylbiphenyl-2-carboxylate hydrochloride (3.0 g, 10.8 mmol) in refluxing xylenes (50 ml) was obtained 2.4 g (60%) of the title compound as a pale yellow oil following flash chromatography.

NMR (200 MHz, CDCl₃, TMS) δ: 7.88−7.05 (m,8H), 5.24 (s,2H), 4.58 (s,2H), 3.65 (s,3H), 3.35 (s,3H), 2.67 (q,J=7 Hz,2H), 1.32 (t,J=7 Hz,3H).

Part B:
3-Ethyl-5-methoxymethyl-4-[(2'-carboxybiphenyl-4-yl)methyl]-1,2,4-triazole From 3-ethyl-5-methoxymethyl-4-[(2'-carbomethoxybiphenyl-4-yl)methyl]-1,2,4-triazole (2.2 g, 6.0 mmol) was obtained 1.81 g (86%) of the title compound as a white solid; m.p. 234-235.5° C. (dec.)

NMR (200 MHz;CDCl₃, CD₃OD,TMS) δ: 7.93−7.04 (m,8H), 5.24 (s,2H), 4.53 (s,2H), 3.34 (s,3H), 2.69 (q,J=7 Hz,2H), 1.29 (t,J=7 Hz,3H).

EXAMPLE 71

Part A:
3,5-Dibutyl-4-[(2'-carbomethoxybiphenyl-4-yl)methyl]-1,2,4-triazole

This compound was prepared according to the methods described for Example 67, Part B.

From triethyl orthovalerate (3.3 g, 16.2 mmol), valeryl hydrazide (1.9 g, 16.2 mmol), DBU (1.8 ml, 11.9 mmol) and methyl 4'-aminomethylbiphenyl-2-carboxylate (3.0 g, 10.8 mmol) in refluxing xylenes (50 ml) was obtained 2.5 g (57%) of the title compound as a pale yellow oil.

NMR (200 MHz;CDCl₃, TMS) δ: 7.88-6.98 (m,8H), 5.11 (s,2H), 3.65 (s,3H), 2.66 (t,J=7 Hz,4H), 1.79−1.63 (m,4H), 1.48−1.33 (m,4H), 0.89 (t,J=7 Hz,6H).

Part B:
3,5-Dibutyl-4-[(2'-carboxybiphenyl-4-yl)methyl]-1,2,4-triazole

This compound was prepared according to the methods described for Example 1, Part C.

From 3,5-dibutyl-4-[(2'-carbomethoxybiphenyl-4-yl)methyl]-1,2,4-triazole (2,4 g, 5.92 mmol) was obtained 1.88 g (81%) of the title compound as a white solid; m.p. 207-209° C.

NMR (200 MHz;CDCl₃, CD₃OD,TMS) δ: 7.93-6.96 (m,8H), 5.12 (s,2H), 4.06 (s,2H), 2.66 (t,J=7 Hz,4H), 1.74−1.59 (m,4H), 1.45−1.27 (m,4H), 0.89 (t,J=7 Hz,6H).

EXAMPLE 72

Part A:
3-Methoxymethyl-5-propyl-4-[(21-cyanobiphenyl-4-yl)methyl]-1,2,4-triazole This compound was prepared according to the methods described for Example 67, Part B.

From triethyl orthobutyrate (2.3 g, 12.3 mmol) methoxyacetyl hydrazide (1.4 g, 12.3 mmol), DBU (1.4 ml, 8.9 mmol) and 4'-aminomethylbiphenyl-2-nitrile (2.0 g, 8.2 mmol) in refluxing xylenes (50 ml) was obtained 1.6 g (57%) of the title compound, as a viscous oil which slowly crystallized upon standing at room temperature.

NMR (200 MHz;CDCl$_3$, TMS) δ: 7.80−7.12 (m,8H), 5.28 (s,2H), 4.56 (s,2H), 3.34 (s,3H), 2.65 (t,J=7 Hz,2H), 1.78 (m,2H), 0.99 (t,J=7 Hz,3H).

Part B:
3-Methoxymethyl-5-propyl-4-[(2'-(1H-tetrazol-5-yl)biphenyl-4-yl)methyl]-1,2,4-triazole To a solution of 3-methoxymethyl-5-propyl-4-[(2'-cyanobiphenyl-4-yl)methyl]-1,2,4-triazole (1.5 g, 4.33 mmol) in DMF (35 ml) was added sodium azide (NaN$_3$, 0.84 g, 13 mmol) and ammonium chloride (NH$_4$Cl, 0.69 g, 13 mmol). The mixture was stirred at 100° C. for four days whereupon an additional 0.3 g NaN$_3$ and 0.23 g NH$_4$Cl were added. Stirring was continued 2 days further at 100° C. The solvent was removed (rotary evaporation) and the residue was partitioned between ethyl acetate and water (100 ml ea). The organic phase was dried (MgSO$_4$), filtered and concentrated to a viscous light brown oil (1.5 g) which was purified by flash chromatography on silica gel to give 350 mg (21%) of an off-white solid; m.p. 201–205° C. (dec.)

NMR (200 MHz;CDCl$_3$, CD$_3$OD,TMS) δ:, 7.75−6.93 (m,8H), 5.19 (s,2H), 4.47 (s,2H), 3.31 (s,3H), 2.62 (t,J=7 Hz,2H), 1.78−1.66 (m,2H), 0.96 (t,J=7 Hz,3H).

Table 2 lists examples of 1,2,4-triazoles of this invention which were prepared or could be prepared by the procedures of examples 67–72 or by procedures previously described.

TABLE 2

1,2,4-TRIAZOLES

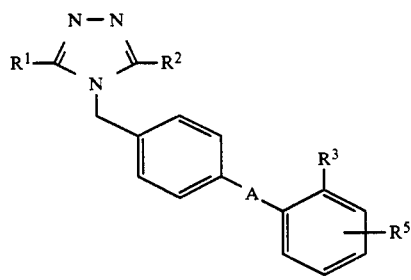

| Ex. No. | R$^1$ | R$^2$ | R$^3$ | R$^5$ | A | m.p.(°C.) |
|---|---|---|---|---|---|---|
| 67 | n-butyl | CH$_2$OCH$_3$ | CO$_2$H | H | Single bond | 229–231 (dec.) |
| 68 | n-butyl | H | CO$_2$H | H | Single bond | 199–201 (dec.) |
| 69 | n-propyl | CH$_2$OCH$_3$ | CO$_2$H | H | Single bond | 225–227.5 (dec.) |
| 70 | C$_2$H$_5$ | CH$_2$OCH$_3$ | CO$_2$H | H | Single bond | 234–235.5 (dec.) |
| 71 | n-butyl | n-butyl | CO$_2$H | H | Single bond | 207–209 (dec.) |
| 72 | n-propyl | CH$_2$OCH$_3$ | CN$_4$H | H | Single bond | 201–205 (dec.) |
| 73 | n-propyl | CH$_2$OH | CN$_4$H | H | Single bond | |
| 74 | n-propyl | CHO | CN$_4$H | H | Single bond | |
| 75 | n-propyl | CO$_2$CH$_3$ | CN$_4$H | H | Single bond | |
| 76 | n-propyl | CO$_2$C$_2$H$_5$ | CN$_4$H | H | Single bond | |
| 77 | n-propyl | CO$_2$-n-C$_3$H$_7$ | CN$_4$H | H | Single bond | |
| 78 | n-propyl | CO$_2$-n-C$_4$H$_9$ | CN$_4$H | H | Single bond | |
| 79 | n-propyl | CO$_2$-n-C$_5$H$_{11}$ | CN$_4$H | H | Single bond | |
| 80 | n-propyl | CO$_2$-c-C$_3$H$_5$ | CN$_4$H | H | Single bond | |
| 81 | n-propyl | CO$_2$-c-C$_4$H$_7$ | CN$_4$H | H | Single bond | |
| 82 | n-propyl | CO$_2$-c-C$_5$H$_9$ | CN$_4$H | H | Single bond | |
| 83 | n-propyl | CO$_2$-c-C$_6$H$_{11}$ | CN$_4$H | H | Single bond | |
| 84 | n-propyl | CO$_2$Ph | CN$_4$H | H | Single bond | |
| 85 | n-propyl | CO$_2$CH$_2$Ph | CN$_4$H | H | Single bond | |
| 86 | n-propyl | CH$_2$COPh | CO$_2$H | H | Single bond | |
| 87 | n-propyl | CH$_2$COCH$_2$Ph | CO$_2$H | H | Single bond | |
| 88 | n-propyl | CH$_2$CO(CH$_2$)$_2$Ph | CO$_2$H | H | Single bond | |
| 89 | n-propyl | CH$_2$CO(CH$_2$)$_3$Ph | CO$_2$H | H | Single bond | |
| 90 | n-propyl | (CH$_2$)$_4$COCH$_2$Ph | CO$_2$H | H | Single bond | |
| 91 | n-propyl | (CH$_2$)$_5$COCH$_2$Ph | CO$_2$H | H | Single bond | |
| 92 | n-propyl | (CH$_2$)$_6$COCH$_2$Ph | CO$_2$H | H | Single bond | |
| 93 | n-propyl | CONH$_2$ | CO$_2$H | H | Single bond | |
| 94 | n-propyl | CONHCH$_3$ | CO$_2$H | H | Single bond | |
| 95 | n-propyl | CON(CH$_3$)$_2$ | CO$_2$H | H | Single bond | |
| 96 | n-propyl | CONHEt | CO$_2$H | H | Single bond | |
| 97 | n-propyl | CONH-n-Pr | CO$_2$H | H | Single bond | |
| 98 | n-propyl | CONH-n-Bu | CO$_2$H | H | Single bond | |
| 99 | n-propyl | CONHPh | CO$_2$H | H | Single bond | |
| 100 | n-propyl | CONHCH$_2$Ph | CO$_2$H | H | Single bond | |

TABLE 2-continued
1,2,4-TRIAZOLES

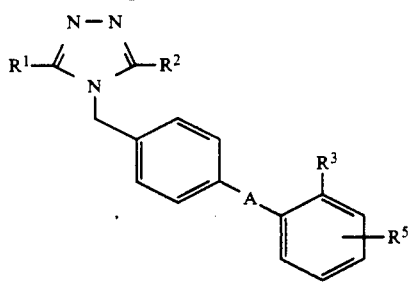

| Ex. No. | R[1] | R[2] | R[3] | R[5] | A | m.p.(°C.) |
|---|---|---|---|---|---|---|
| 101 | n-propyl | CON(pyrrolidine) | CO$_2$H | H | Single bond | |
| 102 | n-propyl | CON(piperidine) | CO$_2$H | H | Single bond | |
| 103 | n-propyl | CON(morpholine, O) | CO$_2$H | H | Single bond | |
| 104 | n-propyl | CON(piperazine, NH) | CO$_2$H | H | Single bond | |
| 105 | n-propyl | CON(piperazine, NCH$_3$) | CO$_2$H | H | Single bond | |
| 106 | n-propyl | CON(piperazine, N—Et) | CO$_2$H | H | Single bond | |
| 107 | n-propyl | CON(piperazine, N-n-Pr) | CO$_2$H | H | Single bond | |
| 108 | n-propyl | CON(piperazine, N-n-Bu) | CO$_2$H | H | Single bond | |
| 109 | n-propyl | CON(piperazine, N—Ph) | CO$_2$H | H | Single bond | |
| 110 | n-propyl | CH$_2$OC(=O)CH$_3$ | CN$_4$H | H | Single bond | |
| 111 | n-propyl | CH$_2$SCH$_3$ | CO$_2$H | H | Single bond | |
| 112 | n-propyl | CH$_2$S(=O)CH$_3$ | CO$_2$H | H | Single bond | |

TABLE 2-continued 1,2,4-TRIAZOLES

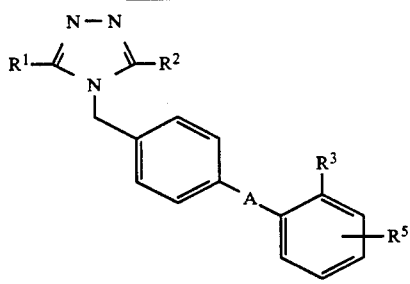

| Ex. No. | $R^1$ | $R^2$ | $R^3$ | $R^5$ | A | m.p.(°C.) |
|---|---|---|---|---|---|---|
| 113 | n-propyl | CH$_2$S(O)$_2$CH$_3$ | CO$_2$H | H | Single bond | |
| 114 | n-propyl | CH=CHCH$_2$OH | CO$_2$H | H | Single bond | |
| 115 | n-propyl | CH=CHCH$_2$OCH$_3$ | CO$_2$H | H | Single bond | |
| 116 | n-propyl | CH=CHCH$_2$OC$_2$H$_5$ | CO$_2$H | H | Single bond | |
| 117 | n-propyl | CH=CHCH$_2$O-n-C$_3$H$_7$ | CO$_2$H | H | Single bond | |
| 118 | n-propyl | CH=CHCH$_2$O-n-C$_4$H$_9$ | CO$_2$H | H | Single bond | |
| 119 | n-propyl | CH=CHCH$_2$OCH(O) | CO$_2$H | H | Single bond | |
| 120 | n-propyl | CH=CHCH$_2$OC(O)CH$_3$ | CO$_2$H | H | Single bond | |
| 121 | n-propyl | CH=CHCH$_2$OC(O)C$_2$H$_5$ | CO$_2$H | H | Single bond | |
| 122 | n-propyl | CH=CHCH$_2$OC(O)-n-C$_3$H$_7$ | CO$_2$H | H | Single bond | |
| 123 | n-propyl | CH=CHCH$_2$OC(O)-n-C$_4$H$_9$ | CO$_2$H | H | Single bond | |
| 124 | n-propyl | CH=CHC(O)CH$_3$ | CO$_2$H | H | Single bond | |
| 125 | n-propyl | CO$_2$NHCO$_2$CH$_3$ | CO$_2$H | H | Single bond | |
| 126 | n-propyl | CH$_2$NHCO$_2$C$_2$H$_5$ | CO$_2$H | H | Single bond | |
| 127 | n-propyl | CH$_2$NHCO$_2$-n-C$_3$H$_7$ | CO$_2$H | H | Single bond | |
| 128 | n-propyl | CH$_2$NHCO$_2$-n-C$_4$H$_9$ | CO$_2$H | H | Single bond | |
| 129 | n-propyl | CH$_2$NHCO$_2$-n-C$_5$H$_{11}$ | CO$_2$H | H | Single bond | |
| 130 | n-propyl | CH$_2$NHCO$_2$-n-C$_6$H$_{13}$ | CO$_2$H | H | Single bond | |
| 131 | n-propyl | CH$_2$NHCO$_2$CH$_2$Ph | CO$_2$H | H | Single bond | |
| 132 | n-propyl | CH$_2$NHCO$_2$CF$_3$ | CO$_2$H | H | Single bond | |
| 133 | n-propyl | CH$_2$NHSO$_2$CH$_3$ | CO$_2$H | H | Single bond | |
| 134 | n-propyl | CH$_2$NHSO$_2$CF$_3$ | CO$_2$H | H | Single bond | |
| 135 | n-propyl | CH$_2$NHSO$_2$C$_2$F$_5$ | CO$_2$H | H | Single bond | |
| 136 | n-propyl | CH$_2$NHSO$_2$-n-C$_3$F$_7$ | CO$_2$H | H | Single bond | |
| 137 | n-propyl | CH$_2$NHSO$_2$-n-C$_4$F$_9$ | CO$_2$H | H | Single bond | |
| 138 | n-propyl | CH$_2$NHSO$_2$-n-C$_5$F$_{11}$ | CO$_2$H | H | Single bond | |
| 139 | n-propyl | CH$_2$NHSO$_2$-n-C$_6$F$_{13}$ | CO$_2$H | H | Single bond | |
| 140 | n-propyl | CH$_2$NHSO$_2$CH$_2$Ph | CO$_2$H | H | Single bond | |
| 141 | n-propyl | CH$_2$F | CO$_2$H | H | Single bond | |
| 142 | n-propyl | CH$_2$CN$_4$H | CO$_2$H | H | Single bond | |
| 143 | n-propyl | CH$_2$NHCO$_2$Ph | CO$_2$H | H | Single bond | |
| 144 | n-propyl | CH$_2$NHCO$_2$(CH$_2$)$_2$Ph | CO$_2$H | H | Single bond | |
| 145 | n-propyl | CH$_2$NHCO$_2$(CH$_2$)$_3$Ph | CO$_2$H | H | Single bond | |
| 146 | n-propyl | CH$_2$OCH$_3$ | CO$_2$H | NO$_2$ | NHCO | |
| 147 | n-propyl | CH$_2$OCH$_3$ | CO$_2$H | OCH$_3$ | NHCO | |
| 148 | n-propyl | CH$_2$OCH$_3$ | CO$_2$H | CH$_3$ | NHCO | |
| 149 | n-propyl | CO$_2$H | CO$_2$H | H | Single bond | |
| 150 | CH$_2$OH | H | CO$_2$H | H | Single bond | |
| 151 | CH$_2$OH | n-C$_5$H$_{11}$ | CO$_2$H | H | Single bond | |
| 152 | CH$_2$OH | n-C$_6$H$_{13}$ | CO$_2$H | F | NHCO | |
| 153 | (CH$_2$)$_2$OCH$_3$ | n-propyl | CO$_2$H | H | Single bond | |

TABLE 2-continued
1,2,4-TRIAZOLES

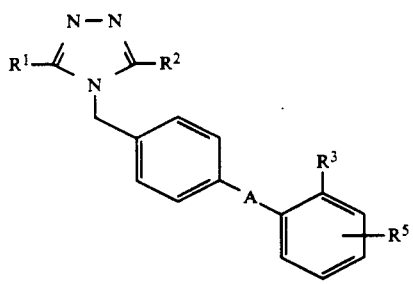

| Ex. No. | R¹ | R² | R³ | R⁵ | A | m.p.(°C.) |
|---|---|---|---|---|---|---|
| 154 | (CH₂)₃OCH₃ | n-propyl | CO₂H | H | Single bond | |
| 155 | (CH₂)₄OCH₃ | n-propyl | CO₂H | Cl | NHCO | |
| 156 | (CH₂)₅OCH₃ | n-propyl | CO₂H | Br | NHCO | |
| 157 | (CH₂)₆OCH₃ | n-propyl | NHSO₂CF₃ | I | NHCO | |
| 158 | CH₂OCH₂CH₃ | n-propyl | CO₂H | H | O | |
| 159 | CH₂O(CH₂)₂CH₃ | n-propyl | CO₂H | H | O | |
| 160 | CH₂O(CH₂)₃CH₃ | n-propyl | CO₂H | H | O | |
| 161 | CH₂OCH₃ | CH=CHCH₃ | CO₂H | H | CO | |
| 162 | CH₂OCH₃ | CH=CHCH₂CH₃ | CO₂H | H | CO | |
| 163 | CH₂OCH₃ | CH=CH(CH₂)₂CH₃ | CO₂H | H | CO | |
| 164 | CH₂OCH₃ | CH=CH(CH₂)₃CH₃ | CO₂H | H | CO | |
| 165 | CH₂OCH₃ | C≡CCH₃ | CO₂H | H | CO | |
| 166 | CH₂OCH₃ | C≡CCH₂CH₃ | CO₂H | H | CO | |
| 167 | CH₂OCH₃ | C≡C(CH₂)₂CH₃ | CO₂H | H | CO | |
| 168 | CH₂OCH₃ | C≡C(CH₂)₃CH₃ | CO₂H | H | CO | |
| 169 | n-propyl | CO₂H | CO₂H | H | OCH₂ | |

EXAMPLE 170

Part A: 1-Methoxy-2,4-octadione

To a solution of methyl methoxyacetate (20.8 g, 200 mmol) in toluene (250 ml) was added sodium ethoxide (7.5 g, 110 mmol) followed by 2-hexanone (10 g, 100 mmol). The mixture was stirred overnight at room temperature, quenched with water (-100 ml) and acidified to about pH 5 with glacial acetic acid. The aqueous phase was extracted with ethyl acetate (100 ml) and the combined organic phases were washed with saturated brine before being dried (MgSO₄), filtered and concentrated under medium vacuum (20 mm Hg, rotary evaporator) to leave 15.8 g of a brown liquid. Fractional distillation at 4 mm Hg gave the purified product, b.p. 111–116° C. The yield was 7.2 g (42%) of a clear liquid.

NMR (200 MHz;CDCl₃, TMS) δ: 5.79 (s,1H), 3.99 (s,2H), 3.43 (s,3H), 2.33 (t,J=7 Hz,2H), 1.65–1.54 (m,2H), 1.42–1.27 (m,2H), 0.93 (t,J=7 Hz,3H).

Part B: 3(5)-Butyl-5(3)-methoxymethylpyrazole

To a solution of 1-methoxy-2,4-octadione (1.9 g, 11.0 mmol) in ethanol (20 ml) was added dropwise and with stirring a solution of hydrazine hydrate (0.8 g, 16.5 mmol) in ethanol (10 ml). Following 1 hour at room temperature, the mixture was refluxed 1 hour before being concentrated to an oily residue. This crude product was dissolved in CH₂Cl₂, dried over MgSO₄, filtered and concentrated to leave 1.69 g (91%) of the title compound as a yellow-orange oil, used in subsequent transformations without further purification.

NMR (200 MHz;CDCl₃, TMS) δ: 6.07 (s,1H), 4.47 (s,2H), 3.39 (s,3H), 2.64 (t,J=7 Hz,2H), 1.63 (m,2H), 1.39 (m, 2H) , 0.92 (t, 7 Hz, 3H)

Part C: 3-Methoxymethyl-5-butyl- and 5-methoxymethyl-3-butyl-1-[(2'-carbomethoxybiphenyl-4-yl)methyl]pyrazoles To a solution of 3(5)-butyl-5(3)-methoxymethylpyrazole (0.86 g, 5.1 mmol) in DMF (30 ml) was added NaH (141 mg, 6.2 mmol). The mixture was stirred 15 minutes and methyl 4'-bromomethylbiphenyl-2-carboxylate (1.87 g, 6.1 mmol) was added as a solution in DMF (5 ml). The mixture was stirred overnight at room temperature before being poured into a separatory funnel containing ethyl acetate (100 ml) and water (100 ml). The aqueous phase was extracted once more with ethyl acetate and the combined organic phase was washed thrice with water (100 ml) before being dried (MgSO₄), filtered and concentrated to leave 1.6 g of the crude product as brown oil. The isomers were separated by flash chromatography on silica gel (65 g, 20% EtOAc/hexanes).

Isolated was 0.6 g of the 5-methoxymethyl-3-butyl isomer (high R_f) and 0.8 g of the 3-methoxymethyl-5-butyl isomer (low R_f).

NMR (high R_f isomer; 200 MHz;CDCl₃,TMS) δ: 7.82–7.12 (m,8H), 6.08 (s,1H), 5.37 (s,2H), 4.33 (s,2H), 3.62 (s,3H), 3.29 (s,3H), 2.63 (t,J=7 Hz,2H), 1.62 (m,2H), 1.39 (m, 2H) , 0.93 (t, J=7 Hz, 3H).

NMR (low R_f isomer; 200 MHz;CDCl₃, TMS) δ: 7.82–7.06 (m,8H), 6.13 (s,1H), 5.32 (s,2H), 4.46 (s,2H), 3.61 (s,3H), 3.41 (s,3H), 2.51 (t,J=7 Hz,2H), 1.56 (m,2H), 1.33 (m,2H), 0.88 (t,J=7 Hz,3H).

Part D: 5-Methoxymethyl-3-butyl-1-[(2'-carboxybiphenyl-4-yl)methyl]pyrazole

Hydrolysis of this ester was effected via the method described in Example 1, Part C.

From 5-methoxymethyl-3-butyl-1-[(2'-carbomethoxybiphenyl-4-yl)methyl]pyrazole (500 mg, 1.28 mmol) was obtained 390 mg (80%) of the corresponding title compound as a light yellow powder; m.p. 129-134° C.

NMR (200 MHz;CDCl$_3$, TMS) δ: 7.93-7.10 (m,8H), 6.04 (s,1H), 5.15 (s,2H), 4.31 (s,2H), 3.28 (s,3H), 2.66 (t,J=7 Hz,2H), 1.65-1.53 (m,2H), 1.42-1.31 (m,2H), 0.92 (t, J=7 Hz, 3H).

EXAMPLE 171

3-Methoxymethyl-5-butyl-1-[(2'-carboxybiphenyl-4-yl)methyl]-pyrazole

Hydrolysis was performed in the same fashion as in Example 1, Part C.

From 3-methoxymethyl-5-butyl-1-[(2'-carbomethoxybiphenyl-4-yl)methyl]-pyrazole (690 mg, 1.76 mmol) was obtained 540 mg (81%) of the title compound as a light yellow powder; m.p. 112-119° C.

NMR (200 MHz;CDCl$_3$, TMS) δ: 7.94-7.04 (m,8H), 6.10 (s,1H), 5.14 (s,2H), 4.48 (s,2H), 3.38 (s,3H), 2.51 (t,J=7 Hz,2H), 1.57-1.46 (m,2H), 1.38-1.27 (m,2H), 0.87 (t, J=7 Hz, 3H).

EXAMPLE 172

Part A: 1-Methoxy-7-octen-2,4-dione

This diketone was prepared using the same procedure as described in Example 170, Part A.

From 5-hexen-2-one (19.6 g, 0.2 mol), methyl methoxyacetate (42 g, 0.4 mol) and sodium methoxide (15.1 g, 0.22 mol) in toluene (500 ml) was obtained 11.3 g (33%) of the title compound following fractionation at 4 mm Hg; b.p. 111-122° C.

NMR (200 MHz;CDCl$_3$,TMS) δ: 5.79 (m,2H), 5.10-4.99 (m,2H), 3.99 (s,2H), 3.43 (s,3H), 2.43-2.33 (m,4H).

Part B: 3(5)-But-3-enyl-5(3)-methoxymethylpyrazole

This compound was prepared using the same procedure in Example 170, Part B.

From 1-methoxy-7-octen-2,4-dione (5.0 g, 29.4 mmol) and hydrazine hydrate (2.2 g, 44.1 mmol) was obtained 3.4 g (69%) of the title compound as a yellow oil.

NMR (200 MHz;CDCl$_3$,TMS) δ: 12-11 (br,1H), 6.08 (s,1H), 5.91-5.77 (m,1H), 5.09-4.97 (m,2H), 4.48 (s,2H), 3.37 (s,3H), 2.77-2.70 (t,J=7 Hz,2H), 2.43-2.33 (m,2H).

Part C: 3-Methoxymethyl-5-but-3-enyl and 5-methoxy-methyl-3-but-3-enyl-1-[(2'-carbomethoxybiphenyl-4-yl)methyl]-pyrazoles These compounds could be prepared using the procedures described in Example 170, Part C. An alternative procedure could also be performed with comparable results, whereby the NaH is replaced with an equivalent amount of K$_2$CO$_3$ and the mixture heated to 65° C. for 18-24 hours.

From 3(5)-but-3-enyl-5(3)-methoxymethyl-pyrazole (2.0 g, 12.0 mmol), methyl 4¹-bromomethylbiphenyl-2-carboxylate (4.8 g, 15.6 mmol), sodium hydride (0.33 g, 14.3 mmol) or potassium carbonate (2.0 g, 14.3 mmol) in DMF (75 ml) was obtained 6 g of the crude title compounds which were separated by flash chromatography on silica gel (400 g; 10-20% EtOAc/hexanes).

Isolated was 1.22 g of the 5-methoxymethyl-3-but-3-enyl isomer (high R$_f$) : NMR (200 MHz;CDCl$_3$, TMS) δ: 7.83-7.12(m,8H), 6.10(s,1H), 5.96-5.83(m,1H), 5.38(s,2H), 5.11-4.96(m,2H), 4.34(s,2H), 3.63(s,3H), 3.29(s,3H), 2.74(t,J=8 Hz,2H), 2.47-2.40(m,2H).

Also isolated was 2.19 g of the 3-methoxymethyl-5-but-3-enyl isomer (low R$_f$): NMR (200 MHz;CDCl$_3$,TMS) δ: 7.83-7.07 (m,8H), 6.15 (s,1H), 5.81-5.72 (m,1H), 5.33 (s,2H), 5.06-4.97 (m,2H), 4.46 (s,2H), 3.60 (s,3H), 3.42 (s,3H), 2.62 (t,J=7 Hz,2H), 2.38-2.04 (m,2H).

Part D:
3-Methoxymethyl-5-but-3-enyl-1-[(2-carboxybiphenyl-4-yl)methyl]-pyrazole Ester hydrolysis was carried out as in Example 1, Part C.

From 3-methoxymethyl-5-but-3-enyl-1-[(2'-carbomethoxybiphenyl-yl)methyl]pyrazole (815 mg, 2.09 mmol) was obtained 640 mg (81%) of the title compound as a light yellow solid; m.p. 100-106° C.

NMR (200 MHz;CDCl$_3$,TMS) δ: 7.94-7.05 (m,8H), 6.13 (s,1H), 5.80-5.60 (m,1H), 5.17 (s,2H), 5.05-4.96 (m,2H), 4.48 (s,2H), 3.38 (s,3H), 2.61 (t,J=8 Hz,2H), 2.31 (m,2H).

EXAMPLE 173

Part A: 1-Methoxy-2,4-heptadione

This diketone was prepared using the same procedure in Example 170, Part A.

From 2-pentanone (8.6 g, 100 mmol), methyl methoxyacetate (21 g, 200 mmol), and sodium methoxide (7.5 g, 110 mmol) in toluene (250 ml) was obtained 6.3 g (40%) of the title compound following distillation at 4 mm Hg; b.p. 98-108° C.

NMR (200 MHz;CDCl$_3$,TMS) δ: 5.79 (S,1H), 3.99 (s,2H), 3.43 (s,3H), 2.30 (t,J=7 Hz,2H), 1.71-1.60 (m,2H), 0.96 (t,J=7 Hz,3H).

Part B: 3(5)-Methoxymethyl-5(3)-propylpyrazole

This compound was prepared using the same procedure in Example 170, Part B.

From 1-methoxy-2,4-heptadione (7.0 g, 44.2 mmol) and hydrazine monohydrate (3.3 g, 66.4 mmol) was obtained 5.7 g (84%) of the title compound as a red liquid.

NMR (200 MHz;CDCl$_3$, TMS) δ: 10.5-9.5 (br,1H), 6.06 (s,1H), 4.48 (s,2H), 3.37 (s,3H), 2.60 (t,J=7.5 Hz,2H), 1.70-1.59 (m,2H), 0.94 (t,J=7.5 Hz,3H).

Part C: 3-Methoxymethyl-5-propyl- and 5-methoxymethyl-3-propyl-1-[(2'-carbomethoxybiphenyl-4-yl)methyl]pyrazole This compound was prepared using the procedure in Example 170, Part C.

From 3(5)-methoxymethyl-5(3)-propylpyrazole (3.4 g, 22 mmol), methyl 4'-bromomethylbiphenyl-2-carboxylate (8.7 g, 28.5 mmol) and sodium hydride (0.6 g, 26.4 mmol) in DMF (100 ml) was obtained, following workup and flash chromatography, 1.23 g (15%) of the 5-methoxymethyl (high R$_f$) isomer and 3.80 g (46%) of the 3-methoxymethyl (low R$_f$) isomer.

NMR (high R$_f$,200 MHz; CDCl$_3$,TMS) δ: 7.82-7.06 (m,8H), 6.14 (s,1H), 5.32 (s,2H), 4.46 (s,2H), 3.61 (s,3H), 3.41 (s,3H), 2.50 (t,J=7 Hz,2H), 1.67-1.56 (m, 2H), 0.94 (t, J=7 Hz, 3H).

NMR (low R$_f$; 200 MHz; CDCl$_3$, TMS) δ: 7.82-7.12 (m,8H), 6.08 (s,1H), 5.37 (s,2H), 4.33 (s,2H), 3.61 (s,3H), 3.29 (S,3H), 2.61 (t,J=7 Hz,2H), 1.73-1.66 (m,2H), 0.97 (t,J=7 Hz,3H).

Part D:
3-Methoxymethyl-5-propyl-1-[(2'-carboxy-biphenyl-4-yl)methyl]pyrazole

Hydrolysis of this Pyrazole ester was carried out in the same fashion as in Example 1, Part C.

From 3-methoxymethyl-5-propyl-1-[(2'-carbomethoxybiphenyl-4-yl)methyl]pyrazole (807 mg, 2.13 mmol) was obtained 546 mg (70%) of the title compound as a light yellow solid; 48–53° C.

NMR (200 MHz;CDCl$_3$, TMS) δ: 7.94–7.05 (m,8H), 6.11 (s,1H), 5.16 (s,2H), 4.48 (s,2H), 3.38 (s,3H), 2.49 (t,J=7.5 Hz,2H), 1.64–1.53 (m,2H), 0.93 (t,J=7.5 Hz,3H).

EXAMPLE 174

5-Methoxymethyl-3-propyl-1-[2'-carboxybiphenyl-4-yl)methyl]pyrazole

Hydrolysis was performed in the same fashion as in Example 1, Part C.

From 5-methoxymethyl-3-propyl-1-[(2'-carbomethoxybiphenyl-4-yl)methyl]pyrazole (701 mg, 1.85 mmol) was obtained 432 mg (64%) of the title compound as a white solid; m.p. 100–104° C.

NMR (200 MHz, CDCl$_3$, TMS) δ: 7.93–7.10 (m,8H), 6.03 (s,1H), 5.14 (m,2H), 4.31 (s,2H), 3.29 (s,3H), 2.63 (t, J=7.5 Hz,2H), 1.66–1.59 (m,2H), 0.94 (t,J=7 Hz,3H).

EXAMPLE 175

Part A: Ethyl 2,4-dioxoheptanoate

To refluxing solution of sodium ethoxide (51.2 g, 0.75 mmol) in ethanol (170 ml) was added dropwise over 30 minutes a solution of 2-pentanone (59 g, 0.68 mol) in diethyl oxalate (99 g, 0.68 mol). The resulting turbid yellow mixture was refluxed further for 2 hours, cooled to room temperature, poured over 500 g ice with stirring and adjusted to pH 1–2 with concentrated sulfuric acid (~40 ml). The organic phase was extracted with benzene (3×300 ml), washed once with saturated aqueous sodium chloride and dried over anhydrous sodium sulfate, before being filtered, concentrated, and fractionally distilled at 0.1 mm Hg to give 48.2 g (38%) of the title compound as a yellow liquid; b.p. 85–95° C.

NMR (200 MHz; CDCl$_3$, TMS) δ: 14.6–14.3 (br, 1H; —OH of enol), 6.37 (s,1H; vinyl-H of enol), 4.35 (q,J=7 Hz,2H), 2.48 (t,J=7 Hz,2H), 1.75–1.64 (m,2H), 1.38 (t,J=7 Hz,3H), 0.98 (t,J=7 Hz,3H).

Part B: Ethyl 3(5)-propylpyrazole-5(3)-carboxylate

This compound was prepared in an analogous fashion to Example 170, Part B. In this case, however, equimolar quantities of diketone and hydrazine hydrate were used and the reaction mixture was stirred at room temperature several hours (instead of at reflux, to avoid reaction of the ester function with hydrazine).

From ethyl 2,4-dioxoheptanoate (19.5 g, 0.11 mmol) and hydrazine hydrate (5.2 g, 0.11 mmol) in ethanol (450 ml) was obtained 20 g (100%) of the title compound as a yellow oil, used in subsequent reactions without further purification.

NMR (200 MHz;CDCl$_3$,TMS) δ: 14.5–14.0 (br,1H), 6.37 (s,1H), 4.35 (q,J=7 Hz,2H), 2.48 (t,J=7 Hz,2H), 1.75-1.64 (m,2H), 1.38 (t,J=7 Hz,3H), 0.97 (t,J=7 Hz,3H).

Part C: 3-carboethyoxy-5-propyl- and 5-carboethoxy-3-propyl-1-[(2'-carbomethoxybiphenyl-4yl)-methyl]pyrazoles These isomers were prepared using the procedure for Example 172, Part C.

From ethyl 3(5)-propylpyrazole-5(3)-carboxylate (3.0 g, 16.5 mmol), methyl 4'-bromomethylbiphenyl-2-carboxylate (5.5 g, 18.1 mmol) and potassium carbonate (2.5 g, 18.1 mmol) in DMF (100 ml) was obtained, following workup and flash chromatography, 2.1 g (31%) of the 5-carboethoxy (high R$_f$) isomer and 2.7 g (40%) of the 3-carboethoxy isomer.

NMR (low R$_f$, 200 MHz;CDCl$_3$,TMS) δ: 7.84–7.09 (m,8H), 6.67 (s,1H), 5.44 (s,2H), 4.42 (q,J=7 Hz,2H), 3.62 (s,3H), 2.50 (t,J=7 Hz,2H), 1.68–1.56 (m,2H), 1.41 (t,J=7 Hz,3H), 0.97 (t,J=7 Hz,3H).

NMR (high R$_f$, 200 MHz; CDCl$_3$, TMS) 7.82–7.23 (m,8H), 6.70 (s,1H), 5.76 (s,2H), 4.29 (q,J=7 Hz,2H), 3.60 (s,3H), 2.64 (t,J=7 Hz,2H), 1.75–1.64 (m,2H), 1.33 (t,J=7 Hz,3H), 0.97 (t,J=7 Hz,3H).

Part D:
3-Carboxy-5-propyl-1-[(2'-carboxybiphenyl-4-yl)methyl]pyrazole

Hydrolysis of these pyrazole diesters was carried out in the same fashion as in Part C, Example 1.

From 3-carboethoxy-5-propyl-1-[(2'-carbomethoxybiphenyl-4-yl)methyl]pyrazole (1.4 g, 3.4 mmol) was obtained 0.92 g (73%) of the corresponding title compound as a light yellow solid; m.p. 218–222° C.

NMR (200 MHz;CDCl$_3$,TMS) δ: 7.90–7.08 (m,8H), 6.66 (s,1H), 5.39 (s,2H), 3.67 (br,4H; CO$_2$H+H$_2$O), 2.54 (t,J=7.5 Hz,2H), 1.69–1.58 (m,2H), 0.95 (t,J=7 Hz,3H).

EXAMPLE 176

Part A: 3(5)-Hydroxymethyl-5(3)-propylpyrazole

To a slurry of lithium aluminum hydride (5.0 g, 132 mmol) in anhydrous ether (250 ml) was added dropwise a solution of ethyl 3(5)-propylpyrazole-5(3)-carboxylate (12.0 g, 65.81 mmol) in ether (250 ml). The resulting mixture was refluxed for 2 hours, the excess reductant was quenched by the (careful) dropwise addition of ethyl acetate, and the organic phase was washed with water before being dried over MgSO$_4$, filtered and concentrated to afford 8.7 g (95%) of the title compound as a pale yellow waxy solid.

NMR (200 MHz;CDCl$_3$,TMS) δ: 5.99 (s,1H), 4.64 (s,2H), 2.56 (t,J=7.5 Hz,2H), 1.68-1.57 (m,2H), 0.93 (t, J=7 Hz, 3H).

Part B: 3-Hydroxymethyl-5-propyl- and 5-hydroxymethyl-3-propyl-1-[(2'-carbomethoxybiphenyl-4-yl-methyl]pyrazoles These isomers were prepared using the procedure of Example 172, Part C.

From 3(5)-hydroxymethyl-5(3)-propylpyrazole (4.0 g, 28.5 mmol) was obtained 10.6 g of the crude title compounds which were separated by flash chromatography on silica gel (50% EtOAc/hexanes, then EtOAc).

Isolated was 3.79 g (37%) of the 5-hydroxymethyl-3-propyl isomer (high R$_f$): NMR (200 MHz;CDCl$_3$,TMS) δ: 7.83–7.12 (m,8H), 6.06 (s,1H), 5.38 (s,2H), 4.54 (s,2H), 3.61 (s,3H), 2.59 (t,J=8 Hz,2H), 1.72–1.61 (m,2H), 0.97 (t, J=7 Hz, 3H).

Also isolated was 1.70 g (17%) of the 3-hydroxymethyl-5-propyl isomer (low R$_f$): NMR (200 MHz; CDCl$_3$,TMS) δ: 7.84–7.07 (m,8H), 6.11 (s,1H), 5.31 (s,2H), 4.68 (s,2H), 3.63 (s,3H), 2.51 (t,J=7.5 Hz,2H), 1.68–1.57 (m,2H), 0.96 (t,J=7 Hz,3H).

Part C:

3-Hydroxymethyl-5-propyl-1-[(2'-carboxybiphenyl-4-yl)methyl]pyrazole

This compound was prepared according to the procedure of Example 1, Part C.

From 3-hydroxymethyl-5-propyl-1-[(2'-carbomethoxybiphenyl-4-yl)methyl]pyrazole (1.5 g, 4.1 mmol) was obtained 1.4 g (99%) of the title compound as an off-white solid, m.p. 119-125° C.

NMR (200 MHz;CDCl$_3$,TMS) δ: 7.48–7.00 (m,8H), 6.03 (s,1H), 4.85 (s,2H), 4.62 (s,2H), 2.47 (t,J=8HZ,2H), 1.59–1.49 (m,2H), 0.93 (t,J=7 Hz,3H).

EXAMPLE 177

5-Hydroxymethyl-3-propyl-1-[(2'-carboxybiphenyl-4-yl)methyl]pyrazole

This compound was prepared according to the procedure of Example 1, Part C.

From 5-hydroxymethyl-3-propyl-1-[(2'-carbomethoxybiphenyl-4-yl)methyl]pyrazole (2.0 g, 5.5 mmol) was obtained 1.7 g (89%) of the title compound as an off-white solid, m.p. 51-58° C.

NMR (200 MHz;CDCl$_3$,TMS) δ: 7.91–7.04 (m,8H), 5.99 (s,1H), 5.16 (s,2H), 4.43 (s,2H), 2.55 (t,J=7.5 Hz,2H), 1.66–1.55 (m,2H), 0.92 (t,J=7 Hz,3H).

EXAMPLE 178

Part A: 3(5)-Formyl-5(3)-propylpyrazole

To a solution of 3(5)-hydroxymethyl-5(3)-propylpyrazole (6.6 g, 47.1 mmol) in methylene chloride (250 ml) was added activated manganese dioxide (41 g, 471 mmol). The mixture was stirred overnight at room temperature before being filtered and concentrated to afford 5.8 g (89%) of the title compound as a pale yellow solid.

NMR (200 MHz;DMSO-d$_6$,TMS) δ:9.84 (s,1H), 6.53 (2s,1H), 2.61 (t,J=7.5 Hz,2H), 1.68–1.53 (m,2H), 0.89 (t, J=8 Hz, 3H).

Part B: 3-Formyl-5-propyl- and 5-formyl-3-propyl-1-[(2'-carbomethoxybiphenyl-4-yl)methyl]pyrazoles These isomers were prepared using the procedure for Example 172, Part C.

From 3(5)-formyl-5(3)-propylpyrazole (2,5 g, 18.1 mmol) was obtained 7.3 g of the crude title compounds which were separated by flash chromatography on silica gel (15% EtOAc/hexanes).

Isolated was 1.31 (20%) of the 5-formyl-3-propyl-isomer (high R$_f$): NMR (200 MHz;CDCl$_3$,TMS) δ: 9.79 (s,1H), 7.82–7.20 (m,8H), 6.73 (s,1H), 5.71 (s,2H), 3.59 (s,3H), 2.66 (t,J=7.5 Hz,2H), 1.75–1.65 (m,2H), 0.98 (t, J=7 Hz, 3H).

Also isolated was 2.94 g (45%) of the 3-formyl-5-propyl-isomer (low R$_f$): NMR (200 MHz;CDCl$_3$,TMS) δ: 9.97 (s,1H), 7.86–7.12 (m,8H), 6.65 (s,1H), 5.43 (s,2H), 3.64 (s,3H), 2.55 (t,J=7.5 Hz,2H), 1.70–1.59 (m,2H), 0.96 (t, J=7 Hz, 3H).

Part C:

3-Formyl-5-propyl-1-[(2'-carboxybiphenyl-4-yl)methyl]pyrazol

This compound was prepared according to the procedure illustrated by Example 1, Part C.

From 3-formyl-5-propyl-1-[(2'-carbomethoxybiphenyl-4-yl)methyl]pyrazole (1.5 g, 4.1 mmol) was obtained 420 mg (29%) of the title compound as an amorphous solid following flash chromatography on silica gel (EtOAc).

NMR (200 MHz;CDCl$_3$,TMS) δ: 9.94 (s,1H), 7.96–7.10 (m,8H), 6.64 (s,1H), 5.41 (s,2H), 2.53 (t,J=7.5 Hz,2H), 1.67–1.56 (m,2H), 0.93 (t,J=7 Hz,3H).

EXAMPLE 179

Part A:

5-Formyl-3-propyl-1-[(2'-carboxybiphenyl-4-yl)methyl]pyrazole

This compound was prepared according to the procedure of Example 1, Part C.

From 5-formyl-3-propyl-1-[(2'-carbomethoxybiphenyl-4-yl)methyl]pyrazole (0.94 g, 2.6 mmol) was obtained 600 mg (66%) of the title compound as a yellow solid following flash chromatography on silica gel (EtOAc), m.p. 149-153° C.

NMR (200 MHz;CDCl$_3$,CD$_3$OD,TMS) δ: 9.80 (m,1H), 7.89–7.13 (m,8H), 6.77 (s,1H), 5.69 (s,2H), 2.66 (t,J=7.5 Hz,2H), 1.76-1.61 (m,2H), 0.98 (t,J=7 Hz,3H).

Table 3 lists examples of pyrazoles of this invention which were prepared or could be prepared by procedures of Examples 170–179 or by procedures previously described herein.

TABLE 3
PYRAZOLES

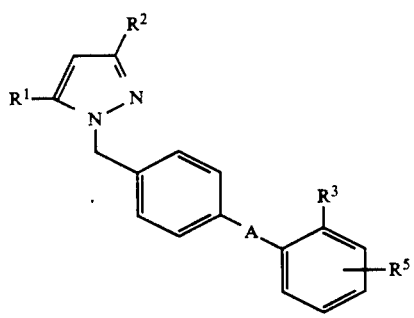

| Ex. No. | $R^1$ | $R^2$ | $R^3$ | $R^5$ | A | m.p.(°C.) |
|---|---|---|---|---|---|---|
| 170 | $CH_2OCH_3$ | n-butyl | $CO_2H$ | H | Single bond | 129–134 |
| 171 | n-butyl | $CH_2OCH_3$ | $CO_2H$ | H | Single bond | 112–119 |
| 172 | $(CH_2)_2CH=CH_2$ | $CH_2OCH_3$ | $CO_2H$ | H | Single bond | 100–106 |
| 173 | n-propyl | $CH_2OCH_3$ | $CO_2H$ | H | Single bond | 48–53 |
| 174 | $CH_2OCH_3$ | n-propyl | $CO_2H$ | H | Single bond | 100–104 |
| 175 | n-propyl | $CO_2H$ | $CO_2H$ | H | Single bond | 218–222 (dec.) |
| 176 | n-propyl | $CH_2OH$ | $CO_2H$ | H | Single bond | 119–125 |
| 177 | $CH_2OH$ | n-propyl | $CO_2H$ | H | Single bond | 51–58 |
| 178 | n-propyl | CHO | $CO_2H$ | H | Single bond | (amorph) |
| 179 | CHO | n-propyl | $CO_2H$ | H | Single bond | 149–153 |
| 180 | $CH_2OCH_3$ | Et | $CO_2H$ | H | Single bond | |
| 181 | $n-C_5H_{11}$ | $CH_2OCH_3$ | $CO_2H$ | H | Single bond | |
| 182 | $CH_2OCH_3$ | $n-C_6H_{13}$ | $CO_2H$ | H | Single bond | |
| 183 | $CH=CHCH_3$ | $CH_2OCH_3$ | $CO_2H$ | H | Single bond | |
| 184 | $CH_2OCH_3$ | $CH=CH(CH_2)_2CH_3$ | $CO_2H$ | H | Single bond | |
| 185 | $CH=CH(CH_2)_3CH_3$ | $CH_2OCH_3$ | $CO_2H$ | H | Single bond | |
| 186 | $CH_2OCH_3$ | $C\equiv CCH_3$ | $CO_2H$ | H | Single bond | |
| 187 | $C\equiv CCH_2CH_3$ | $CH_2OCH_3$ | $CO_2H$ | H | Single bond | |
| 188 | $CH_2OCH_3$ | $C\equiv C(CH_2)_2CH_3$ | $CO_2H$ | H | Single bond | |
| 189 | $C\equiv C(CH_2)_3CH_3$ | $CH_2OCH_3$ | $CO_2H$ | H | Single bond | |
| 190 | $(CH_2)_2OCH_3$ | n-propyl | $CO_2H$ | H | Single bond | |
| 191 | n-propyl | $(CH_2)_3OCH_3$ | $CO_2H$ | H | Single bond | |
| 192 | $(CH_2)_4OCH_3$ | n-propyl | $CO_2H$ | H | Single bond | |
| 193 | n-propyl | $(CH_2)_5OCH_3$ | $CO_2H$ | H | Single bond | |
| 194 | $(CH_2)_6OCH_3$ | n-propyl | $CO_2H$ | H | Single bond | |
| 195 | n-propyl | $CH_2OCH_2CH_3$ | $CO_2H$ | H | Single bond | |
| 196 | $CH_2O(CH_2)_2CH_3$ | n-propyl | $CO_2H$ | H | Single bond | |
| 197 | n-propyl | $CH_2O(CH_2)_3CH_3$ | $CO_2H$ | H | Single bond | |
| 198 | n-propyl | $CO_2CH_3$ | $CO_2H$ | H | Single bond | |
| 199 | n-propyl | $CO_2C_2H_5$ | $CO_2H$ | H | Single bond | |
| 200 | n-propyl | $CO_2$-n-$C_3H_7$ | $CO_2H$ | H | Single bond | |
| 201 | n-propyl | $CO_2$-n-$C_4H_9$ | $CO_2H$ | H | Single bond | |
| 202 | n-propyl | $CO_2$-n-$C_5H_{11}$ | $CO_2H$ | H | Single bond | |
| 203 | n-propyl | $CO_2$-c-$C_3H_5$ | $CO_2H$ | H | Single bond | |
| 204 | n-propyl | $CO_2$-c-$C_4H_7$ | $CO_2H$ | H | Single bond | |
| 205 | n-propyl | $CO_2$-c-$C_5H_9$ | $CO_2H$ | H | Single bond | |
| 206 | n-propyl | $CO_2$-c-$C_6H_{11}$ | $CO_2H$ | H | Single bond | |
| 207 | n-propyl | $CO_2Ph$ | $CN_4H$ | H | Single bond | |
| 208 | n-propyl | $CO_2CH_2Ph$ | $CN_4H$ | H | Single bond | |
| 209 | n-propyl | $CH_2COPh$ | $CO_2H$ | H | Single bond | |
| 210 | n-propyl | $CH_2COCH_2Ph$ | $CO_2H$ | H | Single bond | |
| 211 | n-propyl | $CH_2CO(CH_2)_2Ph$ | $CO_2H$ | H | Single bond | |
| 212 | n-propyl | $CH_2CO(CH_2)_3Ph$ | $CO_2H$ | H | Single bond | |
| 213 | n-propyl | $(CH_2)_4COCH_2Ph$ | $CO_2H$ | H | Single bond | |
| 214 | n-propyl | $(CH_2)_5COCH_2Ph$ | $CO_2H$ | H | Single bond | |
| 215 | n-propyl | $(CH_2)_6COCH_2Ph$ | $CO_2H$ | H | Single bond | |
| 216 | n-propyl | $CONH_2$ | $CO_2H$ | H | Single bond | |
| 217 | n-propyl | $CONHCH_3$ | $CO_2H$ | H | Single bond | |
| 218 | n-propyl | $CON(CH_3)_2$ | $CO_2H$ | H | Single bond | |
| 219 | n-propyl | CONHEt | $CO_2H$ | H | Single bond | |
| 220 | n-propyl | CONH-n-Pr | $CO_2H$ | H | Single bond | |
| 221 | n-propyl | CONH-n-Bu | $CO_2H$ | H | Single bond | |
| 222 | n-propyl | CONHPh | $CO_2H$ | H | Single bond | |
| 223 | n-propyl | $CONHCH_2Ph$ | $CO_2H$ | H | Single bond | |
| 224 | n-propyl |  | $CO_2H$ | H | Single bond | |

TABLE 3-continued
PYRAZOLES

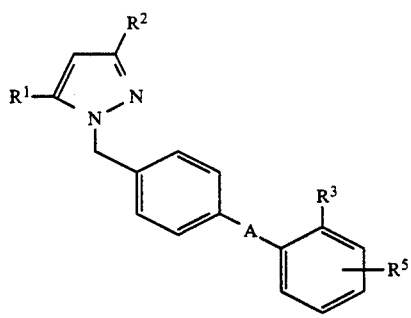

| Ex. No. | R$^1$ | R$^2$ | R$^3$ | R$^5$ | A | m.p.(°C.) |
|---|---|---|---|---|---|---|
| 225 | n-propyl | CON(piperidinyl) | CO$_2$H | H | Single bond | |
| 226 | n-propyl | CON(piperazinyl)NH | CO$_2$H | H | Single bond | |
| 227 | n-propyl | CON(piperazinyl)N—CH$_3$ | CO$_2$H | H | Single bond | |
| 228 | n-propyl | CON(piperazinyl)N—Et | CO$_2$H | H | Single bond | |
| 229 | n-propyl | CON(piperazinyl)N-n-Pr | CO$_2$H | H | Single bond | |
| 230 | n-propyl | CON(piperazinyl)N-n-Bu | CO$_2$H | H | Single bond | |
| 231 | n-propyl | CON(piperazinyl)N—Ph | CO$_2$H | H | Single bond | |
| 232 | n-propyl | CH$_2$OC(O)CH$_3$ | CO$_2$H | H | Single bond | |
| 233 | n-propyl | CH$_2$SCH$_3$ | CO$_2$H | H | Single bond | |
| 234 | n-propyl | CH$_2$S(O)CH$_3$ | CO$_2$H | H | Single bond | |
| 235 | n-propyl | CH$_2$SO$_2$CH$_3$ | CO$_2$H | H | Single bond | |
| 236 | n-propyl | CH=CHCH$_2$OH | CO$_2$H | H | Single bond | |
| 237 | n-propyl | CH=CHCH$_2$OCH$_3$ | CO$_2$H | H | Single bond | |
| 238 | n-propyl | CH=CHCH$_2$OEt | CO$_2$H | H | Single bond | |
| 239 | n-propyl | CH=CHCH$_2$O-n-C$_3$H$_7$ | CO$_2$H | H | Single bond | |
| 240 | n-propyl | CH=CHCH$_2$O-n-C$_4$H$_9$ | CO$_2$H | H | Single bond | |
| 241 | n-propyl | CH=CHCH$_2$OC(O)H | CO$_2$H | H | Single bond | |

TABLE 3-continued
PYRAZOLES

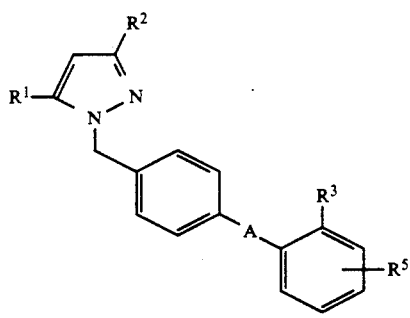

| Ex. No. | $R^1$ | $R^2$ | $R^3$ | $R^5$ | A | m.p.(°C.) |
|---|---|---|---|---|---|---|
| 242 | n-propyl | CH=CHCH$_2$OCCH$_3$ (O) | CO$_2$H | H | Single bond | |
| 243 | n-propyl | CH=CHCH$_2$OCC$_2$H$_5$ (O) | CO$_2$H | H | Single bond | |
| 244 | n-propyl | CH=CHCH$_2$OC-n-C$_3$H$_7$ (O) | CO$_2$H | H | Single bond | |
| 245 | n-propyl | CH=CHCH$_2$OC-n-C$_4$H$_9$ (O) | CO$_2$H | H | Single bond | |
| 246 | n-propyl | CH=CHCCH$_3$ (O) | CO$_2$H | H | Single bond | |
| 247 | n-propyl | CH$_2$NHCO$_2$CH$_3$ | CO$_2$H | H | Single bond | |
| 248 | n-propyl | CH$_2$NHCO$_2$Et | CO$_2$H | H | Single bond | |
| 249 | n-propyl | CH$_2$NHCO$_2$-n-C$_3$H$_7$ | CO$_2$H | H | Single bond | |
| 250 | n-propyl | CH$_2$NHCO$_2$-n-C$_4$H$_9$ | CO$_2$H | H | Single bond | |
| 251 | n-propyl | CH$_2$NHCO$_2$-n-C$_5$H$_{11}$ | CO$_2$H | H | Single bond | |
| 252 | n-propyl | CH$_2$NHCO$_2$-n-C$_6$H$_{13}$ | CO$_2$H | H | Single bond | |
| 253 | n-propyl | CH$_2$NHCO$_2$CH$_2$Ph | CO$_2$H | H | Single bond | |
| 254 | n-propyl | CH$_2$NHCO$_2$CF$_3$ | CO$_2$H | H | Single bond | |
| 255 | n-propyl | CH$_2$NHSO$_2$CH$_3$ | CO$_2$H | H | Single bond | |
| 256 | n-propyl | CH$_2$NHSO$_2$C$_2$F$_5$ | CO$_2$H | H | Single bond | |
| 257 | n-propyl | CH$_2$NHSO$_2$-n-C$_3$F$_7$ | CO$_2$H | H | Single bond | |
| 258 | n-propyl | CH$_2$NHSO$_2$-n-C$_4$F$_9$ | CO$_2$H | H | Single bond | |
| 259 | n-propyl | CH$_2$NHSO$_2$-n-C$_5$F$_{11}$ | CO$_2$H | H | Single bond | |
| 260 | n-propyl | CH$_2$NHSO$_2$-n-C$_6$F$_{13}$ | CO$_2$H | H | Single bond | |
| 261 | n-propyl | CH$_2$NHSO$_2$CH$_2$Ph | CO$_2$H | H | Single bond | |
| 262 | n-propyl | CH$_2$F | CO$_2$H | H | Single bond | |
| 263 | n-propyl | CH$_2$CN$_4$H | CO$_2$H | H | Single bond | |
| 264 | n-propyl | CH$_2$NHCO$_2$Ph | CO$_2$H | H | Single bond | |
| 265 | n-propyl | CH$_2$NHCO$_2$(CH$_2$)$_2$Ph | CO$_2$H | H | Single bond | |
| 266 | n-propyl | CH$_2$NHCO$_2$(CH$_2$)$_3$Ph | CO$_2$H | H | Single bond | |
| 267 | n-propyl | CH$_2$OCH$_3$ | CO$_2$H | NO$_2$ | NHCO | |
| 268 | n-propyl | CH$_2$OCH$_3$ | CO$_2$H | OCH$_3$ | NHCO | |
| 269 | n-propyl | CH$_2$OCH$_3$ | CO$_2$H | CH$_3$ | NHCO | |
| 270 | n-propyl | CH$_2$OCH$_3$ | CO$_2$H | F | NHCO | |
| 271 | n-propyl | CH$_2$OCH$_3$ | CO$_2$H | Cl | NHCO | |
| 272 | n-propyl | CH$_2$OCH$_3$ | CO$_2$H | Br | NHCO | |
| 273 | n-propyl | CH$_2$OCH$_3$ | NHSO$_2$CF$_3$ | I | NHCO | |
| 274 | n-propyl | CH$_2$OH | CO$_2$H | H | CO | |
| 275 | n-propyl | CH$_2$OH | CO$_2$H | H | O | |
| 276 | n-propyl | CO$_2$H | CO$_2$H | H | OCH$_2$ | |

EXAMPLE 277

Part A: Ethyl 5-formyl-1-[2'(1-triphenylmethyl-tetrazol-5-yl)biphenyl-4-yl-methyl]pyrrole-2-carboxylate This compound was prepared according to the procedure for Example 172, Part C.

From ethyl 5-formylpyrrole-2-carboxylate (10.0 g, 57.8 mmol) and 4'-bromomethyl-2-(1-triphenylmethyl-tetrazol-5-yl)biphenyl (37.0 g, 65.8 mmol) was obtained 18.4 g (48%) of the title compound as a light pink solid; m.p. 64-72° (dec.).

NMR (200 MHz;CDCl$_3$,TMS) δ: 9.6 (s,1H), 7.9–6.8 (m,25H), 6.05 (s,2H), 4.2 (q,J=7 Hz,2H), 1.25 (t,J=7 Hz,3H).

Part B: Ethyl 5-(1-hydroxypropyl-1-[2'-(1-triphenylmethyltetrazol-5-yl)biphenyl-4-yl-methyl]pyrrole-2-carboxylate Into a solution of 5-formyl-1-[2'-(1-triphenylmethyl-tetrazol-5-yl)biphenyl-4-yl-methyl]pyrrole-2-carboxylate (2.0 g, 3.1 mmol) in dry ether (100 ml) cooled to −78° C. was syringed a solution of ethyl magnesium bromide (1.3 ml of a 3.0M solution in ether; 4.0 mmol) dropwise over 10 minutes. The mixture was allowed to stir for 2 hours while being allowed to warm to room temperature. The mixture was quenched with 10% aqueous ammonium chloride (20 ml) and the organic phase was washed with saturated aqueous sodium bicarbonate (50 ml), saturated aqueous sodium chloride (50 ml) and dried (MgSO4) before being filtered and concentrated to leave 2.0 g (95%) of a white solid which could be chromatographed on silica gel but was generally used without further purification, being one spot by tlc.

NMR (200 MHz;CDCl3,TMS) δ: 7.87−6.72 (m,24H), 6.22 (d,J=4 Hz,1H), 5.72 (ABq,J=12 Hz,J=16 Hz,2H), 4.42−4.28 (m,1H), 4.16 (q,J=7 Hz,2H), 1.81−1.74 (m,2H), 1.26 (t,J=7 Hz,3H), 0.82 (t,J=7 Hz,3H).

Part C: (Cis- and trans-)ethyl 5-(1-propenyl)-1-[2'-(1-triphenylmethyltetrazol-5-yl)biphenyl-4-yl-methyl]pyrrole-2-carboxylate To a solution of ethyl 5-(1-hydroxypropyl)-1-[2'-(1-triphenylmethyltetrazol-5-yl)biphenyl-4-yl-methyl]pyrrole-2-carboxylate (2.0 g, 3.0 mmol) in methylene chloride (100 ml) at 0° C. was added DBU (2.0 ml, 12.0 mmol) followed by methanesulfonyl chloride (0.7 ml, 9.0 mmol). The mixture was stirred overnight at room temperature whereupon an additional aliquot of DBU (2.0 ml) and methanesulfonyl chloride (0.7 ml) were added and the mixture was allowed to stir an additional 24 hours. The mixture was poured into a separatory funnel and washed with water (3×50 ml) and saturated aqueous sodium bicarbonate solution (50 ml) before being dried (MgSO4), filtered and concentrated. The crude residue was purified by flash chromatography on silica gel (150 g, 10–30% EtOAc/hexanes) to give the title compounds as a mixture of cis/trans isomers (ca. ¼).

NMR (200 MHz;CDCl3,TMS;trans-isomer) δ: 7.88-6.75 (m,24H), 6.33 (d,J=4 Hz,1H), 6.19−6.13 (m,2H), 5.56 (s,2H), 4.14 (q,J=7 Hz,2H), 1.68 (d,J=5 Hz,3H), 1.24 (t, J=7 Hz, 3H).

The cis-isomer was evident by virtue of a weak benzylic methylene (singlet) at 5.66 δ as well as a comparably weak allylic methyl (doublet, J=5 Hz) at 1.85 δ.

This cis-trans mixture could be carried through to the next step or later separated following subsequent transformations, leading to propenyl analogues.

Part D: Ethyl 5-n-propyl-1-[2'-(1-triphenylmethyl-tetrazol-5-yl)biphenyl-4-yl-methyl]pyrrole-2-carboxylate A solution of (cis- and trans-) ethyl 5-(1-propenyl)-1-[2'-(1-triphenylmethyltetrazol-5-yl)biphenyl-4-yl-methyl]pyrrole-2-carboxylate (350 mg, 0.53 mmol) in benzene (35 ml) containing 5% Pd/C (35 mg) in a Paar bottle was placed on a Pear apparatus under 40 psi H2 and shaken for about 4 hours at room temperature. The mixture was suction filtered through Celite and concentrated to leave 350 mg of a white solid.

NMR (200 MHz;CDCl3,TMS) δ: 7.88-6.68 (m,24H), 6.01 (d,J=4 Hz,1H), 5.53 (s,2H), 4.14 (q,J=7 Hz,2H), 2.33 (t,J=7.5 Hz,2H), 1.57−1.50 (M,2H), 1.25 (t,J=7 Hz,3H), 0.83 (t, J=7. 5 Hz, 3H).

Part E: Ethyl 5-n-propyl-1-[2'-(1H-tetrazol-5-yl)biphenyl-4-yl-methyl]pyrrole-2-carboxylate This compound was prepared according to the procedure of Example 3, Part C.

From ethyl 5-n-propyl-1-[2'-(1-triphenylmethyltetrazol-5-yl)biphenyl-4-yl-methyl]-pyrrole-2-carboxylate (400 mg, 0.6 mmol) was obtained 126 mg (50%) of the title compound as an amorphous white solid.

NMR (200 MHz;CDCl3,TMS) δ: 7.87−6.83 (m,9H), 6.05 (d,J=4 Hz,1H), 5.56 (s,2H), 4.20 (q,J=7 Hz,2H), 2.48 (t,J=7.5 Hz,2H), 1.68−1.57 (m,2H), 1.31 (t,J=7 Hz,3H), 0.95 (t, J=7 Hz, 3H).

EXAMPLE 278

Part A: Ethyl 5-formyl-1-[(2'-t-butoxycarbonylbi-phenyl-4-yl)methyl]pyrrole-2-carboxylate This compound was prepared according to the procedure of Example 172, Part C.

From ethyl 5-formylpyrrole-2-carboxylate (4.0 g, 23.9 mmol) and t-butyl 4'-bromomethylbiphenyl-2-carboxylate (10.0 g, 28.7 mmol) was obtained 8.2 g (71%) of the title compound as a pale yellow oil following flash chromatography on silica gel (10% EtOAc/hexanes).

NMR (200 MHz;CDCl3,TMS) δ: 9.75(s,1H), 7.78−6.96 (m,10H), 6.19 (s,2H), 4.30 (q,J=d7.5 Hz,2H), 1.35 (t,J=7.5 Hz, 3H), 1.15 (s,9H).

Part B: Ethyl 5-(1-hydroxypropyl)-1-[(2'-t-butoxycarbonylbiphenyl-4-yl)methyl]pyrrole-2-carboxylate This compound was prepared according to the procedure of Example 277, Part B.

From ethyl 5-formyl-1-[(2'-t-butoxycarbonylbiphenyl-4-yl)methyl]pyrrole-2-carboxylate (7.2 g, 16.6 mmol) was obtained 6.4 g (83%) of the title compound following flash chromatography on silica gel (10% EtOAc/hexanes).

NMR (200 MHz;CDCl3,TMS) δ: 7.77−6.90 (m,9H), 6.24 (d,J=4 Hz,1H), 5.85 (ABq,J=17 Hz,J=23 Hz,2H), 4.51 (m,1H), 4.20 (q,J=7.5 Hz,2H), 1.89 (m,2H), 1.27 (t,J=7.5 Hz,3H), 1.21 (s,9H), 0.95 (t,J=7.5 Hz,3H).

Part C: (Cis- and trans-) ethyl 5-(1-propenyl)-1-[(2'-t-butoxycarbonylbiphenyl-4-yl)methyl]pyrrole-2-carboxylate This cis/trans mixture (only about 10% of the cis-isomer was observed in this case) was prepared according to the procedure of Example 277, Part C.

From ethyl 5-(1-hydroxypropyl)-1-[(2'-t-butoxycarbonylbiphenyl-4-yl)methyl]pyrrole-2-carboxylate (5.7 g, 12.3 mmol) was obtained the title compounds as a yellow viscous oil following flash chromatography on silica gel.

NMR (200 MHz;CDCl3,TMS, trans-isomer) δ: 7.77−6.99 (m,10H), 6.35−6.25 (m,2H), 5.72 (s,2H), 4.22 (q,J=7 Hz,2H), 1.83 (d,J=5 Hz,3H), 1.26 (t,J=7 Hz,3H), 1.18 (s,9H).

Part D: Ethyl 5-n-propyl-1-[(2'-t-butoxycarbonylbiphenyl-4-yl)methyl]pyrrole-2-carboxylate This compound was prepared according to the procedure of Example 277, Part D.

From (cis- and trans-) ethyl 5-(1-propenyl)-1-[(2'-t-butoxycarbonylbiphenyl-4-yl)methyl]pyrrole-2-carboxylate (1.2 g, 2.7 mmol) was obtained 0.9 g (75%) of the title compound as a viscous oil following flash chromatography on silica gel (10% EtOAc/hexanes).

NMR (200 MHz;CDCl$_3$,TMS) $\delta$: 7.78−6.90 (m,9H), 6.05 (d, J=4 Hz,1H), 5.68 (s,2H), 4.20 (q,J=7 Hz,2H), 2.51 (t,J=7.5 Hz, 2H), 1.72−1.57 (m,2H), 1.29 (t,J=7 Hz,3H), 1.20 (s, 9H) , 0.96 (t, J=7 Hz, 3H).

Part E: Ethyl 5-n-propyl-1-[(2'-carboxybiphenyl-4-yl)methyl]pyrrole-2-carboxylate Ethyl 5-n-propyl-1-[(2'-t-butoxycarbonylbiphenyl-4-yl)methyl]pyrrole-2-carboxylate (600 mg, 1.34 mmol) was stirred with formic acid (6 ml) at room temperature for 4 hours (slowly dissolved to a homogenous yellow solution). The mixture was diluted to about 50 ml with water to give a white precipitate which was filtered and subsequently purified by flash chromatography on silica gel (10% EtOAc/hexanes) to give 419 mg (80%) of the compound; m.p. 111-115° C.

NMR (200 MHz; CDCl$_3$,TMS) $\delta$: 7.92−6.91 (m,9H), 6.02 (d, J=4 Hz,1H), 5.65 (s,2H), 4.19 (q,J=7 Hz,2H), 2.49 (t,J=7.5 Hz, 2H), 1.67−1.55 (m,2H), 1.26 (t,J=7 Hz,3H), 0.92 (t, J=7 Hz, 3H).

EXAMPLE 279

Part A: 5-n-Propyl-1-[(2'-carboxybiphenyl-4-yl)-methyl]-pyrrole-2-carboxylic acid This compound was prepared using the procedure of Example 1, Part C.

From ethyl 5-n-propyl-1-[(2'-Carboxybiphenyl-4-yl)methyl]pyrrole-2-carboxylate (235 mg, 0.6 mmol) was obtained 188 mg (86%) of the title compound as a white solid; m.p. 135-137° C. (dec.).

NMR (200 MHz; CDCl$_3$,CD$_3$OD,TMS) $\delta$: 7.86−6.88 (m,9H), 6.05 (d,J=4 Hz,1H), 5.62 (s,2H), 2.50 (t,J=7 Hz,2H), 1.70−1.58 (m,2H), 0.95 (t,J=7 Hz,3H).

EXAMPLE 280

Part A: 5-n-propylpyrrole-2-carboxaldehyde

To an anhydrous solution of 6-dimethylamino-1-azafulvene dimer (125; 12.0 g, 49.1 mmol) in THF (500 ml) at −15° C. was added dropwise a solution of 5-butyllithium in pentane (1.7 M; 87 ml, 147 mmol) over 5 minutes. The yellow cloudy solution was slowly warmed to 0° C. over 10 minutes and stirred at this temperature for a further 20 minutes. The resulting deep violet colored solution was treated with 1-iodopropane (19.2 ml, 196 mmol) and allowed to warm to room temperature over 2 hours. The mixture was treated with water (20 ml) and saturated aqueous sodium bicarbonate (20 ml) and refluxed for 15 hours. The mixture was extracted into methylene chloride and the organic phase was washed with saturated aqueous sodium bicarbonate, dried over anhydrous magnesium sulfate, filtered and concentrated to a dark liquid residue (15.2 g) by rotary evaporation. Flash chromatography (silica gel, 500 g; EtOAc/hexanes, 5/95) gave 7.85 g (60%) of the title compound as a pale brown liquid.

NMR (200 MHz; CDCl$_3$, TMS) $\delta$: 10.6−10.4 (br,1H), 9.35 (s,1H), 6.90 (t,j=1-2 Hz,1H), 6.05 (t,J=1-2 Hz,1H), 2.6 (t,J=7 Hz,2H), 1.75−1.55 (m,2H), 1.0−0.8 (t,J=7 Hz,3H).

Part B: 5-n-propyl-1-[(2'-t-butoxycarbonylbiphenyl-4-yl)methyl]pyrrole-2-carboxaldehyde To a solution of 5-n-propylpyrrole-2-carboxaldehyde (2.5 g, 18.9 mmol) and t-butyl 41-bromomethylbiphenyl-2-carboxylate (7.2 g, 20.7 mmol) in methylene chloride (75 ml) was added 2.5N NAOH (15 ml) and Aliquat 336 (1.5 g, 3.7 mmol). The mixture was vigorously stirred at room temperature overnight (~18 hours). The organic phase was washed with water (50 ml) and saturated aqueous sodium chloride (50 ml) before being dried (MgSO$_4$), filtered and concentrated to leave 10.1 g of a dark oily residue. Flash chromatography (silica gel, 300 g; EtOAc/hexanes, 1/9) gave 5.84 g (79%) of a pale 2.0 yellow viscous oil.

NMR (200 MHz; CDCl$_3$,TMS) $\delta$: 9.46 (s,1H), 7.78−6.96 (m,9H), 6.15 (d,J=3 Hz,1H), 5.69 (s,2H), 2.53 (t,J=7.5 Hz,2H), 1.72−1.61 (m,2H), 1.20 (s,9H), 0.97 (t, J=7 Hz, 3H).

Part C: 5-n-propyl-1-[(2'-carboxybiphenyl-4-yl)-methyl]pyrrole-2-carboxaldehyde This compound was prepared according to the procedure for Example 278, Part E. In this case, dilution of the reaction mixture with water gave an oily precipitate; therefore, it was extracted into EtOAc and the organic phase was dried (MgSO$_4$), filtered and concentrated before being purified by flash chromatography.

From 5-n-propyl-1-[(2'-t-butoxycarbonylbiphenyl-4-yl)methyl]pyrrole-2-carboxaldehyde (1.0 g, 2.55 mmol) and formic acid (10 ml) was obtained 0.64 g (72%) of the title compound as an off-white solid; m.p. 117-120° C.

NMR (200 MHz; CDCl$_3$, TMS) $\delta$: 9.44 (s,1H), 7.93−6.95 (m,9H),6.13 (d,J=4 Hz,1H), 5.68 (s,2H), 5.3−5.0 (br,1H, washes out in D$_2$O, 2.51 (t,J=7.5 Hz,2H), 1.67−1.55 (m,2H), 0.92 (t,J=7 Hz,3H).

Table 4 lists examples of pyrroles of this invention which were prepared or could be prepared by procedures of Examples 277-280 or by procedures previously described herein.

TABLE 4
PYRROLES

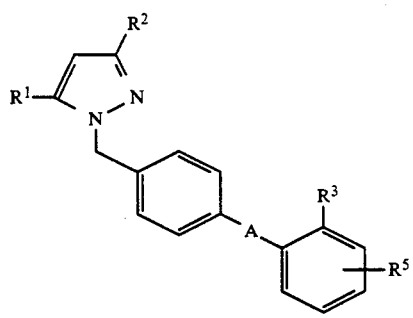

| Ex. No. | R¹ | R² | R³ | R⁵ | A | m.p.(°C.) |
|---|---|---|---|---|---|---|
| 277 | n-propyl | $CO_2Et$ | $CN_4H$ | H | Single bond | (amorph) |
| 278 | n-propyl | $CO_2Et$ | $CO_2H$ | H | Single bond | 111–115 |
| 279 | n-propyl | $CO_2Et$ | $CO_2H$ | H | Single bond | 135–137 |
| 280 | n-propyl | CHO | $CO_2H$ | H | Single bond | 117–120 |
| 281 | n-butyl | CHO | $CN_4H$ | H | Single bond | |
| 282 | ethyl | $CO_2CH_3$ | $CO_2H$ | H | Single bond | |
| 283 | $n-C_5H_{11}$ | $CO_2$-n-$C_3H_7$ | $CO_2H$ | H | Single bond | |
| 284 | $n-C_6H_{13}$ | $CO_2$-n-$C_4H_9$ | $CO_2H$ | H | Single bond | |
| 285 | n-propyl | $CO_2$-n-$C_5H_{11}$ | $CO_2H$ | H | Single bond | |
| 286 | n-propyl | $CO_2$-c-$C_3H_5$ | $CO_2H$ | H | Single bond | |
| 287 | n-propyl | $CO_2$-c-$C_4H_7$ | $CO_2H$ | H | Single bond | |
| 288 | n-propyl | $CO_2$-c-$C_5H_9$ | $CO_2H$ | H | Single bond | |
| 289 | n-propyl | $CO_2$-c-$C_6H_{11}$ | $CO_2H$ | H | Single bond | |
| 290 | n-propyl | $CO_2Ph$ | $CO_2H$ | H | Single bond | |
| 291 | n-propyl | $CO_2CH_2Ph$ | $CO_2H$ | H | Single bond | |
| 292 | n-propyl | $CONH_2$ | $CO_2H$ | H | Single bond | |
| 293 | n-propyl | $CONHCH_3$ | $CO_2H$ | H | Single bond | |
| 294 | n-propyl | $CON(CH_3)_2$ | $CO_2H$ | H | Single bond | |
| 295 | n-propyl | CONHEt | $CO_2H$ | H | Single bond | |
| 296 | n-propyl | CONH-n-Pr | $CO_2H$ | H | Single bond | |
| 297 | n-propyl | CONH-n-Bu | $CO_2H$ | H | Single bond | |
| 298 | n-propyl | CONHPh | $CO_2H$ | H | Single bond | |
| 299 | n-propyl | $CONHCH_2Ph$ | $CO_2H$ | H | Single bond | |
| 300 | n-propyl | CON-pyrrolidinyl | $CO_2H$ | H | Single bond | |
| 301 | n-propyl | CON-piperidinyl | $CO_2H$ | H | Single bond | |
| 302 | n-propyl | CON-morpholinyl | $CO_2H$ | H | Single bond | |
| 303 | n-propyl | CON-piperazinyl (NH) | $CO_2H$ | H | Single bond | |
| 304 | n-propyl | CON-piperazinyl (N—CH₃) | $CO_2H$ | H | Single bond | |
| 305 | n-propyl | CON-piperazinyl (N—Et) | $CO_2H$ | H | Single bond | |

TABLE 4-continued
PYRROLES

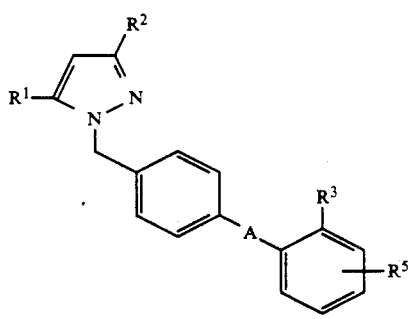

| Ex. No. | R¹ | R² | R³ | R⁵ | A | m.p.(°C.) |
|---|---|---|---|---|---|---|
| 306 | n-propyl | CON(piperazine)N-n-Pr | CO$_2$H | H | Single bond | |
| 307 | n-propyl | CON(piperazine)N-n-Bu | CO$_2$H | H | Single bond | |
| 308 | n-propyl | CON(piperazine)N—Ph | CO$_2$H | H | Single bond | |
| 309 | n-propyl | CH=CHCH$_2$OH | CO$_2$H | H | Single bond | |
| 310 | n-propyl | CH=CHCH$_2$OCH$_3$ | CO$_2$H | H | Single bond | |
| 311 | n-propyl | CH=CHCH$_2$OC$_2$H$_5$ | CO$_2$H | H | Single bond | |
| 312 | n-propyl | CH=CHCH$_2$O-n-C$_3$H$_7$ | CO$_2$H | H | Single bond | |
| 313 | n-propyl | CH=CHCH$_2$OC(O)-n-C$_4$H$_9$ | CO$_2$H | H | Single bond | |
| 314 | n-propyl | CH=CHC(O)OH$_3$ | | | | |
| 315 | CH=CHCH$_3$ | CH$_2$COPh | CO$_2$H | H | Single bond | |
| 316 | CH=CHCH$_3$ | CH$_2$COCH$_2$Ph | CO$_2$H | H | Single bond | |
| 317 | CH=CHCH$_3$ | CH$_2$CO(CH$_2$)$_2$Ph | CO$_2$H | H | Single bond | |
| 318 | CH=CHCH$_3$ | CH$_2$CO(CH$_2$)$_3$Ph | CO$_2$H | H | Single bond | |
| 319 | CH=CHCH$_3$ | (CH$_2$)$_4$COCH$_2$Ph | CO$_2$H | H | Single bond | |
| 320 | CH=CHCH$_3$ | (CH$_2$)$_5$COCH$_2$Ph | CO$_2$H | H | Single bond | |
| 321 | CH=CHCH$_3$ | (CH$_2$)$_6$COCH$_2$Ph | CO$_2$H | H | Single bond | |
| 322 | CH=CHCH$_2$CH$_3$ | CH$_2$OC(O)CH$_3$ | CN$_4$H | H | Single bond | |
| 323 | CH=CHCH$_2$CH$_3$ | CH$_2$SCH$_3$ | CO$_2$H | H | Single bond | |
| 324 | CH=CHCH$_2$CH$_3$ | CH$_2$S(O)CH$_3$ | CO$_2$H | H | Single bond | |
| 325 | CH=CHCH$_2$CH$_3$ | CH$_2$S(O)$_2$CH$_3$ | | | | |
| 326 | CH=CHCH$_2$CH$_3$ | CH$_2$NHCO$_2$CH$_3$ | CO$_2$H | H | Single bond | |
| 327 | CH=CHCH$_2$CH$_3$ | CH$_2$NHCO$_2$Et | CO$_2$H | H | Single bond | |
| 328 | CH=CHCH$_2$CH$_3$ | CH$_2$NHCO$_2$-n-C$_3$H$_7$ | CO$_2$H | H | Single bond | |
| 329 | CH=CHCH$_2$CH$_3$ | CH$_2$NHCO$_2$-n-C$_4$H$_9$ | CO$_2$H | H | Single bond | |
| 330 | CH=CHCH$_2$CH$_3$ | CH$_2$NHCO$_2$-n-C$_5$H$_{11}$ | CO$_2$H | H | Single bond | |
| 331 | CH=CHCH$_2$CH$_3$ | CH$_2$NHCO$_2$-n-C$_6$H$_{11}$ | CO$_2$H | H | Single bond | |
| 332 | CH=CHCH$_2$CH$_3$ | CH$_2$NHCO$_2$CH$_2$Ph | CO$_2$H | H | Single bond | |
| 333 | CH=CHCH$_2$CH$_3$ | CH$_2$NHCO$_2$CF$_3$ | CO$_2$H | H | Single bond | |

TABLE 4-continued
PYRROLES

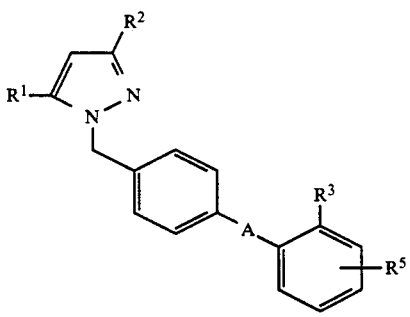

| Ex. No. | $R^1$ | $R^2$ | $R^3$ | $R^5$ | A | m.p.(°C.) |
|---|---|---|---|---|---|---|
| 334 | CH=CHCH$_2$CH$_3$ | CH$_2$NHSO$_2$CH$_3$ | CO$_2$H | H | Single bond | |
| 335 | CH=CHCH$_2$CH$_3$ | CH$_2$NHSO$_2$CF$_3$ | CO$_2$H | H | Single bond | |
| 336 | CH=CHCH$_2$CH$_3$ | CH$_2$NHSO$_2$C$_2$F$_5$ | CO$_2$H | H | Single bond | |
| 337 | CH=CHCH$_2$CH$_3$ | CH$_2$NHSO$_2$-n-C$_3$F$_7$ | CO$_2$H | H | Single bond | |
| 338 | CH=CHCH$_2$CH$_3$ | CH$_2$NHSO$_2$-n-C$_4$F$_9$ | CO$_2$H | H | Single bond | |
| 339 | CH=CHCH$_2$CH$_3$ | CH$_2$NHSO$_2$-n-C$_5$F$_{11}$ | CO$_2$H | H | Single bond | |
| 340 | CH=CHCH$_2$CH$_3$ | CH$_2$NHSO$_2$-n-C$_6$F$_{13}$ | CO$_2$H | H | Single bond | |
| 341 | CH=CHCH$_2$CH$_3$ | CH$_2$NHSO$_2$CH$_2$Ph | CO$_2$H | H | Single bond | |
| 342 | CH=CHCH$_2$CH$_3$ | CH$_2$F | CO$_2$H | H | Single bond | |
| 343 | CH=CHCH$_2$CH$_3$ | CH$_2$CN$_4$H | CO$_2$H | H | Single bond | |
| 344 | CH=CHCH$_2$CH$_3$ | CH$_2$NHCO$_2$Ph | CO$_2$H | H | Single bond | |
| 345 | CH=CHCH$_2$CH$_3$ | CH$_2$NHCO$_2$(CH$_2$)$_2$Ph | CO$_2$H | H | Single bond | |
| 346 | CH=CHCH$_2$CH$_3$ | CH$_2$NHCO$_2$(CH$_2$)$_3$Ph | CO$_2$H | H | Single bond | |
| 347 | CH=CH(CH$_2$)$_2$CH$_3$ | H | CO$_2$H | H | CO | |
| 348 | CH=CH(CH$_2$)$_3$CH$_3$ | H | CO$_2$H | H | CO | |
| 349 | C≡CCH$_3$ | CH$_2$OH | CO$_2$H | H | CO | |
| 350 | C≡CCH$_2$CH$_3$ | CH$_2$OH | CO$_2$H | H | CO | |
| 351 | C≡C(CH$_2$)$_2$CH$_3$ | CH$_2$OH | CO$_2$H | H | CO | |
| 352 | C≡C(CH$_2$)$_3$CH$_3$ | CH$_2$OH | CO$_2$H | H | CO | |
| 353 | n-propyl | CO$_2$H | CO$_2$H | NO$_2$ | NHCO | |
| 354 | n-propyl | CO$_2$H | CO$_2$H | OCH$_3$ | NHCO | |
| 355 | n-propyl | CO$_2$H | CO$_2$H | CH$_3$ | NHCO | |
| 356 | n-propyl | CO$_2$H | CO$_2$H | F | NHCO | |
| 357 | n-propyl | CO$_2$H | CO$_2$H | Cl | NHCO | |
| 358 | n-propyl | CO$_2$H | CO$_2$H | Br | NHCO | |
| 359 | n-propyl | CO$_2$H | NHSO$_2$CF$_3$ | I | NHCO | |
| 360 | n-propyl | CO$_2$H | CO$_2$H | H | NHCO | |
| 361 | CH=CHCH$_3$ | CH$_2$OCH$_3$ | CO$_2$H | H | O | |
| 362 | CH=CHCH$_3$ | (CH$_2$)$_2$OCH$_3$ | CO$_2$H | H | Single bond | |
| 363 | CH=CHCH$_3$ | (CH$_2$)$_3$OCH$_3$ | CO$_2$H | H | Single bond | |
| 364 | CH=CHCH$_3$ | (CH$_2$)$_4$OCH$_3$ | CO$_2$H | H | Single bond | |
| 365 | CH=CHCH$_3$ | (CH$_2$)$_5$OCH$_3$ | CO$_2$H | H | Single bond | |
| 366 | CH=CHCH$_3$ | (CH$_2$)$_6$OCH$_3$ | CO$_2$H | H | Single bond | |
| 367 | CH=CHCH$_3$ | CH$_2$OCH$_2$CH$_3$ | CO$_2$H | H | Single bond | |
| 368 | CH=CHCH$_3$ | CH$_2$O(CH$_2$)$_2$CH$_3$ | CO$_2$H | H | Single bond | |
| 369 | CH=CHCH$_3$ | CH$_2$O(CH$_2$)$_3$CH$_3$ | CO$_2$H | H | Single bond | |
| 370 | n-butyl | CO$_2$Et | CN$_4$H | H | Single bond | 157–158 |
| 371 | n-butyl | CO$_2$H | CN$_4$H | H | Single bond | 190–191 (dec.) |
| 372 | n-propyl | CHO | CN$_4$H | H | Single bond | 68–71 |

The compounds of Examples 370–372 were prepared as follows:

EXAMPLE 370

Part A: Ethyl 5-(1-hydroxybutyl)-1-[2'-(1-triphenyl-methyltetrazol-5-yl)biphenyl-4-yl -methyl]pyrrole-2-carboxylate This compound was prepared according to the procedure for Example 277, Part B.

From ethyl 5-formyl-1-[2'-(l-triphenylmethyltetrazol-5-yl)biphenyl-4-yl-methyl]pyrrole-2-carboxylate (5.0 g, 7.77 mmol) and n-propylmagnesium chloride (5.8 ml of a 2.0 M solution in ether; 11.6 mmol) was obtained 5.5 g of the title compound as a yellow viscous oil on workup, used in the following step without further purification.

NMR (200 MHz; CDCl$_3$, TMS) δ: 7.77–6.90 (m, 9H), 6.24 (d, J=4 Hz, 1H), 5.85 (q, J=17 Hz and 23 Hz, 2H), 4.51 (m, 1h), 4.20 (q, J=7.5 Hz, 2H), 1.85 (m, 4H), 1.27 (t, J=7.5 Hz, 3H), 1.21 (s, 9H), 0.95 (t, J=7.5 Hz, 3H).

Part B: (Cis- and trans-)ethyl 5-(1-butenyl)-1-[2'-(1-triphenylmethyltetrazol-5-yl)biphenyl-4-yl-methyl]pyrrole-2-carboxylate This compound was prepared according to the procedure for Example 277, Part C.

From ethyl 5-(1-hydroxybutyl)-1-[2'-(1-triphenyl-methyl-tetrazol-5-yl)biphenyl-4-yl-methyl]pyrrole-2-carboxylate (8.9 g, 12.9 mmol), methanesulfonyl chloride (5.9 ml, 77.6 mmol), and DBU (11.8 ml, 77.6 mmol) in THF (150 ml) was obtained 4.3 g (49%) of the title compound as a white solid following flash chromatography on silica gel (400 g; EtOAc/hexanes, 1); m.p. 119-121° C.

NMR (200 MHz; CDCl$_3$,TMS) δ: 7.88−6.77 (m, 24H), 6.36−6.06 (m, 3H; 2H vinyl +1H pyrrole), 5.57 (s, 2H), 4.14 (q, J=7 Hz, 2H), 2.10−1.97 (m, 2H), 1.25 (t, J=7 Hz, 3H), 0.94 (t, J=7 Hz), 3H).

Part C: Ethyl 5-n-butyl-1-[2'(1-triphenylmethyl-tetrazol-5-yl)biphenyl-4-yl-methyl]pyrrole-2-carboxylate This compound was prepared according to the procedure for Example 277, Part D.

From (cis- and trams-)ethyl 5-(1-butenyl)-1-[2'-(1-triphenylmethyltetrazol-5-yl)biphenyl-4-yl-methyl]pyrrole-2-carboxylate (4.0 g, 5.97 mmol) and 5% Pd/C (0.60 g) in benzene (200 ml) under H2 (40 psi) was obtained 3.66 g (91%) of the title compound as a white solid after filtration and concentration, used subsequently without further purification.

NMR (200 MHz, CDCl$_3$, TMS) δ: 7.88−6.68 (m, 24H), 6.01 (d, J=4 Hz, 1H), 5.53 (s, 2H), 4.15 (q, J=7 Hz, 2H), 2.36 (t, J=7 Hz, 2H), 1.55-1.47 (m, 2H), 1.32-1.18 (m and t, J=7 Hz, 5H), 0.83 (t, J=7 Hz, 3H).

Part D: Ethyl 5-n-butyl-1-[2'-(1H-tetrazol-5-yl)biphenyl-4-yl-methyl]-pyrrole-2-carboxylate This compound was prepared according to the procedure of Example 3, Part C.

In this case, since the starting material was not easily slurried in water (due to its waxy nature), it was first dissolved in EtOAc. From ethyl 5-n-butyl-1-[2'-1-triphenylmethyltetrazol-5-yl)biphenyl-4-yl-methyl]pyrrole-2-carboxylate (3.0 g, 4.45 mmol) in EtOAc/TFA/H$_2$O (20 ml/10 ml/10 ml) was obtained 1.23 g (64%) of the title compound as a white solid following flash chromatography on silica gel (30 g; EtOAc) and recrystallization (EtOAc/hexanes); m.p. 157-158° C.

NMR (200 MHz, CDCl$_3$, TMS) δ: 8.14−6.89 (m, 9H), 6.05 (d, J=4 Hz, 1H), 5.59 (s, 2H), 4.15 (q, J=7 Hz, 2H), 2.53 (t, J=7 Hz, 2H), 1.64−1.53 (m, 2H), 1.42-1.22 (m and t, J=7 Hz, 5H), 0.90 (t, J=7 Hz, 3H).

EXAMPLE 371

Part A: 5-n-Butyl-1-[2'-(1H-tetrazol-5-yl)biphenyl-4-yl-methyl]-pyrrole-2-carboxylic acid This compound was prepared according to the procedure for Example 1, Part C.

From ethyl 5-n-butyl-1-[21-(1H-tetrazol-5-yl)biphenyl-4-yl-methyl]pyrrole-2-carboxylate (0.97 g, 2.26 mmol) was obtained 0.68 g (75%) of the title compound as an off-white solid following recrystallization (EtOAc/EtOH/hexanes); m.p. 190-191° C. (dec.).

NMR (200 MHz; CDCl$_3$, TMS) δ: 7.86−6.82 (m, 9H), 6.05 (d, J=4 Hz, 1H), 5.56 (s, 2H), 2.51 (t, J=7 Hz, 2H), 1.62−1.54 (m, 2H), 1.41-1.26 (m, 2H), 0.89 (t, J=7 Hz, 3H).

EXAMPLE 372

Part A: 5-n-propyl-1-[2'-(1-triphenylmethyltetrazol-5-yl)biphenyl-4-yl-methyl]pyrrole-2-carboxaldehyde This compound was prepared according to the procedure for Example 280, Part B.

From 5-n-propylpyrrole-2-carboxaldehyde (2.0 g, 15.1 mmol) and 4'-bromomethyl-2-(l-triphenylmethyltetrazol-5-yl)biphenyl (10.9 g, 19.7 mmol) was obtained 5.2 g (75%) of the title compound as a yellow solid following flash chromatography (silica gel, 550 g; EtOAc/hexanes, 1/9).

NMR (200 MHz; CDCl$_3$, TMS) δ: 9.45 (s, 1H), 7.9−6.7 (m, 24H), 6.10 (d, J=2 Hz, 1H), 5.50 (s, 2H), 2.35 (t, J=7 Hz, 2H), 1.7−1.5 (m, 2H), 0.8 (t, J=7 Hz, 3H).

Part B: 5-n-propyl-1-[2'-(1H-tetrazol-5-yl)biphenyl-4-yl-methyl]pyrrole-2-carboxaldehyde To a solution of 5-n-propyl-1-[2'-(1-triphenylmethyltetrazol-5-yl)biphenyl-4-yl-methyl]pyrrole-2-carboxaldehyde (4.05 g, 6.6 mmol) in THF (25 ml) was added 4N HCl (11 ml) with stirring. The mixture was stirred at room temperature for 5 hours. The THF was removed by rotary evaporation and the residue was adjusted to pH 5-6 with 4N NAOH (~10 ml). The product was extracted into EtOAc (2×50 ml), the organic layer was dried (MgSO$_4$), filtered and concentrated. Flash chromatography of the reddish solid residue (1.97 g) on silica gel (30 g; EtOAc/hexanes, 1/1) gave 1.4 q of the title compound as a pale pink solid; m.p. 68–71° C.

NMR (200 MHz; CDCl$_3$, TMS) δ: 9.34 (s, 1H), 7.87−6.86 (m, 9H), 6.19 (d, J=4 Hz, 1H), 5.57 (s, 2H), 2.53 (t, J=7.5 Hz, 2H), 1.70−1.59 (m, 2H), 0.93 (t, J=7.3 Hz, 3H).

UTILITY

The hormone angiotensin II (AII) produces numerous biological responses (e.g., vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann et al., *J. Biol. Chem.*, 249, 825 (1974)], but with some modifications. The reaction mixture contained rat adrenal cortical microsomes (source of AII receptor) in Tris buffer and 2 nM of $^3$H-AII with or without potential AII antagonist. This mixture was incubated for 1 hour at room temperature and the reaction was subsequently terminated by rapid filtration and rinsing through glass microfibre filter. Receptor-bound $^3$H-AII trapped in filter was quantitated by scintillation counting. The inhibitory concentration (IC$_{50}$) of potential AII antagonist which gives 50% displacement of the total specifically bound $^3$H-AII is presented of the total the affinity of such compound for the AII receptor (see Table 4).

The potential antihypertensive effects of the compounds of this invention may be demonstrated by administering the compounds to rats made hypertensive by ligation of the left renal artery [Cagniano et al., *J Pharmacol. Exp. Ther.*, 208, 310 (1979)]. This procedure increases blood pressure by increasing renin production with consequent elevation of AII levels. Compounds are administered orally and/or intravenously via a cannula in the jugular vein. Arterial blood pressure is continuously measured directly through a carotid artery cannula and recorded using a pressure transducer and a polygraph. Blood pressure levels after treatment are compared to pretreatment levels to determine the antihypertensive effects of the compounds (See Table 5).

DOSAGE FORMS

The compounds of this invention can be administered for the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively, or concurrently, in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice. Diuretics such as furosemide and hydrochlorothiazide may enhance the antihypertensive effect of the compounds of this invention when the drugs are administered in physical combination or when a diuretic is administered before the compound of this invention. The compounds of this invention can be used in conjunction with non-steroidal anti-inflammatory drugs (NSAID's) such as ibuprofen, indomethacin, piroxicam, naproxen, ketoprofen, tolmetin, meclofenamate, sulindac and azapropazone to prevent the renal failure that sometimes occurs upon administration of NSAID'S.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.5 to 500 milligrams per kilogram of body weight. Ordinarily, from 1 to 100, and preferably 2 to 80, milligrams per kilogram per day in one or more applications is effective to obtain desired results.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

TABLE 5

| Example No. | Angiotensin II Receptor Binding $IC_{50}$ μ molar | Antihypertensive Effects in Renal Hypertensive Rats | |
|---|---|---|---|
| | | Intravenous Activity[1] | Oral Activity[2] |
| 1 | 3.0 | NA | NA |
| 2 | 1.0 | + | + |
| 3 | 6.0 | + | + |
| 4 | 0.3 | + | + |
| 67 | 0.82 | + | NA |
| 68 | 1.8 | + | NA |
| 69 | 0.73 | + | NA |
| 70 | 5.0 | + | NA |
| 71 | 0.82 | + | NA |
| 72 | 0.14 | + | + |
| 170 | 7.3 | + | NA |

TABLE 5-continued

| Example No. | Angiotensin II Receptor Binding IC$_{50}$ μ molar | Antihypertensive Effects in Renal Hypertensive Rats | |
|---|---|---|---|
| | | Intravenous Activity[1] | Oral Activity[2] |
| 171 | 0.29 | + | + |
| 172 | 0.72 | + | + |
| 173 | 6.7 | + | + |
| 174 | >1.0 | + | NA |
| 175 | 9.5 | + | NT |
| 176 | 2.3 | NA[3] | NA[3] |
| 177 | >3.0 | NA[3] | NA[3] |
| 178 | 4.1 | + | + |
| 179 | >3.0 | NA[3] | NA[3] |
| 277 | 1.6 | + | + |
| 278 | >3.0 | NA[3] | NA[3] |
| 279 | >12.0 | + | + |

[1]Significant decrease in blood pressure at 10 mg/kg or less.
[2]Significant decrease in blood pressure at 100 mg/kg or less.
NA[3] - Not active at 30 mg/kg i.v. or 30 mg/kg p.o.
NA - Not active at 100 mg/kg dosage administered.
NT - Not tested.

What is claimed is:

1. A compound selected from the group consisting of 3-n-butyl-5-methoxymethyl-1-[(2'-carboxybiphenyl-4-yl)methyl]pyrazole, 3-methoxymethyl-5-n-butyl-1-[(2'-carboxybiphenyl-4-yl)methyl] pyrazole, 3-methoxymethyl-5-(1-buten-1-yl)-1-[(2'-carboxybiphenyl-4-yl)methyl] pyrazole, 3-methoxymethyl-5-n-propyl-1-[(2'-carboxybiphenyl-4-yl)methyl] pyrazole or 5-methoxymethyl-3-n-propyl-1-[2'-carboxybiphenyl-4-yl)methyl] pyrazole; or a pharmaceutical salt thereof.

2. The compound of claim 1 which is 3-Methoxymethyl-5-n-butyl-1-[(2'-carboxybiphenyl-4-yl)methyl]-pyrazole.

3. The compound of claim 1 which is 5-Methoxymethyl-3-n-propyl-1-[(2'-carboxybiphenyl-4-yl)methyl]pyrazole.

* * * * *